United States Patent
Kennedy et al.

(10) Patent No.: US 9,856,537 B2
(45) Date of Patent: Jan. 2, 2018

(54) ALGORITHMS FOR DISEASE DIAGNOSTICS

(71) Applicant: Veracyte, Inc., South San Francisco, CA (US)

(72) Inventors: Giulia C. Kennedy, San Francisco, CA (US); Darya I. Chudova, San Jose, CA (US); Eric T. Wang, Milpitas, CA (US); Jonathan I. Wilde, Burlingame, CA (US)

(73) Assignee: VERACYTE, INC., South San Francisco, CA (US)

( * ) Notice: Subject to any disclaimer, the term of this patent is extended or adjusted under 35 U.S.C. 154(b) by 0 days.

(21) Appl. No.: 15/274,492

(22) Filed: Sep. 23, 2016

(65) Prior Publication Data

US 2017/0145514 A1  May 25, 2017

Related U.S. Application Data

(63) Continuation of application No. 12/964,666, filed on Dec. 9, 2010, now Pat. No. 9,495,515.

(60) Provisional application No. 61/285,165, filed on Dec. 9, 2009.

(51) Int. Cl.
| | |
|---|---|
| G06F 19/00 | (2011.01) |
| G06F 19/24 | (2011.01) |
| G06F 19/20 | (2011.01) |
| G01N 33/48 | (2006.01) |
| C12Q 1/68 | (2006.01) |
| C40B 30/04 | (2006.01) |
| G06N 99/00 | (2010.01) |

(52) U.S. Cl.
CPC ......... *C12Q 1/6886* (2013.01); *G06F 19/345* (2013.01); *G06N 99/005* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,645,691 A | 2/1972 | Knapp et al. |
| 5,965,360 A | 10/1999 | Zain et al. |
| 6,436,642 B1 | 8/2002 | Gould-Rothberg et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,280,922 B2 | 10/2007 | Mei et al. |
| 7,300,788 B2 | 11/2007 | Matsuzaki et al. |
| 7,319,011 B2 | 1/2008 | Riggins et al. |
| 7,323,305 B2 | 1/2008 | Leamon et al. |
| 7,335,762 B2 | 2/2008 | Rothberg et al. |
| 7,358,061 B2 | 4/2008 | Yamamoto et al. |
| 7,361,488 B2 | 4/2008 | Fan et al. |
| 7,598,052 B2 | 10/2009 | Giordano et al. |
| 7,901,888 B2 | 3/2011 | Kebebew |
| 8,541,170 B2 | 9/2013 | Kennedy et al. |
| 8,669,057 B2 | 3/2014 | Kennedy et al. |
| 9,234,244 B2 | 1/2016 | Zeiger et al. |
| 9,495,515 B1 | 11/2016 | Kennedy et al. |
| 2001/0051344 A1 | 12/2001 | Shalon et al. |
| 2002/0076735 A1 | 6/2002 | Williams et al. |
| 2002/0169137 A1 | 11/2002 | Reiner et al. |
| 2003/0186248 A1 | 10/2003 | Erlander et al. |
| 2003/0190602 A1 | 10/2003 | Pressman et al. |
| 2004/0019466 A1 | 1/2004 | Minor et al. |
| 2005/0042222 A1 | 2/2005 | Yamamoto et al. |
| 2005/0048533 A1 | 3/2005 | Sidransky et al. |
| 2005/0137805 A1 | 6/2005 | Lewin et al. |
| 2005/0240357 A1 | 10/2005 | Minor |
| 2005/0250125 A1 | 11/2005 | Novakoff |
| 2005/0266443 A1 | 12/2005 | Croce et al. |
| 2006/0019256 A1 | 1/2006 | Clarke et al. |
| 2006/0019615 A1 | 1/2006 | Ditmer |
| 2006/0035244 A1 | 2/2006 | Riggins et al. |
| 2006/0083744 A1 | 4/2006 | Chen et al. |
| 2006/0088851 A1 | 4/2006 | Erlander et al. |
| 2006/0094061 A1 | 5/2006 | Brys et al. |
| 2006/0105360 A1 | 5/2006 | Croce et al. |
| 2006/0127907 A1 | 6/2006 | Matsubara et al. |
| 2007/0020657 A1 | 1/2007 | Grebe et al. |
| 2007/0037186 A1 | 2/2007 | Jiang et al. |
| 2007/0048738 A1 | 3/2007 | Donkena et al. |
| 2007/0065833 A1 | 3/2007 | Gupta |
| 2007/0099209 A1 | 5/2007 | Clarke et al. |
| 2007/0105133 A1 | 5/2007 | Clarke et al. |
| 2007/0148667 A1 | 6/2007 | Williams et al. |
| 2007/0148687 A1 | 6/2007 | Bedingham et al. |
| 2007/0161004 A1 | 7/2007 | Brown et al. |
| 2007/0172844 A1 | 7/2007 | Lancaster et al. |

(Continued)

FOREIGN PATENT DOCUMENTS

| | | |
|---|---|---|
| EP | 1975245 A1 | 10/2008 |
| EP | 1975252 A1 | 10/2008 |

(Continued)

OTHER PUBLICATIONS

Wessels, et al., A protocol for building and evaluating predictors of disease state based on microarray data, Bioinformatics, 2005, 21:3755-3762.

(Continued)

*Primary Examiner* — Channing S Mahatan
(74) *Attorney, Agent, or Firm* — Wilson, Sonsini, Goodrich & Rosati, PC

(57) ABSTRACT

The present invention relates to compositions and methods for molecular profiling and diagnostics for genetic disorders and cancer, including but not limited to gene expression product markers associated with cancer or genetic disorders. In particular, the present invention provides algorithms and methods of classifying cancer, for example, thyroid cancer, methods of determining molecular profiles, and methods of analyzing results to provide a diagnosis.

24 Claims, 4 Drawing Sheets

(3 of 4 Drawing Sheet(s) Filed in Color)

(56) References Cited

U.S. PATENT DOCUMENTS

| | | |
|---|---|---|
| 2007/0220621 A1 | 9/2007 | Clarke et al. |
| 2007/0238119 A1 | 10/2007 | Yu et al. |
| 2008/0028302 A1 | 1/2008 | Meschkat |
| 2008/0044824 A1 | 2/2008 | Giordano et al. |
| 2008/0124344 A1 | 5/2008 | Combs et al. |
| 2008/0131892 A1 | 6/2008 | Becker et al. |
| 2008/0145841 A1 | 6/2008 | Libutti et al. |
| 2008/0274457 A1 | 11/2008 | Eng et al. |
| 2008/0281568 A1 | 11/2008 | Kao et al. |
| 2009/0020433 A1 | 1/2009 | Cohen et al. |
| 2009/0191535 A1 | 7/2009 | Connelly et al. |
| 2009/0204333 A1 | 8/2009 | Friend et al. |
| 2010/0055704 A1 | 3/2010 | Giordano et al. |
| 2010/0099093 A1 | 4/2010 | Weaver et al. |
| 2010/0131286 A1 | 5/2010 | Houlgatte et al. |
| 2010/0131432 A1 | 5/2010 | Kennedy et al. |
| 2010/0178653 A1 | 7/2010 | Aharonov et al. |
| 2010/0285979 A1 | 11/2010 | Zeiger et al. |
| 2011/0092375 A1 | 4/2011 | Zamore et al. |
| 2011/0152110 A1 | 6/2011 | Vierlinger et al. |
| 2011/0230372 A1 | 9/2011 | Willman et al. |
| 2011/0312520 A1 | 12/2011 | Kennedy et al. |
| 2012/0115743 A1 | 5/2012 | Davicioni et al. |
| 2012/0172243 A1 | 7/2012 | Davicioni et al. |
| 2012/0220474 A1 | 8/2012 | Kennedy et al. |
| 2013/0150257 A1 | 6/2013 | Abdueva et al. |
| 2013/0172203 A1 | 7/2013 | Yeatman et al. |
| 2013/0225662 A1 | 8/2013 | Kennedy et al. |
| 2013/0231258 A1 | 9/2013 | Wilde et al. |
| 2014/0228237 A1 | 8/2014 | Kennedy et al. |
| 2014/0349864 A1 | 11/2014 | Kennedy et al. |
| 2016/0068915 A1 | 3/2016 | Kennedy et al. |
| 2016/0312305 A1 | 10/2016 | Kennedy et al. |
| 2016/0312306 A1 | 10/2016 | Kennedy et al. |
| 2016/0312307 A1 | 10/2016 | Kennedy et al. |
| 2016/0312308 A1 | 10/2016 | Kennedy et al. |

FOREIGN PATENT DOCUMENTS

| | | |
|---|---|---|
| EP | 2366800 A1 | 9/2011 |
| JP | 2005168432 A | 6/2005 |
| WO | WO-2005005601 A2 | 1/2005 |
| WO | WO-2005005601 A3 | 4/2006 |
| WO | WO-2006062118 A1 | 6/2006 |
| WO | WO-2006127537 A2 | 11/2006 |
| WO | WO-2007038792 A2 | 4/2007 |
| WO | WO-2007038792 A3 | 11/2007 |
| WO | WO-2008104380 A2 | 9/2008 |
| WO | WO-2008119776 A1 | 10/2008 |
| WO | WO-2008104380 A3 | 11/2008 |
| WO | WO-2009020905 A2 | 2/2009 |
| WO | WO-2009026605 A2 | 3/2009 |
| WO | WO-2009029266 A2 | 3/2009 |
| WO | WO-2009037337 A1 | 3/2009 |
| WO | WO-2006127537 A3 | 4/2009 |
| WO | WO-2009042728 A1 | 4/2009 |
| WO | WO-2009126271 A1 | 10/2009 |
| WO | WO-2010056374 A2 | 5/2010 |
| WO | WO-2010073248 A2 | 7/2010 |
| WO | WO-2010056374 A3 | 9/2010 |
| WO | WO-2010073248 A3 | 9/2010 |
| WO | WO-2011143361 A2 | 11/2011 |

OTHER PUBLICATIONS

Affymetrix website for HG-U133A probe set list version 2004, Archived NetAffx Annotation Files (http://www.affymetrix.com/estore/catalog/131537/AFFY/Human+Genome+U133A+2.0+Array#1_3) printed Mar. 2015.

Bonora et al. Novel germline variants identified in the inner mitochondrial membrane transporter TIMM44 and their role in predisposition to oncocytic thyroid carcinomas. Br J Cancer. 2006;95(11):1529-36.

Brasseur et al. Papillary thyroid carcinoma in a 9-year-old girl with ataxia-telangiectasia. Pediatr Blood Cancer. 2008;50(5)1058-60.

Brozek et al. Thyroid cancer in two siblings with FAP syndrome and APC mutation. Int J Colorectal Dis. 2008;23(3):331-2.

Bugalho et al. Mutation analysis of the RET proto-oncogene and early thyroidectomy: results of a Portuguese cancer centre. Surgery. 2007;141(1):90-5.

Cameselle-Teijeiro et al. Follicular thyroid carcinoma with an unusual glomeruloid pattern of growth. Hum Pathol. 2008;39(10):1540-7.

Carda et al. Anaplastic carcinoma of the thyroid with rhabdomyosarcomatous differentiation: a report of two cases. Virchows Arch. 2005;446(1):46-51.

Castro et al. Adenomas and follicular carcinomas of the thyroid display two major patterns of chromosomal changes. J Pathol. 2005;206(3):305-11.

Castro et al.PAX8-PPARgamma rearrangement is frequently detected in the follicular variant of papillary thyroid carcinoma. J Clin Endocrinol Metab. 2006;91(1):213-20.

Cohen et al. Mutational analysis of BRAF in fine needle aspiration biopsies of the thyroid: a potential application for the preoperative assessment of thyroid nodules. Clin Cancer Res. 2004;10(8):2761-5.

De Lellis et al. The pathobiology of the human calcitonin (C)-cell: a review. Pathol Annu. 1981;16(Pt 2):25-52.

Del Senno et al. c-myc oncogene alterations in human thyroid carcinomas. Cancer Detect Prev. 1987;10(3-4):159-66.

Elise et al. RET genetic screening in patients with medullary thyroid cancer and their relatives: experience with 807 individuals at one center. J Clin Endocrinol Metab. 2007;92(12):4725-9.

Foppiani et al. Uncommon association of germline mutations of RET proto-oncogene and CDKN2A gene. Eur J Endocrinol. 2008;158(3):417-22.

Gasparre et al. Disruptive mitochondrial DNA mutations in complex I subunits are markers of oncocytic phenotype in thyroid tumors. Proc Natl Acad Sci USA. 2007;104(21):9001-6.

GeneAnnot website. Probesets for PROS1. Printed Nov. 8, 2016. 1 page.

GeneAnnot website. Probesets for RXRG. Printed Nov. 8, 2016. 1 page.

Gereben et al. Pretranslational regulation of type 2 deiodinase. Thyroid. 2005;15(8):855-64.

Giordano et al. Delineation, functional validation, and bioinformatic evaluation of gene expression in thyroid follicular carcinomas with the PAX8-PPARG translocation. Clin Cancer Res. 2006;12(7 Pt 1):1983-93.

Giordano et al. Molecular classification of papillary thyroid carcinoma: distinct BRAF, RAS, and RET/PTC mutation-specific gene expression profiles discovered by DNA microarray analysis. Oncogene. 2005;24(44):6646-56.

Gould et al. (1987). Synaptophysin expression in neuroendocrine neoplasms as determined by immunocytochemistry. Am J Pathol. 126(2):243-57.

Harach et al. Histology of familial thyroid tumours linked to a gene mapping to chromosome 19p13.2. J Pathol. 1999;189(3):387-93.

He, et al. A susceptibility locus for papillary thyroid carcinoma on chromosome 8q24. Cancer Res. Jan. 15, 2009;69(2):625-31.

He et al. The role of microRNA genes in papillary thyroid carcinoma. Proc Natl Acad Sci USA. 2005;102(52)19075-80.

Hemmer et al. Comparison of benign and malignant follicular thyroid tumours by comparative genomic hybridization. Br J Cancer. 1998;78(8):1012-7.

Holden et al. Tyrosine kinase activating mutations in human malignancies: implications for diagnostic pathology. Exp Mol Pathol. 2008; 85(1):68-75.

Hsu et al. Characterization of a novel tripartite nuclear localization sequence in the EGFR family. J Biol Chem. 2007;282(14):10432-40.

Inaji et al. Demonstration and diagnostic significance of pro-gastrin-releasing peptide in medullary thyroid carcinoma. Oncology. 2000;59(2)122-5.

(56) References Cited

OTHER PUBLICATIONS

Ito et al. Simultaneous expression of keratan sulphate epitope (a sulphated poly-N-acetyllactosamine) and blood group ABH antigens in papillary carcinomas of the human thyroid gland. Histochem J. 1996;28(9):613-23.
Jazdzewski et al. Common SNP in pre-miR-146a decreases mature miR expression and predisposes to papillary thyroid carcinoma. Proc Natl Acad Sci USA. 2008;105(20):7269-74.
Kakudo et al. Immunohistochemical study of substance P-like immunoreactivity in human thyroid and medullary carcinoma of the thyroid. J Submicrosc Cytol. 1983;15(2):563-8.
Kang et al. High prevalence of RET, RAS, and ERK expression in Hashimoto's thyroiditis and in papillary thyroid carcinoma in the Korean population. Thyroid. 2007;17(11):1031-8.
Lauter et al. Mutational analysis of CDKN1B, a candidate tumor-suppressor gene, in refractory secondary/tertiary hyperparathyroidism. Kidney Int. 2008;73(10):1137-40.
Lin et al. Expression of sodium iodide symporter in benign and malignant human thyroid tissues. Endocr Pathol. 2001;12(1):15-21.
Lui et al. 2008;CREB3L2-PPARgamma fusion mutation identifies a thyroid signaling pathway regulated by intramembrane proteolysis. Cancer Res. 68(17):7156-64.
Matsubayashi et al. Gastrin-releasing peptide immunoreactivity in medullary thyroid carcinoma. Cancer. 1984;53(11):2472-7.
Maximo et al. Somatic and germline mutation in GRIM-19, a dual function gene involved in mitochondrial metabolism and cell death, is linked to mitochondrion-rich (Hurthle cell) tumours of the thyroid. Br J Cancer. 2005;92(10):1892-8.
Nikolova et al. Genome-wide gene expression profiles of thyroid carcinoma: Identification of molecular targets for treatment of thyroid carcinoma. 2008;Oncol Rep. 20(1):105-21.
Notice of allowance dated Jun. 13, 2013 for U.S. Appl. No. 12/592,065.
Notice of allowance dated Oct. 18, 2013 for U.S. Appl. No. 13/318,751.
Office action dated Mar. 23, 2015 for U.S. Appl. No. 13/589,022.
Office action dated Sep. 8, 2016 for U.S. Appl. No. 15/164,241.
Office action dated Nov. 7, 2016 for U.S. Appl. No. 13/105,756.
Office action dated Nov. 17, 2016 for U.S. Appl. No. 13/589,022.
Office action dated Nov. 18, 2016 for U.S. Appl. No. 14/153,219.
Office action dated Nov. 30, 2016 for U.S. Appl. No. 13/708,439.
Panicker et al. A common variation in deiodinase 1 gene DIO1 is associated with the relative levels of free thyroxine and triiodothyronine. J Clin Endocrinol Metab. 2008;93(8):3075-81.
Pinto et al. mRNA expression of tachykinins and tachykinin receptors in different human tissues. Eur J Pharmacol. 2004;494(2-3):233-9.
Rosai et al. Pitfalls in the diagnosis of thyroid neoplasms. Pathol Res Pract. 1987:182(2):169-79.
Rosen et al. A six-gene model for differentiating benign from malignant thyroid tumors on the basis of gene expression. Surgery. 2005;138(6):1050-6; discussion 1056-7.
Sapio, et al., Detection of RETIPTC, TRK and BRAF mutations in preoperative diagnosis of thyroid nodules with indeterminate cytological findings, Clinical Endocrinology, 2007, 66: 678-683.
Satake et al. Overview of the primary structure, tissue-distribution, and functions of tachykinins and their receptors. Curr Drug Targets. 2006;7(8):963-74.
Subramaniam et al. Clonal characterization of sporadic cribriform-morular variant of papillary thyroid carcinoma by laser microdis-section-based APC mutation analysis. Am J Clin Pathol. 2007;128(6):994-1001.
Takakura et al. Oncogenic role of miR-17-92 cluster in anaplastic thyroid cancer cells. Cancer Sci. 2008;99(6):1147-54.
Tetzlaff et al. Differential expression of miRNAs in papillary thyroid carcinoma compared to multinodular goiter using formalin fixed paraffin embedded tissues. Endocr Pathol. 2007;18(3):163-73.
Thompson et al. Primary smooth muscle tumors of the thyroid gland. Cancer. 1997;79(3):579-87.
Todaro et al. Autocrine production of interleukin-4 and interleukin-10 is required for survival and growth of thyroid cancer cells. Cancer Res. 2006;66(3):1491-9.
Unger et al. Array CGH demonstrates characteristic aberration signatures in human papillary thyroid carcinomas governed by RET/PTC. Oncogene. 2008;27(33):4592-602.
Viale et al. Coexpression of cytokeratins and vimentin in normal and diseased thyroid glands. Lack of diagnostic utility of vimentin immunostaining. Am J Surg Pathol. 1989;13(12):1034-40.
Viney et al. Regulation of the cell-specific calcitonin/calcitonin gene-related peptide enhancer by USF and the Foxa2 forkhead protein. J Biol Chem. 2004;279(48):49948-55.
Wang et al. Association of the T1799A BRAF mutation with tumor extrathyroidal invasion, higher peripheral platelet counts, and over-expression of platelet-derived growth factor-B in papillary thyroid cancer. Endocr Relat Cancer. 2008;15(1):183-90.
Wang et al. The expression analysis of ICOS-L on activated T cells and immature dendritic cells as well as malignant B cells and Grave's-disease-derived thyroid tissues by two novel mAbs against human ICOS-L. Tissue Antigens. 2007;69(1):62-72.
Watanabe et al. Decrease of intrathyroidal CD161+ Valpha24+Vbeta11+NKT cells in Graves' disease. Endocr J. 2008; 55(1):199-203.
Wu et al. Uncommon mutation, but common amplifications, of the PIK3CA gene in thyroid tumors. J Clin Endocrinol Metab. 2005;90(8):4688-93.
Yang et al. C-myc, N-myc, N-ras, and c-erb-B: lack of amplification or rearrangement in human medullary thyroid carcinoma and a derivative cell line. Anticancer Res. 1990;10(1):189-92.
Yoon et al. Identification of a novel noncoding RNA gene, NAMA, that is downregulated in papillary thyroid carcinoma with BRAF mutation and associated with growth arrest. Int J Cancer. 2007;121(4):767-75.
Zabel et al. S-100 protein and neuron-specific enolase in parathyroid glands and C-cells of the thyroid. Histochemistry. 1987;86(4):389-92.
Zanna et al. Trop-1 are conserved growth stimulatory molecules that mark early stages of tumor progression. Cancer. 2007;110(2):452-64.
Zeng et al. The contributions of oestrogen receptor isoforms to the development of papillary and anaplastic thyroid carcinomas. J Pathol. 2008;214(4):425-33.
Zhu et al. U1 snRNP-dependent function of TIAR in the regulation of alternative RNA processing of the human calcitonin/CGRP pre-mRNA. Mol Cell Biol. 2003;23(17):5959-71.
Kasraeian, et al. A comparison of fine-needle aspiration, core biopsy, and surgical biopsy in the diagnosis of extremity soft tissue masses. Clin Orthop Relat Res. Nov. 2010;468(11):2992-3002. doi: 10.1007/s11999-010-1401-x.
Abrosimov et al. The cytoplasmic expression of MUC1 in papillary thyroid carcinoma of different histological variants and its correlation with cyclin D1 overexpression. Endocr Pathol. 2007;18(2):68-75.
Abubaker et al. Clinicopathological analysis of papillary thyroid cancer with PIK3CA alterations in a Middle Eastern population. J Clin Endocrinol Metab. 2008;93(2):611-8.
Adapt, The Peterson Institute for Cancer Research, probesets for ARSG, printed Jan. 10, 2013.
Adapt, The Peterson Institute for Cancer Research, probesets for FREM2, printed Jan. 10, 2013.
Adapt, The Peterson Institute for Cancer Research, probesets for GIMAP2, printed Jan. 10, 2013.
Adapt, The Peterson Institute for Cancer Research, probesets for HRASLS3, printed Jan. 10, 2013.
Adapt, The Peterson Institute for Cancer Research, probesets for PIGN, printed Jan. 10, 2013.
ADAPT website. Paterson Institute for Cancer Research. Probesets for AUTS2. Printed Jul. 1, 2014. 2 pages.
ADAPT website. Paterson Institute for Cancer Research. Probesets for FXYD6. Printed Jul. 1, 2014. 1 page.
Affymetrix: "Data Sheet Affymetrix(R) Genome-Wide Human SNP Array 6.0", 2007, pp. 1-4, XP002525407. Retrieved from the

(56) References Cited

OTHER PUBLICATIONS

Internet: URL:http://www.affymetrix.com/support/technical/datasheets/genomewide_snp6_datasheet.pdf.
Affymetrix Technical Note: GeneChip® Gene 1.0 ST Array Design (created Sep. 5, 2007; downloaded from http://media.affymetrix.com/support/technical/technotes/gene_1_0_st_technote.pdf).
Afink, et al. Molecular characterization of iodotyrosine dehalogenase deficiency in patients with hypothyroidism. J Clin Endocrinol Metab. Dec. 2008;93(12):4894-901.
Aldred et al. Caveolin-1 and caveolin-2, together with three bone morphogenetic protein-related genes, may encode novel tumor suppressors down-regulated in sporadic follicular thyroid carcinogenesis. Cancer Res. 2003;63(11):2864-71.
Aldred et al. Papillary and follicular thyroid carcinomas show distinctly different microarray expression profiles and can be distinguished by a minimum of five genes. J Clin Oncol. 2004;22(17):3531-9.
Alexander, et al. Preoperative diagnosis of benign thyroid nodules with indeterminate cytology. N Engl J Med. Aug. 23, 2012;367(8):705-15. doi: 10.1056/NEJMoa1203208. Epub Jun. 25, 2012. with supplementary appendix.
Arnesen et al. Expression of N-acetyl transferase human and human Arrest defective 1 proteins in thyroid neoplasms. Thyroid. 2005;15(10):1131-6.
Bai et al. Mutational analysis of thyroid transcription factor-1 gene (TTF-1) in lung carcinomas. In Vitro Cell Dev Biol Anim. 2008;44(1-2):17-25.
Baldi; et al., "DNA microarrays and gene expression: from experiments to data analysis and modeling. Cambridge university press, 2002."
Baloch, et al. Our approach to follicular-patterned lesions of the thyroid. J Clin Pathol. Mar. 2007;60(3):244-50. Epub Jun. 23, 2006.
Banito et al. Aneuploidy and RAS mutations are mutually exclusive events in the development of well-differentiated thyroid follicular tumours. Clin Endocrinol (Oxf). 2007;67(5):706-11.
Barden et al. Classification of follicular thyroid tumors by molecular signature: results of gene profiling. Clin Cancer Res. 2003;9(5):1792-800.
Baris et al. Transcriptional profiling reveals coordinated up-regulation of oxidative metabolism genes in thyroid oncocytic tumors. J Clin Endocrinol Metab. 2004;89(2):994-1005.
Bessarabova, et al. Bimodal gene expression patterns in breast cancer. BMC Genomics. Feb. 10, 2010;11 Suppl 1:S8. doi: 10.1186/1471-2164-11-S1-S8.
Boulesteix, et al. Evaluating microarray-based classifiers: an overview. Cancer Inform. 2008;6:77-97. Epub Feb. 29, 2008.
Cerutti et al. A preoperative diagnostic test that distinguishes benign from malignant thyroid carcinoma based on gene expression. J Clin Invest. 2004;113(8):1234-42.
Cerutti et al. Diagnosis of suspicious thyroid nodules using four protein biomarkers. Clin Cancer Res. 2006;12(11 Pt 1):3311-8.
Chan, et al. Integrating Transcriptomics and Proteomics. Drug Discovery and Development. Apr. 1, 2006. 4 pages. Published in G&P magazine 2006 vol. 6 No. 3 pp. 20-26.
Chen et al. Restricted kappa/lambda light chain ratio by flow cytometry in germinal center B cells in Hashimoto thyroiditis. Am J Clin Pathol. 2006;125(1):42-8.
Cheung, et al. Immunohistochemical diagnosis of papillary thyroid carcinoma. Mod Pathol. Apr. 2001;14(4):338-42.
Chevillard et al. Gene expression profiling of differentiated thyroid neoplasms: diagnostic and clinical implications. Clin Cancer Res. 2004;10(19):6586-97.
Chiappetta et al. The antiapoptotic protein BAG3 is expressed in thyroid carcinomas and modulates apoptosis mediated by tumor necrosis factor-related apoptosis-inducing ligand. J Clin Endocrinol Metab. 2007;92(3):1159-63.
Chudova, et al. Molecular classification of thyroid nodules using high-dimensionality genomic data. J Clin Endocrinol Metab. Dec. 2010;95(12):5296-304. doi: 10.1210/jc.2010-1087. Epub Sep. 8, 2010.
Chung et al. Detection of BRAFV600E mutation on fine needle aspiration specimens of thyroid nodule refines cyto-pathology diagnosis, especially in BRAF600E mutation-prevalent area. Clin Endocrinol (Oxf). 2006;65(5):660-6.
Ciampi et al. BRAF copy number gains in thyroid tumors detected by fluorescence in situ hybridization. Endocr Pathol. 2005;16(2):99-105.
Cibas, et al. The Bethesda System for Reporting Thyroid Cytopathology. Am J Clin Pathol. Nov. 2009;132(5):658-65. doi: 10.1309/AJCPPHLWMI3JV4LA.
Clark et al. Discovery of tissue-specific exons using comprehensive human exon microarrays. Genome Biol. 2007;8(4):R64.
Combined search report and examination report dated Oct. 1, 2013 for GB Application No. 1315760.7.
Cooper, et al. Management guidelines for patients with thyroid nodules and differentiated thyroid cancer. Thyroid. Feb. 2006;16(2):109-42.
Co-pending U.S. Appl. No. 15/164,217, filed May 25, 2016.
Co-pending U.S. Appl. No. 15/164,220, filed May 25, 2016.
Co-pending U.S. Appl. No. 15/164,230, filed May 25, 2016.
Co-pending U.S. Appl. No. 15/164,241, filed May 25, 2016.
Co-pending U.S. Appl. No. 15/185,960, filed Jun. 17, 2016.
Crescioli et al. Methimazole inhibits CXC chemokine ligand 10 secretion in human thyrocytes. J Endocrinol. 2007;195(1):145-55.
Delellis et al. C-cell hyperplasia. An ultrastructural analysis. Lab Invest. 1977;36(3):237-48.
Derringer, et al. Malignant lymphoma of the thyroid gland: a clinicopathologic study of 108 cases. Am J Surg Pathol. May 2000;24(5):623-39.
Dettori et al. Aneuploidy in oncocytic lesions of the thyroid gland: diffuse accumulation of mitochondria within the cell is associated with trisomy 7 and progressive numerical chromosomal alterations. Genes Chromosomes Cancer. 2003;38(1):22-31.
Diaz-Uriarte et al. Gene selection and classification of microarray data using random forest. BMC Bioinformatics. 2006;7:3.
Druckenthaner et al. Evidence for Somatostatin receptor 2 in thyroid tissue. Regul Pept. 2007;138(1):32-9.
Durand et al. Evaluation of gene expression profiles in thyroid nodule biopsy material to diagnose thyroid cancer. J Clin Endocrinol Metab. 2008;93(4):1195-202.
Erdogan et al. The prevalence of RET/PTC mutations in papillary thyroid cancers in Turkish population and its relation between tumor histopathology and prognostic factors. Exp Clin Endocrinol Diabetes. 2008;116(4):225-30.
Esperante, et al. Identification and characterization of four PAX8 rare sequence variants (p. T225M, p. L233L, p. G336S and p. A439A) in patients with congenital hypothyroidism and dysgenetic thyroid glands. Clin Endocrinol (Oxf). May. 2008;68(5):828-35.
Eszlinger et al. Gene expression analysis reveals evidence for inactivation of the TGF-beta signaling cascade in autonomously functioning thyroid nodules. Oncogene. 2004;23(3):795-804.
Eszlinger et al. Meta- and reanalysis of gene expression profiles of hot and cold thyroid nodules and papillary thyroid carcinoma for gene groups. J Clin Endocrinol Metab. 2006;91(5):1934-42.
Eszlinger et al. Perspectives and limitations of microarray-based gene expression profiling of thyroid tumors. Endocr Rev. 2007;28(3):322-38.
Eszlinger, et al. Perspectives for Improved and More Accurate Classification of Thyroid Epithelial Tumors. J Clin Endocrinol Metab. Sep. 2008;93(9):3286-94. Epub Jul. 1, 2008.
European search report and opinion dated Mar. 5, 2014 for EP Application No. 11781242.0.
European search report and opinion dated Apr. 28, 2016 for EP 16153243.7.
European search report and search opinion dated Jan. 28, 2013 for Application No. 10772919.6.
European search report and search opinion dated Nov. 27, 2012 for Application No. 09826462.5.
Ferrari, et al. An approach to estimate between- and within-group correlation coefficients in multicenter studies: plasma carotenoids as biomarkers of intake of fruits and vegetables. Am J Epidemiol. Sep. 15, 2005;162(6):591-8. Epub Aug. 10, 2005.

(56) References Cited

OTHER PUBLICATIONS

Finley et al. Advancing the molecular diagnosis of thyroid nodules: defining benign lesions by molecular profiling. Thyroid. 2005;15(6):562-8.
Finley et al. Discrimination of benign and malignant thyroid nodules by molecular profiling. Ann Surg. 2004;240(3):425-36; discussion 436-7.
Finley et al. Molecular analysis of Hurthle cell neoplasms by gene profiling. Surgery. 2004;136(6):1160-8.
Finley et al. Molecular profiling distinguishes papillary carcinoma from benign thyroid nodules. J Clin Endocrinol Metab. 2004;89(7):3214-23.
Finn, et al. Expression microarray analysis of papillary thyroid carcinoma and benign thyroid tissue: emphasis on the follicular variant and potential markers of malignancy. Virchows Arch. Mar. 2007;450(3):249-60.
Fishel, et al. Meta-analysis of gene expression data: a predictor-based approach. Bioinformatics. Jul. 1, 2007;23(13):1599-606. Epub Apr. 26, 2007.
Fontaine et al. Microarray analysis refines classification of non-medullary thyroid tumours of uncertain malignancy. Oncogene. 2008;27(15):2228-36.
Fryknas et al. Molecular markers for discrimination of benign and malignant follicular thyroid tumors. Tumour Biol. 2006;27(4):211-20.
Fujarewicz, et al. A multi-gene approach to differentiate papillary thyroid carcinoma from benign lesions: gene selection using support vector machines with bootstrapping. Endocr Relat Cancer. Sep. 2007;14(3):809-26.
Garcia-Lopez et al. Thyrocytes from autoimmune thyroid disorders produce the chemokines IP-10 and Mig and attract CXCR3+ lymphocytes. J Clin Endocrinol Metab. 2001;86(10):5008-16.
Gardina et al. Alternative splicing and differential gene expression in colon cancer detected by a whole genome exon array. BMC Genomics. 2006;7:325.
"Gene Annot Website. Array Probesets for HOMER2, printed Jan. 2016."
GeneAnnot website. Probesets for AKT1. Printed Aug. 30, 2016. 1 page.
GeneAnnot website. Probesets for ALK. Printed Aug. 30, 2016. 1 page.
GeneAnnot website. Probesets for BRAF. Printed Aug. 30, 2016. 1 page.
GeneAnnot website. Probesets for CALCA. Printed Aug. 30, 2016. 1 page.
GeneAnnot website. Probesets for CTNNB1. Printed Aug. 30, 2016. 1 page.
GeneAnnot website. Probesets for EIF1AY. Printed Aug. 30, 2016. 1 page.
GeneAnnot website. Probesets for IGF2BP2. Printed Aug. 30, 2016. 1 page.
GeneAnnot website. Probesets for KRT7. Printed Aug. 30, 2016. 1 page.
GeneAnnot website. Probesets for MET. Printed Aug. 30, 2016. 1 page.
GeneAnnot website. Probesets for NTRK2. Printed Aug. 30, 2016. 1 page.
GeneAnnot website. Probesets for NTRK3. Printed Aug. 30, 2016. 2 pages.
GeneAnnot website. Probesets for PIK3CA. Printed Aug. 30, 2016. 1 page.
GeneAnnot website. Probesets for PPARGC1A. Printed Aug. 30, 2016. 1 page.
GeneAnnot website. Probesets for PTEN. Printed Aug. 30, 2016. 2 pages.
GeneAnnot website. Probesets for PTH. Printed Aug. 30, 2016. 1 page.
GeneAnnot website. Probesets for RASA1. Printed Aug. 30, 2016. 1 page.
GeneAnnot website. Probesets for RET. Printed Aug. 30, 2016. 1 page.
GeneAnnot website. Probesets for TP53. Printed Aug. 30, 2016. 1 page.
GeneAnnot website. Probesets for TSHR. Printed Aug. 30, 2016. 1 page.
GeneAnnot website. Probesets for TTF1. Printed Aug. 30, 2016. 1 page.
Giordano et al. Distinct transcriptional profiles of adrenocortical tumors uncovered by DNA microarray analysis. Am J Pathol. 2003;162(2):521-31.
Giordano et al. Organ-specific molecular classification of primary lung, colon, and ovarian adenocarcinomas using gene expression profiles. Am J Pathol. 2001;159(4):1231-8.
Giordano. Genome-wide studies in thyroid neoplasia. Endocrinol Metab Clin North Am. 2008;37(2):311-31, vii-viii.
Gombos, et al. Characterization of microarray gene expression profiles of early stage thyroid tumours. Cancer Genomics Proteomics. Nov.-Dec. 2007;4(6):403-9.
Gonzalez-Campora et al. Blood group antigens in differentiated thyroid neoplasms. Arch Pathol Lab Med. 1998;122(11):957-65.
Greenbaum, et al. Comparing protein abundance and mRNA expression levels on a genomic scale. Genome Biol. 2003;4(9):117. Epub Aug. 29, 2003.
Greenbaum, et al. Interrelating different types of genomic data, from proteome to secretome: 'oming in on function. Genome Res. Sep. 2001;11(9):1463-8.
Griffith et al. Meta-analysis and meta-review of thyroid cancer gene expression profiling studies identifies important diagnostic biomarkers. J Clin Oncol. 2006;24(31):5043-51.
Hadd, et al. Targeted, high-depth, next-generation sequencing of cancer genes in formalin-fixed, paraffin-embedded and fine-needle aspiration tumor specimens. J Mol Diagn. Mar. 2013;15(2):234-47. doi: 10.1016/j.jmoldx.2012.11.006. Epub Jan. 13, 2013.
Hartigan, et al. The dip test of unimodality. Annals of Statistics. 1985; 13(1):70-84.
Haugen, et al. Development of a novel molecular classifier to accurately identify benign thyroid nodules in patients with indeterminate FNA cytology. Abstract presented at 14th International Thyroid Congress. Sep. 15, 2010.
Haugen et al. Increased expression of genes encoding mitochondrial proteins in papillary thyroid carcinomas. Thyroid. 2003;13(7):613-20.
Hawthorn, et al. TIMP1 and SERPIN-A overexpression and TFF3 and CRABP1 underexpression as biomarkers for papillary thyroid carcinoma. Head Neck. Dec. 2004;26(12):1069-83.
Hellwig, et al. Comparison of scores for bimodality of gene expression distributions and genome-wide evaluation of the prognostic relevance of high-scoring genes. BMC Bioinformatics. May 25, 2010;11:276. doi: 10.1186/1471-2105-11-276.
Hemmer, et al. DNA copy number changes in thyroid carcinoma. Am J Pathol. May 1999;154(5):1539-47.
Heuer et al. Different cytokine mRNA profiles in Graves' disease, Hashimoto's thyroiditis, and nonautoimmune thyroid disorders determined by quantitative reverse transcriptase polymerase chain reaction (RT-PCR). Thyroid. 1996;6(2):97-106.
Hoshikawa, et al. Hypoxia induces different genes in the lungs of rats compared with mice. Physiol Genomics. Feb. 6, 2003;12(3):209-19.
Hou et al. Genetic alterations and their relationship in the phosphatidylinositol 3-kinase/Akt pathway in thyroid cancer. Clin Cancer Res. 2007;13(4):1161-70.
Huang et al. A genome-wide approach to identify genetic variants that contribute to etoposide-induced cytotoxicity. Proc Natl Acad Sci USA. 2007;104(23):9758-63.
Huang et al. Gene expression in papillary thyroid carcinoma reveals highly consistent profiles. Proc Natl Acad Sci USA. 2001;98(26):15044-9.
Hunt, et al. A microdissection and molecular genotyping assay to confirm the identity of tissue floaters in paraffin-embedded tissue blocks Arch Pathol Lab Med. 2003; 127(2):213-217.
International search report and written opinion dated Jan. 19, 2012 for PCT Application No. US2011/36143.

(56) References Cited

OTHER PUBLICATIONS

International search report and written opinion dated Feb. 25, 2011 for PCT Application No. US2010/034140.
International search report and written opinion dated Feb. 25, 2013 for PCT Application No. US2012/068804.
International search report and written opinion dated Apr. 17, 2015 for PCT/US2014/026411.
International search report and written opinion dated May 8, 2013 for PCT Application No. US2012/068587.
International search report dated Jul. 29, 2010 for PCT Application No. US2009/06162.
Irizarry, et al. Exploration, normalization, and summaries of high density oligonucleotide array probe level data. Biostatistics. Apr. 2003;4(2):249-64.
Ito, et al. Distant and lymph node metastases of thyroid nodules with no pathological evidence of malignancy: a limitation of pathological examination. Endocr J. Oct. 2008;55(5):889-94. Epub Jun. 14, 2008.
Jacques et al. Two-step differential expression analysis reveals a new set of genes involved in thyroid oncocytic tumors. J Clin Endocrinol Metab. 2005;90(4):2314-20.
Jarzab et al. Gene Expression Profile of Papillary Thyroid Cancer: Sources of Variability and Diagnostic Implications. Cancer Res. 2005;65(4):1587-1597.
Joseph et al. Lack of mutations in the thyroid hormone receptor (TR) alpha and beta genes but frequent hypermethylation of the TRbeta gene in differentiated thyroid tumors. J Clin Endocrinol Metab. 2007;92(12):4766-70.
Jovanovic et al. Most multifocal papillary thyroid carcinomas acquire genetic and morphotype diversity through subclonal evolution following the intra-glandular spread of the initial neoplastic clone. J Pathol. 2008;215(2):145-54.
Kapadia, et al. Malignant lymphoma of the thyroid gland: a clinicopathologic study. Head Neck Surg. Mar.-Apr. 1982;4(4):270-80.
Katoh et al. Thyroid transcription factor-1 in normal, hyperplastic, and neoplastic follicular thyroid cells examined by immunohistochemistry and nonradioactive in situ hybridization. Mod Pathol. 2000;13(5):570-6.
Kebebew et al. Diagnostic and extent of disease multigene assay for malignant thyroid neoplasms. Cancer. 2006;106(12):2592-7.
Kebebew et al. Diagnostic and prognostic value of angiogenesis-modulating genes in malignant thyroid neoplasms. Surgery. Dec. 2005;138(6):1102-9; discussion 1109-10.
Kebebew, et al. The prevalence and prognostic value of BRAF mutation in thyroid cancer. Ann Surg. Sep. 2007;246(3):466-70; discussion 470-1.
Krause, et al. Characterisation of DEHAL1 expression in thyroid pathologies. Eur J Endocrinol. Mar. 2007;156(3):295-301.
Krawczak, et al. The mutational spectrum of single base-pair substitutions in mRNA splice junctions of human genes: causes and consequences. Hum Genet. Sep.-Oct. 1992;90(1-2):41-54.
Kreula, et al. Sample size in fine needle aspiration biopsy. Br J Surg. Dec. 1989;76(12):1270-2.
Kristensen, et al. Genetic variation in putative regulatory loci controlling gene expression in breast cancer. Proc Natl Acad Sci U S A. May 16, 2006;103(20):7735-40. Epub May 9, 2006.
Kroese, et al. Genetic tests and their evaluation: can we answer the key questions? Genet Med. Nov.-Dec. 2004;6(6):475-80.
Kwan, et al. Heritability of alternative splicing in the human genome. Genome Res. Aug. 2007;17(8):1210-8.
Lacroix, et al. PAX8 and peroxisome proliferator-activated receptor gamma 1 gene expression status in benign and malignant thyroid tissues. Eur J Endocrinol. Sep. 2004;151(3):367-74.
Lau et al. Thyroid transcription factor-1: a review. Appl Immunohistochem Mol Morphol. 2002;10(2):97-102.
Lima et al. Thyroid Peroxidase and Thyroglobulin Expression in Normal Human Thyroid Glands. Endocr Pathol. 1998;9(1):333-338.

Lin, et al. Thyroid ultrasonography with fine-needle aspiration cytology for the diagnosis of thyroid cancer. J Clin Ultrasound. Mar.-Apr. 1997;25(3):111-8.
Liu et al. Highly prevalent genetic alterations in receptor tyrosine kinases and phosphatidylinositol 3-kinase/akt and mitogen-activated protein kinase pathways in anaplastic and follicular thyroid cancers. J Clin Endocrinol Metab. 2008;93(8):3106-16.
Lubitz et al. 2006;Microarray analysis of thyroid nodule fine-needle aspirates accurately classifies benign and malignant lesions. J Mol Diagn. 8(4):490-8; quiz 528.
Lubitz et al. Molecular analysis of minimally invasive follicular carcinomas by gene profiling. Surgery. 2005;138(6):1042-8; discussion 1048-9.
Lucentini. Gene association studies typically wrong. The Scientist. 2004; 18(24):20.
Machens et al. Genotype-phenotype based surgical concept of hereditary medullary thyroid carcinoma. World J Surg. 2007;31(5):957-68.
Masini-Repiso et al. Ultrastructural localization of thyroid peroxidase, hydrogen peroxide-generating sites, and monoamine oxidase in benign and malignant thyroid diseases. Hum Pathol. 2004; 35(4):436-46.
Mason, et al. Bimodal distribution of RNA expression levels in human skeletal muscle tissue. BMC Genomics. Feb. 7, 2011;12:98. doi: 10.1186/1471-2164-12-98.
Mazzanti, et al. Using gene expression profiling to differentiate benign versus malignant thyroid tumors. Cancer Res. Apr. 15, 2004;64(8):2898-903.
Mitomo et al. Downregulation of miR-138 is associated with overexpression of human telomerase reverse transcriptase protein in human anaplastic thyroid carcinoma cell lines. Cancer Sci. 2008;99(2):280-6.
Mizukami, et al. Late bone metastasis from an encapsulated follicular carcinoma of the thyroid without capsular and vascular invasion. Pathol Int. 1996 Jun;46(6):457-61.
Montero-Conde et al. Molecular profiling related to poor prognosis in thyroid carcinoma. Combining gene expression data and biological information. Oncogene. 2008;27(11):1554-61.
Moreno, et al. Mutations in the iodotyrosine deiodinase gene and hypothyroidism. N Engl J Med. Apr. 24, 2008;358(17):1811-8. doi: 10.1056/NEJMoa0706819.
Murphy et al. Identification of immunohistochemical biomarkers for papillary thyroid carcinoma using gene expression profiling. Hum Pathol. 2008;39(3):420-6.
Nakano et al. Apoptosis-induced decrease of intrathyroidal CD4(+)CD25(+) regulatory T cells in autoimmune thyroid diseases. Thyroid. 2007;17(1):25-31.
Nakashima et al. Foci formation of P53-binding protein 1 in thyroid tumors: activation of genomic instability during thyroid carcinogenesis. Int J Cancer. 2008;122(5):1082-8.
Nakashima et al. RET oncogene amplification in thyroid cancer: correlations with radiation-associated and high-grade malignancy. Hum Pathol. 2007;38(4):621-8.
Nakayama et al. High molecular weight caldesmon positive stromal cells in the capsule of thyroid follicular tumours and tumour-like lesions. J Clin Pathol. 2002;55(12):917-20.
Nam, et al. BRAF V600E mutation analysis of thyroid nodules needle aspirates in relation to their ultrasongraphic classification: a potential guide for selection of samples for molecular analysis. Thyroid. Mar. 2010;20(3):273-9. doi: 10.1089/thy.2009.0226.
National Cancer Institute web page: "Common Cancer Types", captured by WayBack machine on Dec. 4, 2011, http://www.cancer.gov/cancertopics/types/commoncancers.
Neonakis et al. Expression of calcitonin and somatostatin peptide and mRNA in medullary thyroid carcinoma. World J Surg. 1994;18(4):588-93.
Nikiforova et al. MicroRNA expression profiling of thyroid tumors: biological significance and diagnostic utility. J Clin Endocrinol Metab. 2008;93(5):1600-8.
Notice of allowance dated Sep. 13, 2016 for U.S. Appl. No. 12/964,666.

(56) References Cited

OTHER PUBLICATIONS

Oerntoft, et al. Genome-wide study of gene copy numbers, transcripts, and protein levels in pairs of non-invasive and invasive human transitional cell carcinomas. Mol Cell Proteomics. Jan. 2002;1(1):37-45.
Office action dated Jan. 5, 2015 for U.S. Appl. No. 14/086,716.
Office action dated Jan. 16, 2013 for U.S. Appl. No. 12/592,065.
Office action dated Jan. 22, 2016 for U.S. Appl. No. 13/708,439.
Office action dated Feb. 4, 2014 for U.S. Appl. No. 13/708,439.
Office action dated Feb. 27, 2015 for U.S. Appl. No. 13/710,134.
Office action dated Mar. 9, 2016 for U.S. Appl. No. 13/589,022.
Office action dated Apr. 6, 2012 for U.S. Appl. No. 12/964,666.
Office action dated Apr. 18, 2013 for U.S. Appl. No. 13/318,751.
Office action dated Apr. 27, 2015 for U.S. Appl. No. 12/964,666.
Office action dated May 8, 2014 for U.S. Appl. No. 13/105,756.
Office action dated May 9, 2016 for U.S. Appl. No. 12/964,666.
Office action dated May 16, 2016 for U.S. Appl. No. 14/153,219.
Office action dated May 27, 2015 for U.S. Appl. No. 13/105,756.
Office action dated Jun. 6, 2012 for U.S. Appl. No. 12/592,065.
Office action dated Jun. 10, 2014 for U.S. Appl. No. 13/708,439.
Office action dated Jun. 20, 2014 for U.S. Appl. No. 12/964,666.
Office action dated Jul. 6, 2011 for U.S. Appl. No. 12/964,666.
Office action dated Jul. 10, 2014 for U.S. Appl. No. 13/589,022.
Office action dated Jul. 26, 2016 for U.S Appl. No. 13/710,134.
Office action dated Jul. 30, 2014 for U.S. Appl. No. 13/710,134.
Office action dated Aug. 10, 2016 for U.S. Appl. No. 14/086,716.
Office action dated Sep. 2, 2015 for U.S. Appl. No. 14/086,716.
Office action dated Sep. 11, 2012 for U.S. Appl. No. 13/318,751.
Office action dated Sep. 19, 2016 for U.S. Appl. No. 15/164,217.
Office action dated Sep. 19, 2016 for U.S. Appl. No. 15/164,220.
Office action dated Sep. 19, 2016 for U.S. Appl. No. 15/164,230.
Office action dated Oct. 17, 2013 for U.S. Appl. No. 13/105,756.
Office action dated Nov. 19, 2015 for U.S. Appl. No. 13/710,134.
Office action dated Nov. 29, 2013 for U.S. Appl. No. 13/710,134.
Office action dated Dec. 17, 2015 for U.S. Appl. No. 13/105,756.
Owens, et al. Metastatic breast carcinoma involving the thyroid gland diagnosed by fine-needle aspiration: a case report. Diagn Cytopathol. Aug. 2005;33(2):110-5.
Pallante et al. MicroRNA deregulation in human thyroid papillary carcinomas. Endocr Relat Cancer. 2006;13(2):497-508.
Pavelic, et al. Molecular genetic alterations of FHIT and p53 genes in benign and malignant thyroid gland lesions. Mutat Res. Jul. 25, 2006;599(1-2):45-57. Epub May 15, 2006.
Phenekos et al. Th1 and Th2 serum cytokine profiles characterize patients with Hashimoto's thyroiditis (Th1) and Graves' disease (Th2). Neuroimmunomodulation. 2004;11(4):209-13.
Pita et al. Gene expression profiling associated with the progression to poorly differentiated thyroid carcinomas. Br J Cancer. 2009;101(10):1782-1791.
Prasad et al. Identification of genes differentially expressed in benign versus malignant thyroid tumors. Clin Cancer Res. 2008;14(11):3327-37.
Puskas, et al. Gene profiling identifies genes specific for well-differentiated epithelial thyroid tumors. Cell Mol Biol (Noisy-le-grand). Sep. 5, 2005;51(2):177-86.
Qian, et al. Renal cell carcinoma metastatic to Hurthle cell adenoma of thyroid. Ann Diagn Pathol. Oct. 2004;8(5):305-8.
Ramzy; Ibrahim., "Clinical cytopathology and aspiration biopsy: Fundamental principles and practice. McGraw Hill Professional, 2001."
Reyes, et al. Identification of kallikrein 7, kallikrein 10 and secreted frizzled-related protein 2 as candidate molecular markers for papillary thyroid carcinoma using microarray analysis. Proc Amer Assoc Cancer Res. 2005, vol. 46, Abstract #38.
Ringel et al. Expression of the sodium iodide symporter and thyroglobulin genes are reduced in papillary thyroid cancer. Mod Pathol. 2001;14(4):289-96.
Robinson; et al., "A comparison of Affymetrix gene expression arrays. BMC bioinformatics 8.1 (2007): 449."
Rodrigues-Serpa, et al. Loss of heterozygosity in follicular and papillary thyroid carcinomas. Cancer Genet Cytogenet. Feb. 2003;141(1):26-31.
Roque, et al. Chromosome imbalances in thyroid follicular neoplasms: a comparison between follicular adenomas and carcinomas. Genes Chromosomes Cancer. Mar. 2003;36(3):292-302.
Roura-Mir et al. Single-cell analysis of intrathyroidal lymphocytes shows differential cytokine expression in Hashimoto's and Graves' disease. Eur J Immunol. 1997;27(12):3290-302.
Saeys, et al. A review of feature selection techniques in bioinformatics. Bioinformatics. Oct. 1, 2007;23(19):2507-17. Epub Aug. 24, 2007.
Saiz et al. Immunohistochemical expression of cyclin D1, E2F-1, and Ki-67 in benign and malignant thyroid lesions. J Pathol. 2002;198(2):157-62.
Salvatore et al. A cell proliferation and chromosomal instability signature in anaplastic thyroid carcinoma. Cancer Res. 2007;67(21):10148-58.
Sambrook; et al., "Molecular Cloning: A Laboratory Manual. Second edition, Cold Spring Harbor Laboratory Press, 1989."
Santarpia et al. Phosphatidylinositol 3-kinase/akt and ras/raf-mitogen-activated protein kinase pathway mutations in anaplastic thyroid cancer. J Clin Endocrinol Metab. 2008;93(1):278-84.
Savagner et al. Defective mitochondrial ATP synthesis in oxyphilic thyroid tumors. J Clin Endocrinol Metab. 2001;86(10):4920-5.
Savagner et al. PGC-1-related coactivator and targets are upregulated in thyroid oncocytoma. Biochem Biophys Res Commun. 2003;310(3):779-84.
Schiff, et al. Epidermal growth factor receptor (EGFR) is overexpressed in anaplastic thyroid cancer, and the EGFR inhibitor gefitinib inhibits the growth of anaplastic thyroid cancer. Clin Cancer Res. Dec. 15, 2004;10(24):8594-602.
Schroeder, et al. The RIN: an RNA integrity number for assigning integrity values to RNA measurements. BMC Mol Biol. Jan. 31, 2006;7:3.
Sheu et al. The C allele of the GNB3 C825T polymorphism of the G protein beta3-subunit is associated with an increased risk for the development of oncocytic thyroid tumours. J Pathol. 2007;211(1):60-6.
Shirasawa, S. Susceptibility genes for the development of autoimmune thyroid disease. Nippon Rinsho. Dec. 2006;64(12):2208-14. (Abstract only).
Shvero et al. Immunohistochemical profile and treatment of uncommon types of thyroid carcinomas. Oncol Rep. 2003;10(6):2075-8.
Singh et al. Screening for genetic aberrations in papillary thyroid cancer by using comparative genomic hybridization. Surgery. 2000;128(6):888-93;discussion 893-4.
Siragusa et al. MUC1 oncoprotein promotes refractoriness to chemotherapy in thyroid cancer cells. Cancer Res. 2007;67(11):5522-30.
Smith et al. Methylation status of genes in papillary thyroid carcinoma. Arch Otolaryngol Head Neck Surg. 2007;133(10):1006-11.
Smyth. Linear models and empirical bayes methods for assessing differential expression in microarray experiments. Stat Appl Genet Mol Biol. 2004;3:Article3. Epub Feb. 12, 2004.
Stanta et al. The biochemical and immunohistochemical profile of thyroid neoplasia. Pathol Annu. 1988;23 Pt 1: 129-57.
Symmans, et al. Total RNA Yield and Microarray Gene Expression Profiles from Fine-Needle Aspiration Biopsy and Core-Needle Biopsy Samples of Breast Carcinoma. 2003; Cancer 97(12): 2960-2971.
Takano et al. Expression of oncofetal fibronectin messenger ribonucleic acid in fibroblasts in the thyroid: a possible cause of false positive results in molecular-based diagnosis of thyroid carcinomas. J Clin Endocrinol Metab. 2000;85(2):765-8.
Takano et al. Preoperative diagnosis of thyroid papillary and anaplastic carcinomas by real-time quantitative reverse transcription-polymerase chain reaction of oncofetal fibronectin messenger RNA. Cancer Res. 1999;59(18):4542-5.
Tamir et al. Expression and development of a functional plasmalemmal 5-hydroxytryptamine transporter by thyroid follicular cells. Endocrinology. 1996;137(10):4475-86.

(56) References Cited

OTHER PUBLICATIONS

Taniguchi et al. Differentiation of follicular thyroid adenoma from carcinoma by means of gene expression profiling with adapter-tagged competitive polymerase chain reaction. Oncology. 2005;69(5):428-35.
Terada. Brain metastasis from thyroid adenomatous nodules or an encapsulated thyroid follicular tumor without capsular and vascular invasion: a case report. Cases J. Jul. 17, 2009;2:7180. doi: 10.4076/1757-1626-2-7180.
Tzen, et al. Is atypical follicular adenoma of the thyroid a preinvasive malignancy? Hum Pathol. Jul. 2003;34(7):666-9.
Ueda, et al. Analysis of PAX8 Gene in Congenital Hypothyroidism Mass Screening Positive Subjects. Folia Endocrinologica Japonica. Mar. 30, 2007, vol. 82, No. 4, P.859. (in Japanese with English translation).
Vasko, et al. Gene expression and functional evidence of epithelial-to-mesenchymal transition in papillary thyroid carcinoma invasion. Proc Natl Acad Sci U S A. Feb. 20, 2007;104(8):2803-8. Epub Feb. 12, 2007.
Visone et al. MicroRNAs (miR)-221 and miR-222, both overexpressed in human thyroid papillary carcinomas, regulate p27Kip1 protein levels and cell cycle. Endocr Relat Cancer. 2007;14(3):791-8.
Visone et al. Specific microRNAs are downregulated in human thyroid anaplastic carcinomas. Oncogene. 2007;26(54):7590-5.
Wattel, et al. Gene expression in thyroid autonomous adenomas provides insight into their physiopathology. Oncogene. Oct. 20, 2014;24(46):6902-16.
Weber et al. A limited set of human MicroRNA is deregulated in follicular thyroid carcinoma. J Clin Endocrinol Metab. 2006;91(9):3584-91. Epub Jul. 5, 2006.
Weber et al. Genetic classification of benign and malignant thyroid follicular neoplasia based on a three-gene combination. J Clin Endocrinol Metab. 2005;90(5):2512-21.
Weber et al. Silencing of the maternally imprinted tumor suppressor ARHI contributes to follicular thyroid carcinogenesis. J Clin Endocrinol Metab. 2005;90(2):1149-55.
Wessagowit, et al. Normal and abnormal mechanisms of gene splicing and relevance to inherited skin diseases. J Dermatol Sci. Nov. 2005;40(2):73-84. Epub Jul. 27, 2005.
Whitehead, et al. Variation in tissue-specific gene expression among natural populations. Genome Biol. 2005;6(2):R13. Epub Jan. 26, 2005.
Wiseman et al. Molecular phenotyping of thyroid tumors identifies a Marker panel for differentiated thyroid cancer diagnosis. Ann Surg Oncol. 2008;15(10):2811-26.
Wreesmann et al. Genome-wide profiling of papillary thyroid cancer identifies MUC1 as an independent prognostic marker. Cancer Res. 2004;64(11):3780-9.
Wu, et al. A comparative study of 200 fine needle aspiration biopsies performed by clinicians and cytopathologists. Laryngoscope. Jul. 2006;116(7):1212-5.
Xu et al. Differential expression of galectin-1 and galectin-3 in thyroid tumors. Potential diagnostic implications. Am J Pathol. 1995;147(3):815-22.
Yano et al. Gene expression profiling identifies platelet-derived growth factor as a diagnostic molecular marker for papillary thyroid carcinoma. Clin Cancer Res. 2004;10(6):2035-43.
Yatabe et al. Epidermal growth factor receptor gene amplification is acquired in association with tumor progression of EGFR-mutated lung cancer. Cancer Res. 2008;68(7):2106-11.
Yeh et al. Differentiated thyroid cancer cell invasion is regulated through epidermal growth factor receptor-dependent activation of matrix metalloproteinase (MMP)-2/gelatinase A. Endocr Relat Cancer. 2006;13(4):1173-83.
Yeh et al. Somatic mitochondrial DNA (mtDNA) mutations in papillary thyroid carcinomas and differential mtDNA sequence variants in cases with thyroid tumours. Oncogene. 2000;19(16):2060-6.
Zhang, et al. Association between single-nucleotide polymorphisms of BRAF and papillary thyroid carcinoma in a Chinese population. Thyroid. Jan. 2013;23(1):38-44. doi: 10.1089/thy.2012.0228.
Zhang et al. Regulation of tumor necrosis factor-related apoptosis-inducing ligand-induced apoptosis by DJ-1 in thyroid cancer cells. Endocr Relat Cancer. 2008;15(2):535-44.
Zhou et al. RET proto-oncogene mutations are restricted to codons 634 and 918 in mainland Chinese families with MEN2A and MEN2B. Clin Endocrinol (Oxf). 2007;67(4):570-6.
Co-pending U.S. Appl. No. 15/618,656, filed Jun. 9, 2017.
GeneAnnot website. Probesets for KRAS. Printed Feb. 7, 2017. 2 pages.
Marsh, et al. Genome-wide copy number imbalances identified in familial and sporadic medullary thyroid carcinoma. J Clin Endocrinol Metab. Apr. 2003;88(4):1866-72.
McCarroll, et al. Integrated detection and population-genetic analysis of SNPs and copy number variation. Nature Genetics 40, 1166-1174 (2008).
Office Action dated Feb. 13, 2017 for U.S. Appl. No. 15/164,241.
Office Action dated Mar. 9, 2017 for U.S. Appl. No. 13/710,134.
Office Action dated Mar. 21, 2017 for U.S. Appl. No. 15/164,217.
Office Action dated Mar. 21, 2017 for U.S. Appl. No. 15/164,230.
Office Action dated Mar. 23, 2017 for U.S. Appl. No. 15/164,220.
Office Action dated Jun. 12, 2017 for U.S. Appl. No. 13/105,756.
Office Action dated Jun. 23, 2017 for U.S. Appl. No. 14/153,219.
Office Action dated Jul. 5, 2017 for U.S. Appl. No. 14/086,716.

ALGORITHMS FOR DISEASE DIAGNOSTICS

CROSS REFERENCE

This application is a continuation of U.S. patent application Ser. No. 12/964,666 filed Dec. 9, 2010, which claims the benefit of priority to U.S. Provisional Application No. 61/285,165, entitled "Algorithms for Disease Diagnostics" filed Dec. 9, 2009, each of which is incorporated herein by reference in its entirety.

BACKGROUND OF THE INVENTION

A genetic disorder is an illness caused by abnormalities in genes or chromosomes. Some diseases, such as cancer, are due in part to genetic disorders. Cancer is the second leading cause of death in the United States and one of the leading causes of mortality worldwide. Nearly 25 million people are currently living with cancer, with 11 million new cases diagnosed each year. Furthermore, as the general population continues to age, cancer will become a bigger and bigger problem. The World Health Organization projects that by the year 2020, global cancer rates will increase by 50%.

Successful treatment of genetic diseases such as cancer starts with early and accurate diagnosis. Current methods of diagnosis include cytological examination of tissue samples taken by biopsy or imaging of tissues and organs for evidence of aberrant cellular proliferation. While these techniques have proven to be both useful and inexpensive, they suffer from a number of drawbacks. First, cytological analysis and imaging techniques for cancer diagnosis often require a subjective assessment to determine the likelihood of malignancy. Second, the increased use of these techniques has lead to a sharp increase in the number of indeterminate results in which no definitive diagnosis can be made. Third, these routine diagnostic methods lack a rigorous method for determining the probability of an accurate diagnosis. Fourth, these techniques may be incapable of detecting a malignant growth at very early stages. Fifth, these techniques do not provide information regarding the basis of the aberrant cellular proliferation.

Many of the newer generation of treatments for cancer, while exhibiting greatly reduced side effects, are specifically targeted to a certain metabolic or signaling pathway, and will only be effective against cancers that are reliant on that pathway. Further, the cost of any treatments can be prohibitive for an individual, insurance provider, or government entity. This cost could be at least partially offset by improved methods that accurately diagnose cancers and the pathways they rely on at early stages. These improved methods would be useful both for preventing unnecessary therapeutic interventions as well as directing treatment.

In the case of thyroid cancer it is estimated that out of the approximately 120,000 thyroid removal surgeries performed each year due to suspected malignancy in the United States, only about 33,000 are necessary. Thus, approximately 90,000 unnecessary surgeries are performed at a cost of $7,000 each. In addition, there are continued treatment costs and complications due to the need for lifelong drug therapy to replace the lost thyroid function. Accordingly, there is an unmet need for newer testing modalities and business practices that improve upon current methods of genetic disease diagnosis.

SUMMARY OF THE INVENTION

In one embodiment, the invention is a method of diagnosing a genetic disorder or cancer comprising the steps of: (a) obtaining a biological sample comprising gene expression products; (b) detecting the gene expression products of the biological sample; (c) comparing to an amount in a control sample, an amount of one or more gene expression products in the biological sample to determine the differential gene expression product level between the biological sample and the control sample; (d) classifying the biological sample by inputting the one or more differential gene expression product levels to a trained algorithm; wherein technical factor variables are removed from data based on differential gene expression product level and normalized prior to and during classification; and (e) identifying the biological sample as positive for a genetic disorder or cancer if the trained algorithm classifies the sample as positive for the genetic disorder or cancer at a specified confidence level.

In another embodiment, the invention is an algorithm for diagnosing a genetic disorder or cancer comprising: (a) determining the level of gene expression products in a biological sample; (b) deriving the composition of cells in the biological sample based on the expression levels of cell-type specific markers in the sample; (c) removing technical variables prior to and during classification of the biological sample; (d) correcting or normalizing the gene product levels determined in step (a) based on the composition of cells determined in step (b); and (e) classifying the biological sample as positive for a genetic disorder or cancer.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

improve classification error rates. Classification error rates using the "Tissue" gene list and classification model to predict on the "FNA" cohort (Panel A). Classification error rates using the "FNA" and "Tissue" gene lists and the FNA classification model to predict on the "FNA" cohort (Panel A). The left panel shows using tissue classifier and top tissue genes and predict on FNA samples (N=49). The right panel shows using FNA (Classification) classifier and top FNA/tissue genes and predict on FNA samples (N=49).

Figure 4:
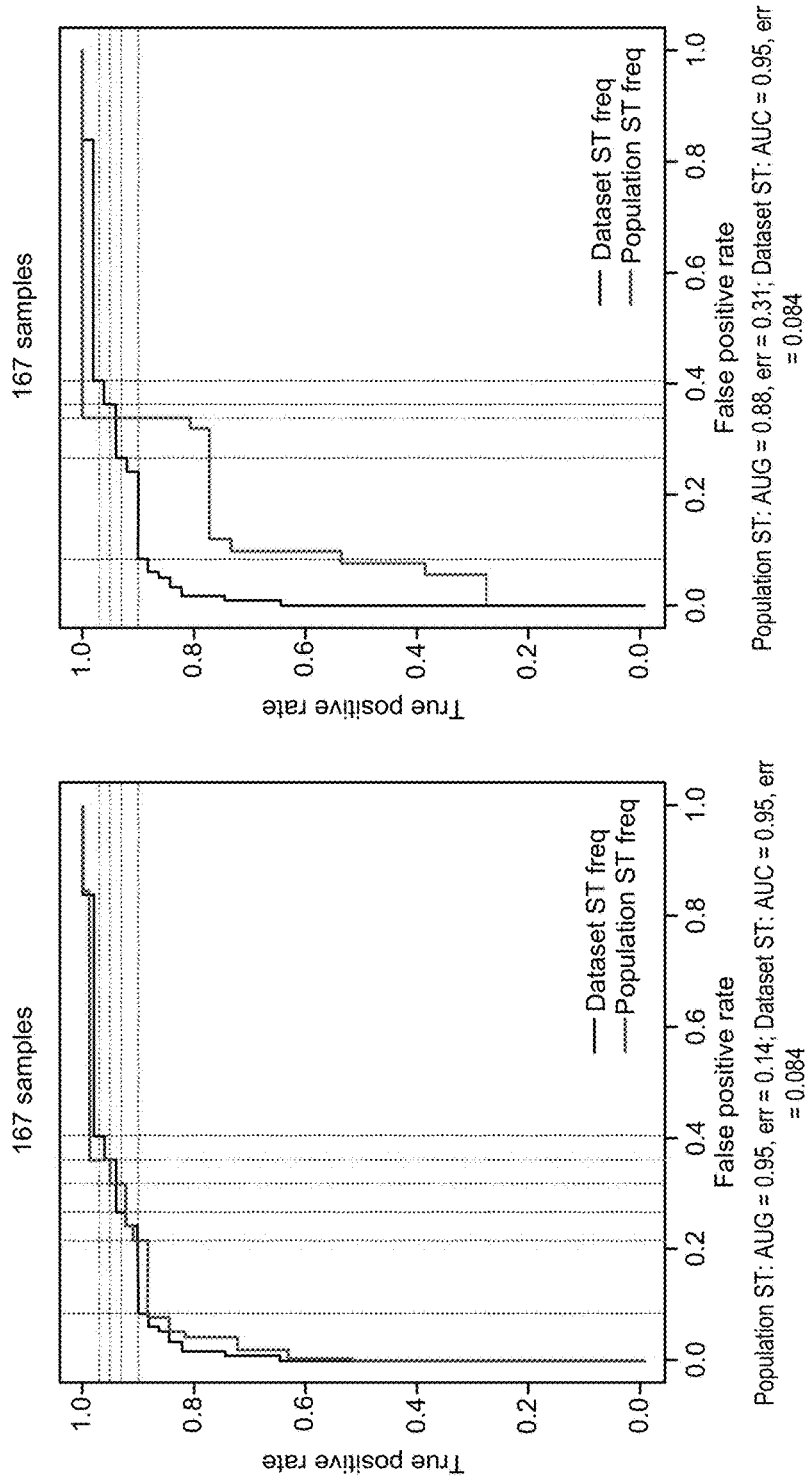

FIG. 4 depicts an honest assessment of classification performance by re-sampling the population to generate a second, subtype specific ROC curve (N=167 FNA samples). The methods currently used in the art (black trace) underestimate classification errors compared to the methods of the present invention (red trace, panel A). This is more evident when the "indeterminate" pathology subtype is probed independently of all others, and re-sampled to generate a second ROC curve of the data (panel B). The present invention improves the accuracy of classification performance calculation methods.

DETAILED DESCRIPTION OF THE INVENTION

The present disclosure provides novel methods for diagnosing genetic disorder or abnormal cellular proliferation from a biological test sample, and related kits and compositions. The present invention also provides methods and compositions for differential diagnosis of types of genetic disorder or aberrant cellular proliferation such as carcinomas, adenomas, benign tumors, malignant tumors, and normal tissues. The present invention further provides algorithms for characterizing and classifying gene expression product markers and novel groups of gene expression product markers useful for the diagnosis, characterization, and treatment of cellular proliferation or genetic disorder. Additionally the present invention provides business methods for providing enhanced diagnosis, differential diagnosis, monitoring, and treatment of cellular proliferation or genetic disorder. In one embodiment, the algorithms of the present invention can be used for diagnosing and monitoring thyroid cancer.

In the present invention, CEL files refer to raw data from an Affymetrix exon array. Electropherogram is used for visualization of the gel image generated by the Bioanalyzer. An exon typically refers to a nucleic acid sequence that is represented in the mature form of an RNA molecule. Exons are protein-coding transcripts that are spliced before being translated. An intron typically refers to a DNA region within a gene that is not translated into protein. Flash frozen paraffin embedded (FFPE)-RNA is known to be fragmented and degraded in such tissue. microRNAs (miRNA) typically refers to single-stranded RNA molecules of 21-23 nucleotides in length, which regulate gene expression. Negative Predictive Value (NPV) is the proportion of patients with negative test results who are correctly diagnosed. Positive predictive value (PPV), or precision rate, or post-test probability of disease, is the proportion of patients with positive test results who are correctly diagnosed. It is one of the most important measures of a diagnostic method as it reflects the probability that a positive test reflects the underlying condition being tested for. Receiver Operator Characteristic Curve (ROC curve) plots sensitivity vs. (1—specificity) for a binary classifier system as its discrimination threshold is varied. Transcriptome typically refers to all mRNA transcripts with a particular cell or tissue. UHR refers to universal human RNA, which can be used as a control material.

I. Genetic Disorder and Aberrant Cell Proliferation

In one aspect, the algorithms and the methods disclosed herein can be used for diagnosis and monitoring of a genetic disorder. A genetic disorder is an illness caused by abnormalities in genes or chromosomes. While some diseases, such as cancer, are due in part to genetic disorders, they can also be caused by environmental factors. In some embodiments, the algorithms and the methods disclosed herein are used for diagnosis and monitoring of a cancer such as thyroid cancer.

Genetic disorders can be typically grouped into two categories: single gene disorders and multifactorial and polygenic (complex) disorders. A single gene disorder is the result of a single mutated gene. There are estimated to be over 4000 human diseases caused by single gene defects. Single gene disorders can be passed on to subsequent generations in several ways. There are several types of inheriting a single gene disorder including but not limited to autosomal dominant, autosomal recessive, X-linked dominant, X-linked recessive, Y-linked and mitochondrial inheritance. Only one mutated copy of the gene will be necessary for a person to be affected by an autosomal dominant disorder. Examples of autosomal dominant type of disorder include but are not limited to Huntington's disease, Neurofibromatosis 1, Marfan Syndrome, Hereditary nonpolyposis colorectal cancer, and Hereditary multiple exostoses. In autosomal recessive disorder, two copies of the gene must be mutated for a person to be affected by an autosomal recessive disorder. Examples of this type of disorder include but are not limited to cystic fibrosis, sickle-cell disease (also partial sickle-cell disease), Tay-Sachs disease, Niemann-Pick disease, spinal muscular atrophy, and dry earwax. X-linked dominant disorders are caused by mutations in genes on the X chromosome. Only a few disorders have this inheritance pattern, with a prime example being X-linked hypophosphatemic rickets. Males and females are both affected in these disorders, with males typically being more severely affected than females. Some X-linked dominant conditions such as Rett syndrome, Incontinentia Pigmenti type 2 and Aicardi Syndrome are usually fatal in males either in utero or shortly after birth, and are therefore predominantly seen in females. X-linked recessive disorders are also caused by mutations in genes on the X chromosome. Examples of this type of disorder include but are not limited to Hemophilia A, Duchenne muscular dystrophy, red-green color blindness, muscular dystrophy and Androgenetic alopecia. Y-linked disorders are caused by mutations on the Y chromosome. Examples include but are not limited to Male Infertility and hypertrichosis pinnae. Mitochondrial inheritance, also known as maternal inheritance, applies to genes in mitochondrial DNA. An example of this type of disorder is Leber's Hereditary Optic Neuropathy.

Genetic disorders may also be complex, multifactorial or polygenic, this means that they are likely associated with the effects of multiple genes in combination with lifestyle and environmental factors. Although complex disorders often cluster in families, they do not have a clear-cut pattern of inheritance. This makes it difficult to determine a person's risk of inheriting or passing on these disorders. Complex disorders are also difficult to study and treat because the specific factors that cause most of these disorders have not yet been identified. Multifactoral or polygenic disorders that can be diagnosed, characterized and/or monitored using the algorithms and methods of the present invention include but are not limited to heart disease, diabetes, asthma, autism, autoimmune diseases such as multiple sclerosis, cancers, ciliopathies, cleft palate, hypertension, inflammatory bowel disease, mental retardation and obesity.

Other genetic disorders that can be diagnosed, characterized and/or monitored using the algorithms and methods of the present invention include but are not limited to 1p36 deletion syndrome, 21-hydroxylase deficiency, 22q11.2 deletion syndrome, 47, XYY syndrome, 48, XXXX, 49, XXXXX, aceruloplasminemia, achondrogenesis, type II, achondroplasia, acute intermittent porphyria, adenylosuccinate lyase deficiency, Adrenoleukodystrophy, ALA deficiency porphyria, ALA dehydratase deficiency, Alexander disease, alkaptonuria, alpha-1 antitrypsin deficiency, Alstrom syndrome, Alzheimer's disease (type 1, 2, 3, and 4), Amelogenesis Imperfecta, amyotrophic lateral sclerosis, Amyotrophic lateral sclerosis type 2, Amyotrophic lateral sclerosis type 4, amyotrophic lateral sclerosis type 4, androgen insensitivity syndrome, Anemia, Angelman syndrome, Apert syndrome, ataxia-telangiectasia, Beare-Stevenson cutis gyrata syndrome, Benjamin syndrome, beta thalassemia, biotinidase deficiency, Birt-Hogg-Dubé syndrome, bladder cancer, Bloom syndrome, Bone diseases, breast cancer, CADASIL, Camptomelic dysplasia, Canavan disease, Cancer, Celiac Disease, CGD Chronic Granulomatous Disorder, Charcot-Marie-Tooth disease, Charcot-Marie-Tooth disease Type 1, Charcot-Marie-Tooth disease Type 4, Charcot-Marie-Tooth disease, type 2, Charcot-Marie-Tooth disease, type 4, Cockayne syndrome, Coffin-Lowry syndrome, collagenopathy, types II and XI, Colorectal Cancer, Congenital absence of the vas deferens, congenital bilateral absence of vas deferens, congenital diabetes, congenital erythropoietic porphyria, Congenital heart disease, congenital hypothyroidism, Connective tissue disease, Cowden syndrome, Cri du chat, Crohn's disease, fibrostenosing, Crouzon syndrome, Crouzonodermoskeletal syndrome, cystic fibrosis, De Grouchy Syndrome, Degenerative nerve diseases, Dent's disease, developmental disabilities, DiGeorge syndrome, Distal spinal muscular atrophy type V, Down syndrome, Dwarfism, Ehlers-Danlos syndrome, Ehlers-Danlos syndrome arthrochalasia type, Ehlers-Danlos syndrome classical type, Ehlers-Danlos syndrome dermatosparaxis type, Ehlers-Danlos syndrome kyphoscoliosis type, vascular type, erythropoietic protoporphyria, Fabry's disease, Facial injuries and disorders, factor V Leiden thrombophilia, familial adenomatous polyposis, familial dysautonomia, fanconi anemia, FG syndrome, fragile X syndrome, Friedreich ataxia, Friedreich's ataxia, G6PD deficiency, galactosemia, Gaucher's disease (type 1, 2, and 3), Genetic brain disorders, Glycine encephalopathy, Haemochromatosis type 2, Haemochromatosis type 4, Harlequin Ichthyosis, Head and brain malformations, Hearing disorders and deafness, Hearing problems in children, hemochromatosis (neonatal, type 2 and type 3), hemophilia, hepatoerythropoietic porphyria, hereditary coproporphyria, Hereditary Multiple Exostoses, hereditary neuropathy with liability to pressure palsies, hereditary nonpolyposis colorectal cancer, homocystinuria, Huntington's disease, Hutchinson Gilford Progeria Syndrome, hyperoxaluria, primary, hyperphenylalaninemia, hypochondrogenesis, hypochondroplasia, idic15, incontinentia pigmenti, Infantile Gaucher disease, infantile-onset ascending hereditary spastic paralysis, Infertility, Jackson-Weiss syndrome, Joubert syndrome, Juvenile Primary Lateral Sclerosis, Kennedy disease, Klinefelter syndrome, Kniest dysplasia, Krabbe disease, Learning disability, Lesch-Nyhan syndrome, Leukodystrophies, Li-Fraumeni syndrome, lipoprotein lipase deficiency, familial, Male genital disorders, Marfan syndrome, McCune-Albright syndrome, McLeod syndrome, Mediterranean fever, familial, MEDNIK, Menkes disease, Menkes syndrome, Metabolic disorders, methemoglobinemia beta-globin type, Methemoglobinemia congenital methaemoglobinaemia, methylmalonic acidemia, Micro syndrome, Microcephaly, Movement disorders, Mowat-Wilson syndrome, Mucopolysaccharidosis (MPS I), Muenke syndrome, Muscular dystrophy, Muscular dystrophy, Duchenne and Becker type, muscular dystrophy, Duchenne and Becker types, myotonic dystrophy, Myotonic dystrophy type 1 and type 2, Neonatal hemochromatosis, neurofibromatosis, neurofibromatosis 1, neurofibromatosis 2, Neurofibromatosis type I, neurofibromatosis type II, Neurologic diseases, Neuromuscular disorders, Niemann-Pick disease, Nonketotic hyperglycinemia, non-syndromic deafness, Nonsyndromic deafness autosomal recessive, Noonan syndrome, osteogenesis imperfecta (type I and type III), otospondylomegaepiphyseal dysplasia, pantothenate kinase-associated neurodegeneration, Patau Syndrome (Trisomy 13), Pendred syndrome, Peutz-Jeghers syndrome, Pfeiffer syndrome, phenylketonuria, porphyria, porphyria cutanea tarda, Prader-Willi syndrome, primary pulmonary hypertension, prion disease, Progeria, propionic acidemia, protein C deficiency, protein S deficiency, pseudo-Gaucher disease, pseudoxanthoma elasticum, Retinal disorders, retinoblastoma, retinoblastoma FA—Friedreich ataxia, Rett syndrome, Rubinstein-Taybi syndrome, SADDAN, Sandhoff disease, sensory and autonomic neuropathy type III, sickle cell anemia, skeletal muscle regeneration, Skin pigmentation disorders, Smith Lemli Opitz Syndrome, Speech and communication disorders, spinal muscular atrophy, spinal-bulbar muscular atrophy, spinocerebellar ataxia, spondyloepimetaphyseal dysplasia, Strudwick type, spondyloepiphyseal dysplasia congenita, Stickler syndrome, Stickler syndrome COL2A1, Tay-Sachs disease, tetrahydrobiopterin deficiency, thanatophoric dysplasia, thiamine-responsive megaloblastic anemia with diabetes mellitus and sensorineural deafness, Thyroid disease, Tourette's Syndrome, Treacher Collins syndrome, triple X syndrome, tuberous sclerosis, Turner syndrome, Usher syndrome, variegate porphyria, von Hippel-Lindau disease, Waardenburg syndrome, Weissenbacher-Zweymüller syndrome, Wilson disease, Wolf-Hirschhorn syndrome, Xeroderma Pigmentosum, X-linked severe combined immunodeficiency, X-linked sideroblastic anemia, and X-linked spinal-bulbar muscle atrophy.

Cancer is a leading cause of death in the United States. Early and accurate diagnosis of cancer is critical for effective management of this disease. It is therefore important to develop testing modalities and business practices to enable cancer diagnosis more accurately, and earlier. Gene expression product profiling, also referred to as molecular profiling, provides a powerful method for early and accurate diagnosis of tumors or other types of cancers from a biological sample.

Typically, screening for the presence of a tumor or other type of cancer, involves analyzing a biological sample taken by various methods such as, for example, a biopsy. The biological sample is then prepared and examined by one skilled in the art. The methods of preparation can include but are not limited to various cytological stains, and immunohistochemical methods. Unfortunately, traditional methods of cancer diagnosis suffer from a number of deficiencies. These deficiencies include: 1) the diagnosis may require a subjective assessment and thus be prone to inaccuracy and lack of reproducibility, 2) the methods may fail to determine the underlying genetic, metabolic or signaling pathways responsible for the resulting pathogenesis, 3) the methods may not provide a quantitative assessment of the test results, and 4) the methods may be unable to provide an unambiguous diagnosis for certain samples.

One hallmark of cancer is dysregulation of normal transcriptional control leading to aberrant expression of genes. Among the aberrantly expressed genes are genes involved in cellular transformation, for example tumor suppressors and oncogenes. Tumor suppressor genes and oncogenes may be up-regulated or down-regulated in tumors when compared to normal tissues. Known tumor suppressors and oncogenes include, but are not limited to brca1, brca2, bcr-abl, bcl-2, HER2, N-myc, C-myc, BRAF, RET, Ras, KIT, Jun, Fos, and p53. This abnormal gene expression may occur through a variety of different mechanisms. It is not necessary in the present invention to understand the mechanism of aberrant gene expression, or the mechanism by which carcinogenesis occurs. Nevertheless, finding a gene or set of genes whose expression is up or down regulated in a sample as compared to a normal sample may be indicative of cancer. Furthermore, the particular aberrantly expressed gene or set of genes may be indicative of a particular type of cancer, or even a recommended treatment protocol. Additionally the methods of the present invention are not meant to be limited solely to canonically defined tumor suppressors or oncogenes. Rather, it is understood that any gene or set of genes that is determined to have a statistically significant correlation with respect to expression level or splicing to a benign, malignant, or normal diagnosis is encompassed by the present invention.

In one embodiment, the methods of the present invention seek to improve upon the accuracy of current methods of cancer diagnosis. Improved accuracy may result from the measurement of multiple gene expression markers, the identification of gene expression products with high diagnostic power or statistical significance, or the identification of groups of gene expression products with high diagnostic power or statistical significance, or any combination thereof.

For example, increased expression of a number of receptor tyrosine kinases has been implicated in carcinogenesis. Measurement of the gene expression product level of a particular receptor tyrosine kinase known to be differentially expressed in cancer cells may provide incorrect diagnostic results leading to a low accuracy rate. Measurement of a plurality of receptor tyrosine kinases may increase the accuracy level by requiring a combination of alternatively expressed genes to occur. In some cases, measurement of a plurality of genes might therefore increase the accuracy of a diagnosis by reducing the likelihood that a sample may exhibit an aberrant gene expression profile by random chance.

Similarly, some gene expression products within a group such as receptor tyrosine kinases may be indicative of a disease or condition when their expression levels are higher or lower than normal. The measurement of expression levels of other gene products within that same group may, however, provide no diagnostic utility. Therefore, it would be advantageous to measure the expression levels of sets of genes that accurately indicate the presence or absence of cancer from within a given group.

Additionally, increased expression of other oncogenes such as for example Ras in a biological sample may also be indicative of the presence of cancerous cells. In some cases, it may be advantageous to determine the expression level of several different classes of oncogenes such as for example receptor tyrosine kinases, cytoplasmic tyrosine kinases, GTPases, serine/threonine kinases, lipid kinases, mitogens, growth factors, and transcription factors. The determination of expression levels and/or exon usage of different classes or groups of genes involved in cancer progression may in some cases increase the diagnostic power of the present invention.

Groups of gene expression markers may include markers within a metabolic or signaling pathway, or genetically or functionally homologous markers. For example, one group of markers may include genes involved in the epithelial growth factor signaling pathway. Another group of markers may include mitogen-activated protein kinases. The present invention also provides methods and compositions for detecting (i.e. measuring) and classifying gene expression markers from multiple and/or independent metabolic or signaling pathways.

In one embodiment, gene expression product markers of the present invention may provide increased accuracy of genetic disorder or cancer diagnosis through the use of multiple gene expression product markers in low quantity and quality, and statistical analysis using the algorithms of the present invention. In particular, the present invention provides, but is not limited to, methods of diagnosing, characterizing and classifying gene expression profiles associated with thyroid cancers. The present invention also provides algorithms for characterizing and classifying thyroid tissue samples, and kits and compositions useful for the application of said methods. The disclosure further includes methods for running a molecular profiling business.

In one embodiment, the subject methods and algorithm are used to diagnose, characterize, and monitor thyroid cancer. Other types of cancer that can be diagnosed, characterized and/or monitored using the algorithms and methods of the present invention include but are not limited to adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's disease, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, uterine cancer (e.g. uterine sarcoma), vaginal cancer, vulvar cancer, and Waldenstrom's macroglobulinemia.

II. Obtaining a Biological Sample

The diagnosis of a genetic disorder or cancer may begin with an examination of a subject by a physician, nurse or other medical professional. As used herein, the term subject refers to any animal (e.g. a mammal), including but not limited to humans, non-human primates, rodents, dogs, pigs, and the like. The examination may be part of a routine examination, or the examination may be due to a specific complaint including but not limited to one of the following:

pain, illness, anticipation of illness, presence of a suspicious lump or mass, a disease, or a condition. The subject may or may not be aware of the disease or condition. The medical professional may obtain a biological sample for testing. In some cases the medical professional may refer the subject to a testing center or laboratory for submission of the biological sample.

In some cases, the subject may be referred to a specialist such as an oncologist, surgeon, or endocrinologist for further diagnosis. The specialist may likewise obtain a biological sample for testing or refer the individual to a testing center or laboratory for submission of the biological sample. In any case, the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample, or the molecular profiling business of the present disclosure may consult on which assays or tests are most appropriately indicated. The molecular profiling business may bill the individual or medical or insurance provider thereof for consulting work, for sample acquisition and or storage, for materials, or for all products and services rendered.

In some embodiments of the present invention, a medical professional need not be involved in the initial diagnosis or sample acquisition. An individual may alternatively obtain a sample through the use of an over the counter kit. Said kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately.

A sample suitable for use by the molecular profiling business may be any material containing tissues, cells, genes, gene fragments, gene expression products, or gene expression product fragments of an individual to be tested. Methods for determining sample suitability and/or adequacy are provided. A sample may include but is not limited to, tissue, cells, or biological material from cells or derived from cells of an individual. The sample may be a heterogeneous or homogeneous population of cells or tissues. In any case, the biological sample may be obtained using any method known to the art that can provide a sample suitable for the analytical methods described herein.

The sample may be obtained by non-invasive methods including but not limited to: scraping of the skin or cervix, swabbing of the cheek, saliva collection, urine collection, feces collection, collection of menses, tears, or semen. In other cases, the sample is obtained by an invasive procedure including but not limited to: biopsy, alveolar or pulmonary lavage, needle aspiration, or phlebotomy. The method of biopsy may further include incisional biopsy, excisional biopsy, punch biopsy, shave biopsy, or skin biopsy. The method of needle aspiration may further include fine needle aspiration, core needle biopsy, vacuum assisted biopsy, or large core biopsy. In some embodiments, multiple samples may be obtained by the methods herein to ensure a sufficient amount of biological material. Methods of obtaining suitable samples of thyroid are known in the art and are further described in the ATA Guidelines for thryoid nodule management (Cooper et al. *Thyroid* Vol. 16 No. 2 2006), herein incorporated by reference in its entirety. Generic methods for obtaining biological samples are also known in the art and further described in for example Ramzy, Ibrahim *Clinical Cytopathology and Aspiration Biopsy* 2001 which is herein incorporated by reference in its entirety. In one embodiment, the sample is a fine needle aspirate of a thyroid nodule or a suspected thyroid tumor. In some cases, the fine needle aspirate sampling procedure may be guided by the use of an ultrasound, X-ray, or other imaging device.

In some embodiments of the present invention, the molecular profiling business may obtain the biological sample from a subject directly, from a medical professional, from a third party, or from a kit provided by the molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

III. Test for Adequacy

Subsequent to or during sample acquisition, the biological material may be collected and assessed for adequacy, for example, to asses the suitability of the sample for use in the methods and compositions of the present invention. The assessment may be performed by the individual who obtains the sample, the molecular profiling business, the individual using a kit, or a third party such as a cytological lab, pathologist, endocrinologist, or a researcher. The sample may be determined to be adequate or inadequate for further analysis due to many factors including but not limited to: insufficient cells, insufficient genetic material, insufficient protein, DNA, or RNA, inappropriate cells for the indicated test, or inappropriate material for the indicated test, age of the sample, manner in which the sample was obtained, or manner in which the sample was stored or transported. Adequacy may be determined using a variety of methods known in the art such as a cell staining procedure, measurement of the number of cells or amount of tissue, measurement of total protein, measurement of nucleic acid, visual examination, microscopic examination, or temperature or pH determination. In one embodiment, sample adequacy will be determined from the results of performing a gene expression product level analysis experiment. In another embodiment sample adequacy will be determined by measuring the content of a marker of sample adequacy. Such markers include elements such as iodine, calcium, magnesium, phosphorous, carbon, nitrogen, sulfur, iron etc.; proteins such as but not limited to thyroglobulin; cellular mass; and cellular components such as protein, nucleic acid, lipid, or carbohydrate.

In some cases, iodine may be measured by a chemical method such as described in U.S. Pat. No. 3,645,691 which is incorporated herein by reference in its entirety or other chemical methods known in the art for measuring iodine content. Chemical methods for iodine measurement include but are not limited to methods based on the Sandell and Kolthoff reaction. Said reaction proceeds according to the following equation:

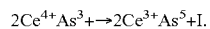

$$2Ce^{4+}As^{3+} \rightarrow 2Ce^{3+}As^{5+}+I.$$

Iodine has a catalytic effect upon the course of the reaction, i.e., the more iodine present in the preparation to be analyzed, the more rapidly the reaction proceeds. The speed of reaction is proportional to the iodine concentration. In some cases, this analytical method may carried out in the following manner:

A predetermined amount of a solution of arsenous oxide $As_2O_3$ in concentrated sulfuric or nitric acid is added to the biological sample and the temperature of the mixture is adjusted to reaction temperature, i.e., usually to a temperature between 20° C. and 60° C. A predetermined amount of a cerium (IV) sulfate solution in sulfuric or nitric acid is added thereto. Thereupon, the mixture is allowed to react at the predetermined temperature for a definite period of time. Said reaction time is selected in accordance with the order of magnitude of the amount of iodine to be determined and with the respective selected reaction temperature. The reaction time is usually between about 1 minute and about 40 minutes. Thereafter, the content of the test solution of cerium (IV) ions is determined photometrically. The lower the photometrically determined cerium (IV) ion concentration is, the higher is the speed of reaction and, consequently, the amount of catalytic agent, i.e., of iodine. In this manner the iodine of the sample can directly and quantitatively be determined.

In other cases, iodine content of a sample of thyroid tissue may be measured by detecting a specific isotope of iodine such as for example $^{123}$I, $^{124}$I, $^{125}$I, and $^{131}$I. In still other cases, the marker may be another radioisotope such as an isotope of carbon, nitrogen, sulfur, oxygen, iron, phosphorous, or hydrogen. The radioisotope in some instances may be administered prior to sample collection. Methods of radioisotope administration suitable for adequacy testing are well known in the art and include injection into a vein or artery, or by ingestion. A suitable period of time between administration of the isotope and acquisition of thyroid nodule sample so as to effect absorption of a portion of the isotope into the thyroid tissue may include any period of time between about a minute and a few days or about one week including about 1 minute, 2 minutes, 5 minutes, 10 minutes, 15 minutes, ½ an hour, an hour, 8 hours, 12 hours, 24 hours, 48 hours, 72 hours, or about one, one and a half, or two weeks, and may readily be determined by one skilled in the art. Alternatively, samples may be measured for natural levels of isotopes such as radioisotopes of iodine, calcium, magnesium, carbon, nitrogen, sulfur, oxygen, iron, phosphorous, or hydrogen.

(i) Cell and/or Tissue Content Adequacy Test

Methods for determining the amount of a tissue include but are not limited to weighing the sample or measuring the volume of sample. Methods for determining the amount of cells include but are not limited to counting cells which may in some cases be performed after dis-aggregation with for example an enzyme such as trypsin or collagenase or by physical means such as using a tissue homogenizer for example. Alternative methods for determining the amount of cells recovered include but are not limited to quantification of dyes that bind to cellular material, or measurement of the volume of cell pellet obtained following centrifugation. Methods for determining that an adequate number of a specific type of cell is present include PCR, Q-PCR, RT-PCR, immuno-histochemical analysis, cytological analysis, microscopic, and or visual analysis.

(ii) Nucleic Acid Content Adequacy Test

Samples may be analyzed by determining nucleic acid content after extraction from the biological sample using a variety of methods known to the art. In some cases, RNA or mRNA is extracted from other nucleic acids prior to nucleic acid content analysis. Nucleic acid content may be extracted, purified, and measured by ultraviolet absorbance, including but not limited to aborbance at 260 nanometers using a spectrophotometer. In other cases nucleic acid content or adequacy may be measured by fluorometer after contacting the sample with a stain. In still other cases, nucleic acid content or adequacy may be measured after electrophoresis, or using an instrument such as an agilent bioanalyzer for example. It is understood that the methods of the present invention are not limited to a specific method for measuring nucleic acid content and or integrity.

In some embodiments, the RNA quantity or yield from a given sample is measured shortly after purification using a NanoDrop spectrophotometer in a range of nano- to micrograms. In some embodiments, RNA quality is measured using an Agilent 2100 Bioanalyzer instrument, and is characterized by a calculated RNA Integrity Number (RIN, 1-10). The NanoDrop is a cuvette-free spectrophotometer. It uses 1 microleter to measure from 5 ng/µl to 3,000 ng/µl of sample. The key features of NanoDrop include low volume of sample and no cuvette; large dynamic range 5 ng/µl to 3,000 ng/µl; and it allows quantitation of DNA, RNA and proteins. NanoDrop™ 2000c allows for the analysis of 0.5 µl-2.0 µl samples, without the need for cuvettes or capillaries.

RNA quality can be measured by a calculated RNA Integrity Number (RIN). The RNA integrity number (RIN) is an algorithm for assigning integrity values to RNA measurements. The integrity of RNA is a major concern for gene expression studies and traditionally has been evaluated using the 28S to 18S rRNA ratio, a method that has been shown to be inconsistent. The RIN algorithm is applied to electrophoretic RNA measurements and based on a combination of different features that contribute information about the RNA integrity to provide a more robust universal measure. In some embodiments, RNA quality is measured using an Agilent 2100 Bioanalyzer instrument. The protocols for measuring RNA quality are known and available commercially, for example, at Agilent website. Briefly, in the first step, researchers deposit total RNA sample into an RNA Nano LabChip. In the second step, the LabChip is inserted into the Agilent bioanalyzer and let the analysis run, generating a digital electropherogram. In the third step, the new RIN algorithm then analyzes the entire electrophoretic trace of the RNA sample, including the presence or absence of degradation products, to determine sample integrity. Then, The algorithm assigns a 1 to 10 RIN score, where level 10 RNA is completely intact. Because interpretation of the electropherogram is automatic and not subject to individual interpretation, universal and unbiased comparison of samples is enabled and repeatability of experiments is improved. The RIN algorithm was developed using neural networks and adaptive learning in conjunction with a large database of eukaryote total RNA samples, which were obtained mainly from human, rat, and mouse tissues. Advantages of RIN include obtain a numerical assessment of the integrity of RNA; directly comparing RNA samples, e.g. before and after archival, compare integrity of same tissue across different labs; and ensuring repeatability of experiments, e.g. if RIN shows a given value and is suitable for microarray experiments, then the RIN of the same value can always be used for similar experiments given that the same organism/tissue/extraction method is used (Schroeder A, et al. BMC Molecular Biology 2006, 7:3 (2006)).

In some embodiments, RNA quality is measured on a scale of RIN 1 to 10, 10 being highest quality. In one aspect, the present invention provides a method of analyzing gene expression from a sample with an RNA RIN value equal or less than 6.0. In some embodiments, a sample containing RNA with an RIN number of 1.0, 2.0, 3.0, 4.0, 5.0 or 6.0 is analyzed for microarray gene expression using the subject methods and algorithms of the present invention. In some embodiments, the sample is a fine needle aspirate of thyroid tissue. The sample can be degraded with an RIN as low as 2.0.

Determination of gene expression in a given sample is a complex, dynamic, and expensive process. RNA samples with RIN 5.0 are typically not used for multi-gene microarray analysis, and may instead be used only for single-gene RT-PCR and/or TaqMan assays. This dichotomy in the usefulness of RNA according to quality has thus far limited the usefulness of samples and hampered research efforts. The present invention provides methods via which low quality RNA can be used to obtain meaningful multi-gene expression results from samples containing low concentrations of RNA, for example, thyroid FNA samples.

In addition, samples having a low and/or un-measurable RNA concentration by NanoDrop normally deemed inadequate for multi-gene expression profiling can be measured and analyzed using the subject methods and algorithms of the present invention. The most sensitive and "state of the art" apparatus used to measure nucleic acid yield in the laboratory today is the NanoDrop spectrophotometer. Like many quantitative instruments of its kind, the accuracy of a NanoDrop measurement decreases significantly with very low RNA concentration. The minimum amount of RNA necessary for input into a microarray experiment also limits the usefulness of a given sample. In the present invention, a sample containing a very low amount of nucleic acid can be estimated using a combination of the measurements from both the NanoDrop and the Bioanalyzer instruments, thereby optimizing the sample for multi-gene expression assays and analysis.

(iii) Protein Content Adequacy Test

In some cases, protein content in the biological sample may be measured using a variety of methods known to the art, including but not limited to: ultraviolet absorbance at 280 nanometers, cell staining as described herein, or protein staining with for example coomassie blue, or bichichonic acid. In some cases, protein is extracted from the biological sample prior to measurement of the sample. In some cases, multiple tests for adequacy of the sample may be performed in parallel, or one at a time. In some cases, the sample may be divided into aliquots for the purpose of performing multiple diagnostic tests prior to, during, or after assessing adequacy. In some cases, the adequacy test is performed on a small amount of the sample which may or may not be suitable for further diagnostic testing. In other cases, the entire sample is assessed for adequacy. In any case, the test for adequacy may be billed to the subject, medical provider, insurance provider, or government entity.

In some embodiments of the present invention, the sample may be tested for adequacy soon or immediately after collection. In some cases, when the sample adequacy test does not indicate a sufficient amount sample or sample of sufficient quality, additional samples may be taken.

IV. Storing the Sample

It may be advantageous to store samples prior to, during, or after use of the samples by the molecular profiling business. For example, samples may be stored upon acquisition to facilitate transport, or to wait for the results of other analyses. In another embodiment, samples may be stored while awaiting instructions from a physician or other medical professional. In some cases, a portion of the sample may be stored while another portion of said sample is further manipulated. Such manipulations may include but are not limited to molecular profiling, cytological staining, gene or gene expression product extraction, fixation, and examination.

The acquired sample may be placed in a suitable medium, excipient, solution, or container for short term or long term storage. Said storage may require keeping the sample in a refrigerated, or frozen environment. The sample may be quickly frozen prior to storage in a frozen environment. The frozen sample may be contacted with a suitable cryopreservation medium or compound including but not limited to: glycerol, ethylene glycol, sucrose, or glucose. A suitable medium, excipient, or solution may include but is not limited to: hanks salt solution, saline, cellular growth medium, or water. The medium, excipient, or solution may or may not be sterile.

The medium, excipient, or solution may contain preservative agents to maintain the sample in an adequate state for subsequent diagnostics or manipulation, or to prevent coagulation. Said preservatives may include citrate, ethylene diamine tetraacetic acid, sodium azide, or thimersol. The sample may be fixed prior to or during storage by any method known to the art such as using glutaraldehyde, formaldehyde, or methanol. The container may be any container suitable for storage and or transport of the biological sample including but not limited to: a cup, a cup with a lid, a tube, a sterile tube, a vacuum tube, a syringe, a bottle, a microscope slide, or any other suitable container. The container may or may not be sterile. In some cases, the sample may be stored in a commercial preparation suitable for storage of cells for subsequent cytological analysis such as but not limited to Cytyc ThinPrep, SurePath, or Monoprep.

V. Transportation of the Sample

The sample may be transported to the molecular profiling company of the present disclosure in order to perform the analyses described herein. The sample may be transported by the individual from whom the sample derives. Said transportation by the individual may include the individual appearing at the molecular profiling business or a designated sample receiving point and providing a sample. Said providing of the sample may involve any of the techniques of sample acquisition described herein, or the sample may have already have been acquired and stored in a suitable container as described herein. In other cases the sample may be transported to the molecular profiling business using a courier service, the postal service, a shipping service, or any method capable of transporting the sample in a suitable manner. In some cases, the sample may be provided to the molecular profiling business by a third party testing laboratory (e.g. a cytology lab). In other cases, the sample may be provided to the molecular profiling business by the subject's primary care physician, endocrinologist or other medical professional. The cost of transport may be billed to the individual, medical provider, or insurance provider. The molecular profiling business may begin analysis of the sample immediately upon receipt, or may store the sample in any manner described herein. The method of storage may or may not be the same as chosen prior to receipt of the sample by the molecular profiling business.

VI. Analysis of Sample

Upon receipt of the sample by the molecular profiling business, a representative or licensee thereof, a medical professional, researcher, or a third party laboratory or testing center (e.g. a cytology laboratory) the sample may be assayed using a variety of routine analyses known to the art such as cytological assays, and genomic analysis. Such tests may be indicative of cancer, the type of cancer, any other disease or condition, the presence of disease markers, or the absence of cancer, diseases, conditions, or disease markers. The tests may take the form of cytological examination including microscopic examination as described below. The tests may involve the use of one or more cytological stains. The biological material may be manipulated or prepared for the test prior to administration of the test by any suitable method known to the art for biological sample preparation. The specific assay performed may be determined by the molecular profiling company, the physician who ordered the test, or a third party such as a consulting medical professional, cytology laboratory, the subject from whom the sample derives, or an insurance provider. The specific assay may be chosen based on the likelihood of obtaining a definite diagnosis, the cost of the assay, the speed of the assay, or the suitability of the assay to the type of material provided.

The present disclosure provides methods and compositions for improving upon the current state of the art for diagnosing genetic disorders or cancer. In one aspect, the present invention provides methods for performing microarray gene expression analysis with low quantity and quality of polynucleotide, such as DNA or RNA. In some embodiments, the present disclosure describes methods of diagnosing, characterizing and/or monitoring a cancer by analyzing gene expression with low quantity and quality of RNA. In one embodiment, the cancer is thyroid cancer. Thyroid RNA can be obtained from fine needle aspirates (FNA). In some embodiments, gene expression profile is obtained from degraded samples with an RNA RIN value of 9.0, 8.0, 7.0, 6.0, 5.0, 4.0, 3.0, 2.0, 1.0 or less. In particular embodiments, gene expression profile is obtained from a sample with an RIN of equal or less than 6, i.e. 6.0, 5.0, 4.0, 3.0, 2.0, 1.0 or less. Provided by the present invention are methods by which low quality RNA can be used to obtain meaningful gene expression results from samples containing low concentrations of nucleic acid, such as thyroid FNA samples.

Another estimate of sample usefulness is RNA yield, typically measured in nanogram to microgram amounts for gene expression assays. The most sensitive and "state of the art" apparatus used to measure nucleic acid yield in the laboratory today is the NanoDrop spectrophotometer. Like many quantitative instruments of its kind, the accuracy of a NanoDrop measurement decreases significantly with very low RNA concentration. The minimum amount of RNA necessary for input into a microarray experiment also limits the usefulness of a given sample. In some aspects, the present invention solves the low RNA concentration problem by estimating sample input using a combination of the measurements from both the NanoDrop and the Bioanalyzer instruments. Since the quality of data obtained from a gene expression study is dependent on RNA quantity, meaningful gene expression data can be generated from samples having a low or un-measurable RNA concentration as measured by NanoDrop.

The subject methods and algorithms enable: 1) gene expression analysis of samples containing low amount and/or low quality of nucleic acid; 2) a significant reduction of false positives and false negatives, 3) a determination of the underlying genetic, metabolic, or signaling pathways responsible for the resulting pathology, 4) the ability to assign a statistical probability to the accuracy of the diagnosis of genetic disorders, 5) the ability to resolve ambiguous results, and 6) the ability to distinguish between subtypes of cancer.

VII. Cytological Analysis

Samples may be analyzed by cell staining combined with microscopic examination of the cells in the biological sample. Cell staining, or cytological examination, may be performed by a number of methods and suitable reagents known to the art including but not limited to: EA stains, hematoxylin stains, cytostain, papanicolaou stain, eosin, nissl stain, toluidine blue, silver stain, azocarmine stain, neutral red, or janus green. In some cases the cells are fixed and/or permeablized with for example methanol, ethanol, glutaraldehyde or formaldehyde prior to or during the staining procedure. In some cases, the cells are not fixed. In some cases, more than one stain is used in combination. In other cases no stain is used at all. In some cases measurement of nucleic acid content is performed using a staining procedure, for example with ethidium bromide, hematoxylin, nissl stain or any nucleic acid stain known to the art.

In some embodiments of the present invention, cells may be smeared onto a slide by standard methods well known in the art for cytological examination. In other cases, liquid based cytology (LBC) methods may be utilized. In some cases, LBC methods provide for an improved means of cytology slide preparation, more homogenous samples, increased sensitivity and specificity, and improved efficiency of handling of samples. In liquid based cytology methods, biological samples are transferred from the subject to a container or vial containing a liquid cytology preparation solution such as for example Cytyc ThinPrep, SurePath, or Monoprep or any other liquid based cytology preparation solution known in the art. Additionally, the sample may be rinsed from the collection device with liquid cytology preparation solution into the container or vial to ensure substantially quantitative transfer of the sample. The solution containing the biological sample in liquid based cytology preparation solution may then be stored and/or processed by a machine to produce a layer of cells on a glass slide. The sample may further be stained and examined under the microscope in the same way as a conventional cytological preparation.

In some embodiments of the present invention, samples may be analyzed by immuno-histochemical staining. Immuno-histochemical staining provides for the analysis of the presence, location, and distribution of specific molecules or antigens by use of antibodies in a biological sample (e.g. cells or tissues). Antigens may be small molecules, proteins, peptides, nucleic acids or any other molecule capable of being specifically recognized by an antibody. Samples may be analyzed by immuno-histochemical methods with or without a prior fixing and/or permeabilization step. In some cases, the antigen of interest may be detected by contacting the sample with an antibody specific for the antigen and then non-specific binding may be removed by one or more washes. The specifically bound antibodies may then be detected by an antibody detection reagent such as for example a labeled secondary antibody, or a labeled avidin/streptavidin. In some cases, the antigen specific antibody may be labeled directly instead. Suitable labels for immuno-histochemistry include but are not limited to fluorophores such as fluoroscein and rhodamine, enzymes such as alkaline phosphatase and horse radish peroxidase, and radionuclides such as $^{32}P$ and $^{125}I$. Gene product markers that may be detected by immuno-histochemical staining include but are not limited to Her2/Neu, Ras, Rho, EGFR, VEGFR, UbcH10, RET/PTC1, cytokeratin 20, calcitonin, GAL-3, thyroid peroxidase, and thyroglobulin.

(i) Tissue-Type Fingerprinting

In many cases, biological samples such as those provided by the methods of the present invention of may contain several cell types or tissues, including but not limited to thyroid follicular cells, thyroid medullary cells, blood cells (RBCs, WBCs, platelets), smooth muscle cells, ducts, duct cells, basement membrane, lumen, lobules, fatty tissue, skin cells, epithelial cells, and infiltrating macrophages and lymphocytes. In the case of thyroid samples, diagnostic classification of the biological samples may involve for example primarily follicular cells (for cancers derived from the follicular cell such as papillary carcinoma, follicular carcinoma, and anaplastic thyroid carcinoma) and medullary cells (for medullary cancer). Since medullary and anaplastic thyroid cancers are rarely present in thyroid samples classified as indeterminate, the diagnosis of indeterminate biological samples from thyroid biopsies in some cases concerns the distinction of follicular adenoma vs. follicular carcinoma. The gene expression signal of a follicular cell for example may thus be diluted out and possibly confounded by other cell types present in the sample. Similarly diagnosis of biological samples from other tissues or organs often involves diagnosing one or more cell types among the many that may be present in the sample.

In some embodiments, the methods of the present invention provide for an upfront method of determining the cellular make-up of a particular biological sample so that the resulting gene expression signatures can be calibrated against the dilution effect due to the presence of other cell and/or tissue types. In one aspect, this upfront method is an algorithm that uses a combination of known cell and/or tissue specific genes as an upfront mini-classifier for each component of the sample. This algorithm utilizes this molecular fingerprint to pre-classify the samples according to their composition and then apply a correction/normalization factor. This data may in some cases then feed in to a final classification algorithm which would incorporate that information to aid in the final diagnosis.

(ii) Genomic Analysis

In some embodiments, genomic sequence analysis, or genotyping, may be performed on the sample. This genotyping may take the form of mutational analysis such as single nucleotide polymorphism (SNP) analysis, insertion deletion polymorphism (InDel) analysis, variable number of tandem repeat (VNTR) analysis, copy number variation (CNV) analysis or partial or whole genome sequencing. Methods for performing genomic analyses are known to the art and may include high throughput sequencing such as but not limited to those methods described in U.S. Pat. Nos. 7,335,762; 7,323,305; 7,264,929; 7,244,559; 7,211,390; 7,361,488; 7,300,788; and 7,280,922. Methods for performing genomic analyses may also include microarray methods as described hereinafter. In some cases, genomic analysis may be performed in combination with any of the other methods herein. For example, a sample may be obtained, tested for adequacy, and divided into aliquots. One or more aliquots may then be used for cytological analysis of the present invention, one or more may be used for gene expression profiling methods of the present invention, and one or more may be used for genomic analysis. It is further understood the present invention anticipates that one skilled in the art may wish to perform other analyses on the biological sample that are not explicitly provided herein.

(iii) Gene Expression Product Profiling

Gene expression profiling is the measurement of the activity (the expression) of thousands of genes at once, to create a global picture of cellular function. These profiles can, for example, distinguish between cells that are actively dividing, or show how the cells react to a particular treatment. Many experiments of this sort measure an entire genome simultaneously, that is, every gene present in a particular cell. Microarray technology measures the relative activity of previously identified target genes. Sequence based techniques, like serial analysis of gene expression (SAGE, SuperSAGE) are also used for gene expression profiling. SuperSAGE is especially accurate and can measure any active gene, not just a predefined set. In an mRNA or gene expression profiling microarray, the expression levels of thousands of genes are simultaneously monitored to study the effects of certain treatments, diseases, and developmental stages on gene expression. For example, microarray-based gene expression profiling can be used to characterize gene signatures of a genetic disorder disclosed herein, or different cancer types, subtypes of a cancer, and/or cancer stages.

Expression profiling experiments often involve measuring the relative amount of mRNA expressed in two or more experimental conditions. This is because altered levels of a specific sequence of mRNA suggest a changed need for the protein coded for by the mRNA, perhaps indicating a homeostatic response or a pathological condition. For example, if breast cancer cells express higher levels of mRNA associated with a particular transmembrane receptor than normal cells do, it might be that this receptor plays a role in breast cancer. One aspect of the present invention encompasses gene expression profiling as part of an important diagnostic test for genetic disorders and cancers, particularly, thyroid cancer.

In some embodiments, RNA samples with RIN ≤5.0 are typically not used for multi-gene microarray analysis, and may instead be used only for single-gene RT-PCR and/or TaqMan assays. Microarray, RT-PCR and TaqMan assays are standard molecular techniques well known in the relevant art. TaqMan probe-based assays are widely used in real-time PCR including gene expression assays, DNA quantification and SNP genotyping.

In one embodiment, gene expression products related to cancer that are known to the art are profiled. Such gene expression products have been described and include but are not limited to the gene expression products detailed in U.S. Pat. Nos. 7,358,061; 7,319,011; 5,965,360; 6,436,642; and US patent applications 2003/0186248, 2005/0042222, 2003/0190602, 2005/0048533, 2005/0266443, 2006/0035244, 2006/083744, 2006/0088851, 2006/0105360, 2006/0127907, 2007/0020657, 2007/0037186, 2007/0065833, 2007/0161004, 2007/0238119, and 2008/0044824.

It is further anticipated that other gene expression products related to cancer may become known, and that the methods and compositions described herein may include such newly discovered gene expression products.

In some embodiments of the present invention gene expression products are analyzed alternatively or additionally for characteristics other than expression level. For example, gene products may be analyzed for alternative splicing. Alternative splicing, also referred to as alternative exon usage, is the RNA splicing variation mechanism wherein the exons of a primary gene transcript, the pre-mRNA, are separated and reconnected (i.e. spliced) so as to produce alternative mRNA molecules from the same gene. In some cases, these linear combinations then undergo the process of translation where a specific and unique sequence of amino acids is specified by each of the alternative mRNA molecules from the same gene resulting in protein isoforms. Alternative splicing may include incorporating different exons or different sets of exons, retaining certain introns, or using utilizing alternate splice donor and acceptor sites.

In some cases, markers or sets of markers may be identified that exhibit alternative splicing that is diagnostic for benign, malignant or normal samples. Additionally, alternative splicing markers may further provide a diagnosis for the specific type of thyroid cancer (e.g. papillary, follicular, medullary, or anaplastic). Alternative splicing markers diagnostic for malignancy known to the art include those listed in U.S. Pat. No. 6,436,642.

(1) In Vitro Methods of Determining Gene Expression Product Levels

The general methods for determining gene expression product levels are known to the art and may include but are not limited to one or more of the following: additional cytological assays, assays for specific proteins or enzyme activities, assays for specific expression products including protein or RNA or specific RNA splice variants, in situ hybridization, whole or partial genome expression analysis, microarray hybridization assays, SAGE, enzyme linked immuno-absorbance assays, mass-spectrometry, immunohistochemistry, or blotting. Gene expression product levels may be normalized to an internal standard such as total mRNA or the expression level of a particular gene including but not limited to glyceraldehyde 3 phosphate dehydrogenase, or tublin.

In some embodiments of the present invention, gene expression product markers and alternative splicing markers may be determined by microarray analysis using, for example, Affymetrix arrays, cDNA microarrays, oligonucleotide microarrays, spotted microarrays, or other microarray products from Biorad, Agilent, or Eppendorf. Microarrays provide particular advantages because they may contain a large number of genes or alternative splice variants that may be assayed in a single experiment. In some cases, the microarray device may contain the entire human genome or transcriptome or a substantial fraction thereof allowing a comprehensive evaluation of gene expression patterns, genomic sequence, or alternative splicing. Markers may be found using standard molecular biology and microarray analysis techniques as described in Sambrook *Molecular Cloning a Laboratory Manual* 2001 and Baldi, P., and Hatfield, W. G., *DNA Microarrays and Gene Expression* 2002.

Microarray analysis begins with extracting and purifying nucleic acid from a biological sample, (e.g. a biopsy or fine needle aspirate) using methods known to the art. For expression and alternative splicing analysis it may be advantageous to extract and/or purify RNA from DNA. It may further be advantageous to extract and/or purify mRNA from other forms of RNA such as tRNA and rRNA.

Purified nucleic acid may further be labeled with a fluorescent, radionuclide, or chemical label such as biotin or digoxin for example by reverse transcription, PCR, ligation, chemical reaction or other techniques. The labeling can be direct or indirect which may further require a coupling stage. The coupling stage can occur before hybridization, for example, using aminoallyl-UTP and NHS amino-reactive dyes (like cyanine dyes) or after, for example, using biotin and labeled streptavidin. The modified nucleotides (e.g. at a 1 aaUTP:4 TTP ratio) are added enzymatically at a lower rate compared to normal nucleotides, typically resulting in 1 every 60 bases (measured with a spectrophotometer). The aaDNA may then be purified with, for example, a column or a diafiltration device. The aminoallyl group is an amine group on a long linker attached to the nucleobase, which reacts with a reactive label (e.g. a fluorescent dye).

The labeled samples may then be mixed with a hybridization solution which may contain SDS, SSC, dextran sulfate, a blocking agent (such as COT1 DNA, salmon sperm DNA, calf thymum DNA, PolyA or PolyT), Denhardt's solution, formamine, or a combination thereof. A hybridization probe is a fragment of DNA or RNA of variable length, which is used to detect in DNA or RNA samples the presence of nucleotide sequences (the DNA target) that are complementary to the sequence in the probe. The probe thereby hybridizes to single-stranded nucleic acid (DNA or RNA) whose base sequence allows probe-target base pairing due to complementarity between the probe and target. The labeled probe is first denatured (by heating or under alkaline conditions) into single DNA strands and then hybridized to the target DNA.

To detect hybridization of the probe to its target sequence, the probe is tagged (or labeled) with a molecular marker; commonly used markers are $^{32}$P or Digoxigenin, which is non-radioactive antibody-based marker. DNA sequences or RNA transcripts that have moderate to high sequence similarity to the probe are then detected by visualizing the hybridized probe via autoradiography or other imaging techniques. Detection of sequences with moderate or high similarity depends on how stringent the hybridization conditions were applied—high stringency, such as high hybridization temperature and low salt in hybridization buffers, permits only hybridization between nucleic acid sequences that are highly similar, whereas low stringency, such as lower temperature and high salt, allows hybridization when the sequences are less similar. Hybridization probes used in DNA microarrays refer to DNA covalently attached to an inert surface, such as coated glass slides or gene chips, and to which a mobile cDNA target is hybridized.

This mix may then be denatured by heat or chemical means and added to a port in a microarray. The holes may then be sealed and the microarray hybridized, for example, in a hybridization oven, where the microarray is mixed by rotation, or in a mixer. After an overnight hybridization, non specific binding may be washed off (e.g. with SDS and SSC). The microarray may then be dried and scanned in a special machine where a laser excites the dye and a detector measures its emission. The image may be overlaid with a template grid and the intensities of the features (several pixels make a feature) may be quantified.

Various kits can be used for the amplification of nucleic acid and probe generation of the subject methods. Examples of kit that can be used in the present invention include but are not limited to Nugen WT-Ovation FFPE kit, cDNA amplification kit with Nugen Exon Module and Frag/Label module. The NuGEN WT-Ovation™ FFPE System V2 is a whole transcriptome amplification system that enables conducting global gene expression analysis on the vast archives of small and degraded RNA derived from FFPE samples. The system is comprised of reagents and a protocol required for amplification of as little as 50 ng of total FFPE RNA. The protocol can be used for qPCR, sample archiving, fragmentation, and labeling. The amplified cDNA can be fragmented and labeled in less than two hours for GeneChip® 3' expression array analysis using NuGEN's FL-Ovation™ cDNA Biotin Module V2. For analysis using Affymetrix GeneChip® Exon and Gene ST arrays, the amplified cDNA can be used with the WT-Ovation Exon Module, then fragmented and labeled using the FL-Ovation™ cDNA Biotin Module V2. For analysis on Agilent arrays, the amplified cDNA can be fragmented and labeled using NuGEN's FL-Ovation™ cDNA Fluorescent Module.

In some embodiments, Ambion WT-expression kit can be used. Ambion WT-expression kit allows amplification of total RNA directly without a separate ribosomal RNA (rRNA) depletion step. With the Ambion® WT Expression Kit, samples as small as 50 ng of total RNA can be analyzed on Affymetrix® GeneChip® Human, Mouse, and Rat Exon and Gene 1.0 ST Arrays. In addition to the lower input RNA requirement and high concordance between the Affymetrix® method and TaqMan® real-time PCR data, the Ambion® WT Expression Kit provides a significant increase in sensitivity. For example, a greater number of probe sets detected above background can be obtained at the exon level with the Ambion® WT Expression Kit as a result of an increased signal-to-noise ratio. Ambion WT-expression kit may be used in combination with additional Affymetrix labeling kit.

In some embodiments, AmpTec Trinucleotide Nano mRNA Amplification kit (6299-A15) can be used in the subject methods. The ExpressArt® TRinucleotide mRNA amplification Nano kit is suitable for a wide range, from 1 ng to 700 ng of input total RNA. According to the amount of input total RNA and the required yields of aRNA, it can be used for 1-round (input>300 ng total RNA) or 2-rounds (minimal input amount 1 ng total RNA), with aRNA yields in the range of >10 .mu.g. AmpTec's proprietary TRinucleotide priming technology results in preferential amplification of mRNAs (independent of the universal eukaryotic 3'-poly(A)-sequence), combined with selection against rRNAs. This kit can be used in combination with cDNA conversion kit and Affymetrix labeling kit.

The raw data may then be normalized, for example, by subtracting the background intensity and then dividing the intensities making either the total intensity of the features on each channel equal or the intensities of a reference gene and then the t-value for all the intensities may be calculated. More sophisticated methods include z-ratio, loess and lowess regression and RMA (robust multichip analysis) for Affymetrix chips.

(2) In Vivo Methods of Determining Gene Expression Product Levels

It is further anticipated that the methods and compositions of the present invention may be used to determine gene expression product levels in an individual without first obtaining a sample. For example, gene expression product levels may be determined in vivo, that is in the individual. Methods for determining gene expression product levels in vivo are known to the art and include imaging techniques such as CAT, MRI; NMR; PET; and optical, fluorescence, or biophotonic imaging of protein or RNA levels using antibodies or molecular beacons. Such methods are described in US 2008/0044824, US 2008/0131892, herein incorporated by reference. Additional methods for in vivo molecular profiling are contemplated to be within the scope of the present invention.

(iv) Assay Results

The results of the routine cytological, genomic, and/or molecular profiling assays may indicate a sample as negative (cancer, disease or condition free), ambiguous or suspicious (suggestive of the presence of a cancer, disease or condition), diagnostic (positive diagnosis for a cancer, disease or condition), or non diagnostic (providing inadequate information concerning the presence or absence of cancer, disease, or condition). The diagnostic results may be further classified as malignant or benign. The diagnostic results may also provide a score indicating for example, the severity or grade of a cancer, or the likelihood of an accurate diagnosis. In some cases, the diagnostic results may be indicative of a particular type or stage of a cancer, disease, or condition. The diagnostic results may inform a particular treatment or therapeutic intervention for the type or stage of the specific cancer disease or condition diagnosed. In some embodiments, the results of the assays performed may be entered into a database. The molecular profiling company may bill the individual, insurance provider, medical provider, or government entity for one or more of the following: assays performed, consulting services, reporting of results, database access, or data analysis. In some cases all or some steps other than molecular profiling are performed by a cytological laboratory or a medical professional.

VII. Molecular Profiling with Algorithms

The herein described methods and algorithms can be used as a diagnostic tool for many types of genetic disorders or suspected tumors including for example thyroid tumors or nodules. Samples that assay as negative, indeterminate, diagnostic, or non diagnostic may be subjected to subsequent assays to obtain more information. In the present invention, these subsequent assays comprise the steps of molecular profiling of gene expression product levels or gene expression product alternative splicing. In some embodiments of the present invention, molecular profiling means the determination of the number (i.e. amount) and/or type of gene expression product molecules (i.e. nucleic acid or protein) in a biological sample. In some cases, the number and/or type may further be compared to a control sample or a sample considered to be normal. Molecular profiling may be performed on the same sample, a portion of the same sample, or a new sample may be acquired using any of the methods described herein. The molecular profiling company may request additional sample by directly contacting the individual or through an intermediary such as a physician, third party testing center or laboratory, or a medical professional. In some cases, samples are assayed using methods and compositions of the molecular profiling business in combination with some or all cytological staining or other diagnostic methods. In other cases, samples are directly assayed using the methods and compositions of the molecular profiling business without the previous use of routine cytological staining or other diagnostic methods. In some cases the results of molecular profiling alone or in combination with cytology may enable those skilled in the art to diagnose or suggest treatment for the subject. In some cases, molecular profiling may be used alone or in combination with cytology to monitor tumors or suspected tumors over time for malignant changes.

The goal of algorithm development is to extract biological information from high-dimensional transcription data in order to accurately classify benign vs. malignant biopsies. In some embodiments, disclosed herein is a molecular classifier algorithm, which combines the process of upfront preprocessing of exon data, followed by exploratory analysis, technical factor removal (when necessary), feature (i.e. marker or gene) selection, classification, and finally, performance measurements. Other embodiments also describe the process of cross-validation within and outside the feature selection loop as well as an iterative gene selection method algorithm to combine three analytical methods of marker extraction (tissue, Bayesian, repeatability).

In some embodiments, the present invention comprises 3 distinct phases: first, improve sample collection and nucleic acid extraction in compromised FNA samples; second, collect high-quality genome-wide expression data on an adequate number of samples; and finally, create, train and test an algorithm which could use high-dimensionality data and accurately classify FNAs into a benign or malignant state. Exemplary materials and methods used for each of these three phases are disclosed herein.

In some embodiments, a series of experiments designed to determine feasibility of a molecular thyroid test are performed. The test is aimed at classifying thyroid fine needle aspirates (FNAs) into benign and malignant categories. In one example, a total of 11 major experiments assaying over 690 specimens were designed and executed, all leading to major conclusions or decisions. In some embodiments, the present invention comprises two general categories: assay development and algorithm development. For example, in some embodiments, the following assay parameters can be used:

Selection of RNAProtect as FNA Collection Fluid
Selection of 25 ng as RNA input used for NuGEN amplification
Selection of NuGEN FFPE kit for amplification
Selection of microarray platform for analysis of degraded RNA samples In several embodiments, algorithm training can be conducted on a sample of surgical tissue, FNA's collected in TRIzol, and/or FNAs collected in RNAProtect. In testing of algorithm performance results, results were obtained where approximately 90% non-benign percent agreement (aka sensitivity) and 93% benign agreement (aka specificity) on a select set of samples that pass certain pre- and post-chip metrics.

Training of the algorithm can include feature (ie. Gene) selection. Each round of training can result in a de novo set of markers, for example, 5, 10, 25, 50, 100, 200, 300 or 500 markers. In one example, comparison of marker lists across the three key discovery training sets (surgical tissue, FNA's collected in TRIzol, and FNAs collected in RNAProtect) revealed a total of 338 non-redundant markers; of these 158 markers are in all three marker lists.

In addition to assay and algorithm development, the selection of Affymetrix is based on three criteria: technical feasibility, regulatory readiness and cost of goods estimates.

Platform Selection

The assays used to identify genes in the discovery phase need not be the same assays used to measure genes in the commercial test. For example, microarrays are an effective and comprehensive gene discovery platform. In other cases, markers are identified by real-time quantitative PCR methods such as TaqMan or Lightcycler. Unfortunately, differences in dynamic range, sensitivity and other assay parameters may result in high levels of marker attrition, sometimes as high as 50% loss per iteration. Multiple rounds of gene selection and validation can ensue, with repeated sampling from the original gene discovery pool.

In some embodiments, the present invention provides a method to both discover genes and measure them in clinical assays on the same platform: the microarray. In some embodiments, cost can be reduced by designing a custom microarray with only a portion of the original content, yet with enough extra content to ensure that the markers required for algorithm performance are retained, regardless of marker drop-out. The high parallelism of microarrays allows us to use the same wet laboratory assay to measure 20,000 genes as it does 200. In some embodiments, a NuGEN amplification and Affymetrix detection system can be used together.

The nature of the training set represents the biggest obstacle to the creation of a robust classifier. Often, a given clinical cohort is limited by the prevalence of disease subtypes that are represented, and/or there is no clear phenotypic, biological, and/or molecular distinction between disease subtypes. Theoretically, the training set can be improved by increasing the number and nature of samples in a prospective clinical cohort, however this approach is not always feasible. Joining of multiple datasets to increase the overall size of the cohort used for training the classifier can be accompanied by analytical challenges and experimental bias.

In one aspect, the present invention overcomes limitations in the current art by joining multiple datasets and applying a technical factor removal normalization approach to the datasets either prior to and/or during classification. In another aspect, the present invention provides methods for gene selection. In another aspect, the present invention introduces a novel ROC-based method for obtaining more accurate subtype-specific classification error rates. Multiple datasets belonging to distinct experiments can be combined and analyzed together. This increases the number of samples available for model training and the overall accuracy of the predictive algorithm.

1. Quality Control

Affymetrix Power Tools (APT, version 1.10.2) software can be used to process, normalize and summarize output (post-hybridization) microarray data (.CEL) files. Quantile normalization, detection above background (DABG), and robust multichip average (RMA) determination of AUC can be done using APT, a program that has been written and streamlined for the automatic processing of post-hybridization data. This automated processing script produces a probeset-level intensity matrix and a gene-level intensity matrix. DABG can be computed as the fraction of probes having smaller than p<1e-4 when compared with background probes of the similar GC content (Affymetrix). Accurate classification may be encumbered by a variety of technical factors including failed or suboptimal hybridization. Post-Hybridization QC metrics can be correlated with Pre-Hybridization QC variables to identify the technical factors that may obscure or bias signal intensity.

TABLE 1

Algorithm Nomenclature

| Algorithm | Purpose |
|---|---|
| Classification | An algorithm to classify thyroid samples into benign and nonbenign |
| Combo | An algorithm to combine three analytical methods of marker extraction (LIMMA, LIMMA + Bayesian, LIMMA + Repeatability) |

TABLE 2

List of standard R packages used in the molecular classifier

| Used for: | Package | Built |
|---|---|---|
| mva plots | AffymetrixPLM | 2.7.2 |
| Used for SVM | e1071 | 2.7.2 |
| Used for LASSO logistic regression | glmnet | 2.9.0 |
| Used for GSA analysis | GSA | 2.9.0 |
| Used for various plots | lattice | 2.9.0 |
| Used for gene selection | limma | 2.7.2 |
| Used for margin tree classifier | marginTree | 2.9.0 |
| Used for LDA | MASS | 2.9.0 |
| Used for RF classifier and gene selection | randomForest | 2.7.2 |
| Used for heatmaps | RColorBrewer | 2.7.2 |
| Used for ROC curve visualization | ROCR | 2.8.0 |
| Used for exception handling | R.oo | 2.8.1 |
| Used for diagonal LDA classifier | sfsmisc | 2.8.1 | i. Classification Version

In some embodiments, Classification is used to analyze data in the subject method. The version of the engine used to generate reports at the end of discovery has been tagged as Release-Classification-1.0 in SVN. In one example, the data analyzed by Classification are .CEL files generated from Thyroid Tissue and FNA samples run on Affymetrix Human Exon 1 ST array with NA26 annotations.

In one example, the overall workflow after scanning the microarrays is as follows: output .CEL files→APT Intensity Matrix→pDABG/AUC→remove samples with AUC≤0.73 and DABG≤xPlot→PCAs of each categorical technical factor→Plot variance component as function of each technical factor→Determine if additional samples need to be removed or flagged→Determine if factor needs removal globally or within cross-validation→run classification.

Two common QC metrics used to pass or fail a sample in order to enter it into the molecular classifier are Intron/Exon separation AUC and pDABG or pDET. The threshold for AUC can be, for example, around 0.73. The threshold for pDET (percentage of genes or probe sets that are detected above background) can be adjusted for different data sets as learning continues during marker discovery.

2. Exploratory Analysis

In some embodiments, the present invention utilizes one or more exploratory methods to generate a broad preliminary analysis of the data. These methods are used in order to assess whether technical factors exist in the datasets that may bias downstream analyses. The output from exploratory analyses can be used to flag any suspicious samples, or batch effects. Flagged samples or subsets of samples can then be processed for technical factor removal prior to, and/or during feature selection and classification. Technical factor removal is described in detail in section 3. The methods used for exploratory analyses include but are not limited to:

Principal component analysis (PCA) can be used to assess the effects of various technical factors, such as laboratory processing batches or FNA sample collection media, on the intensity values. To assess the effects of technical factors, the projection of the normalized intensity values to the first few principal components can be visualized in a pair-wise manner, color coded by the values of the technical variable. If a significant number of samples are affected by any given technical factor and the first few principal components show separation according to the factor, this factor can be considered a candidate for computational removal during subsequent phases of analysis.

In addition to PCA visualization, the present invention can utilize analysis of variance (variance components) as a quantitative measure to isolate technical factors that have significant effect on normalized intensity values. Variance decomposition can be achieved by fitting a linear model to the normalized intensity values for each of the genes that passes non-specific filtering criteria. The explanatory variables in the linear model include biological factors as well as technical factors of interest. When categorical technical factors are represented sparsely in the data, combinations of these factors can be explored as explanatory variables in the model to reduce the number of parameters and enable estimation of effect sizes due to individual variables. In one embodiment, once the linear model is fitted for gene n, the omega squared measure ($\omega^2$) is used to provide an unbiased assessment of the effect size for each of the explanatory variables j on the individual gene (Bapat, R. B. (2000). Linear Algebra and Linear Models (Second ed.) Springer):

$$\omega^2 = \frac{(SS_{effect} - df_{effect} * MS_{error})}{(MS_{error} + SS_{total})}$$

Figure 1:
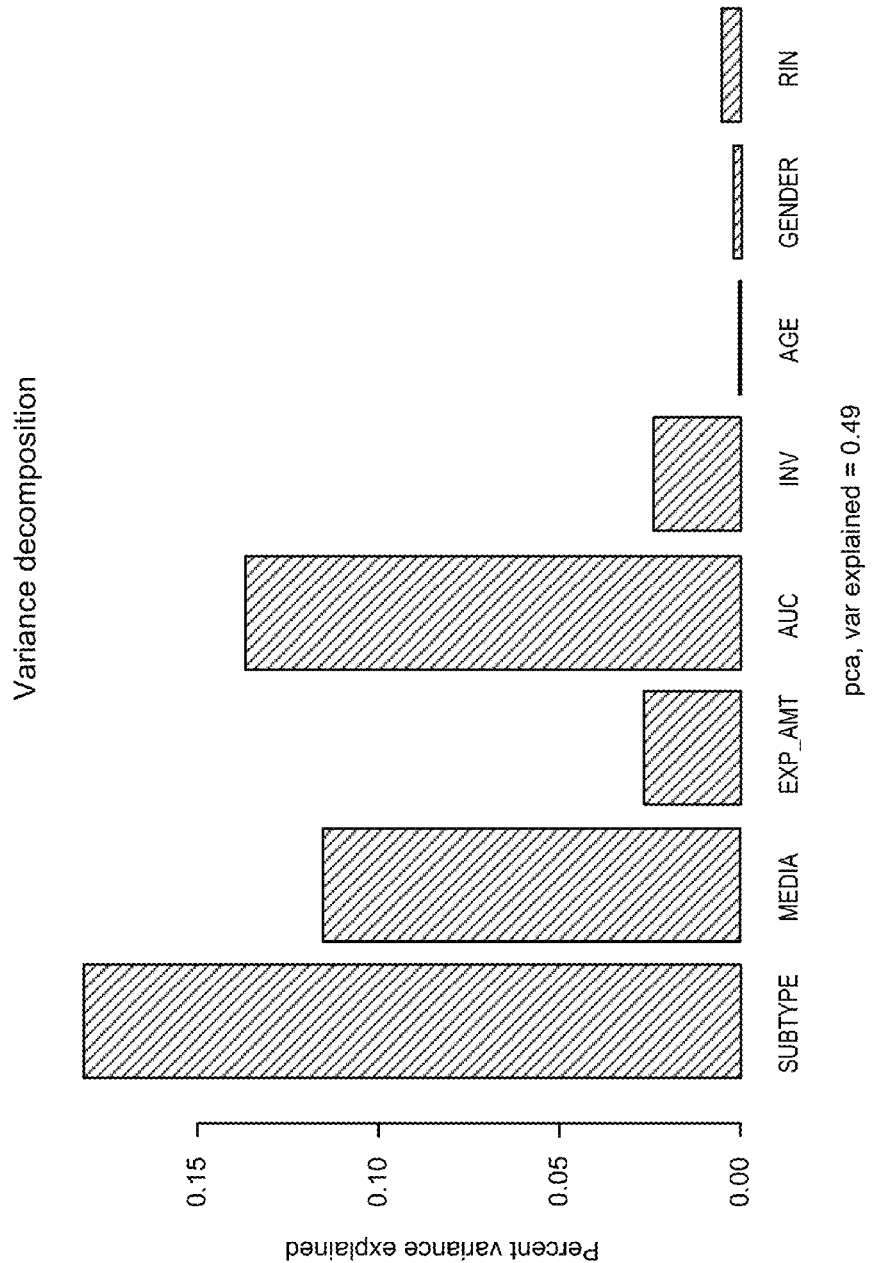
FIG. 1 shows an example of technical factor effects using variance decomposition analysis.
Figure 2:
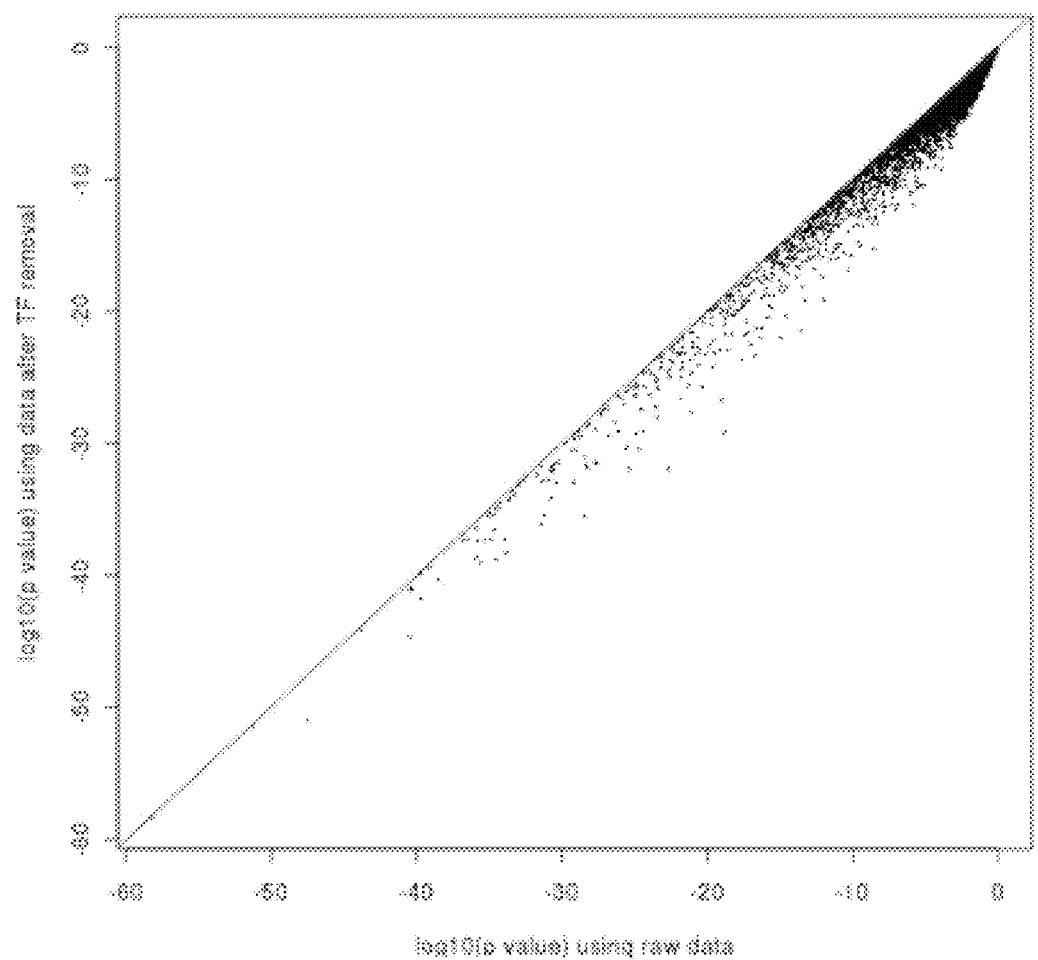
FIG. 2 shows that P-values improve after technical factor removal. In this example the technical factor removed was sample collection fluid. Two chemically distinct fluids were used for sample preservation at the time of collection in the clinic. This technical factor obscured the biological signal present during standard analysis. The 45-degree line in the graph indicates that the p-values calculated from the raw data (log 10 scale) were lower than the p-values calculated after the technical factor removal method was used on the same dataset. P-values become more significant with technical factor removal. Here technical factor is collection fluid. A large number of samples came from another collection fluid and that effect obscures the biological signal present in the markers.
Figure 3:
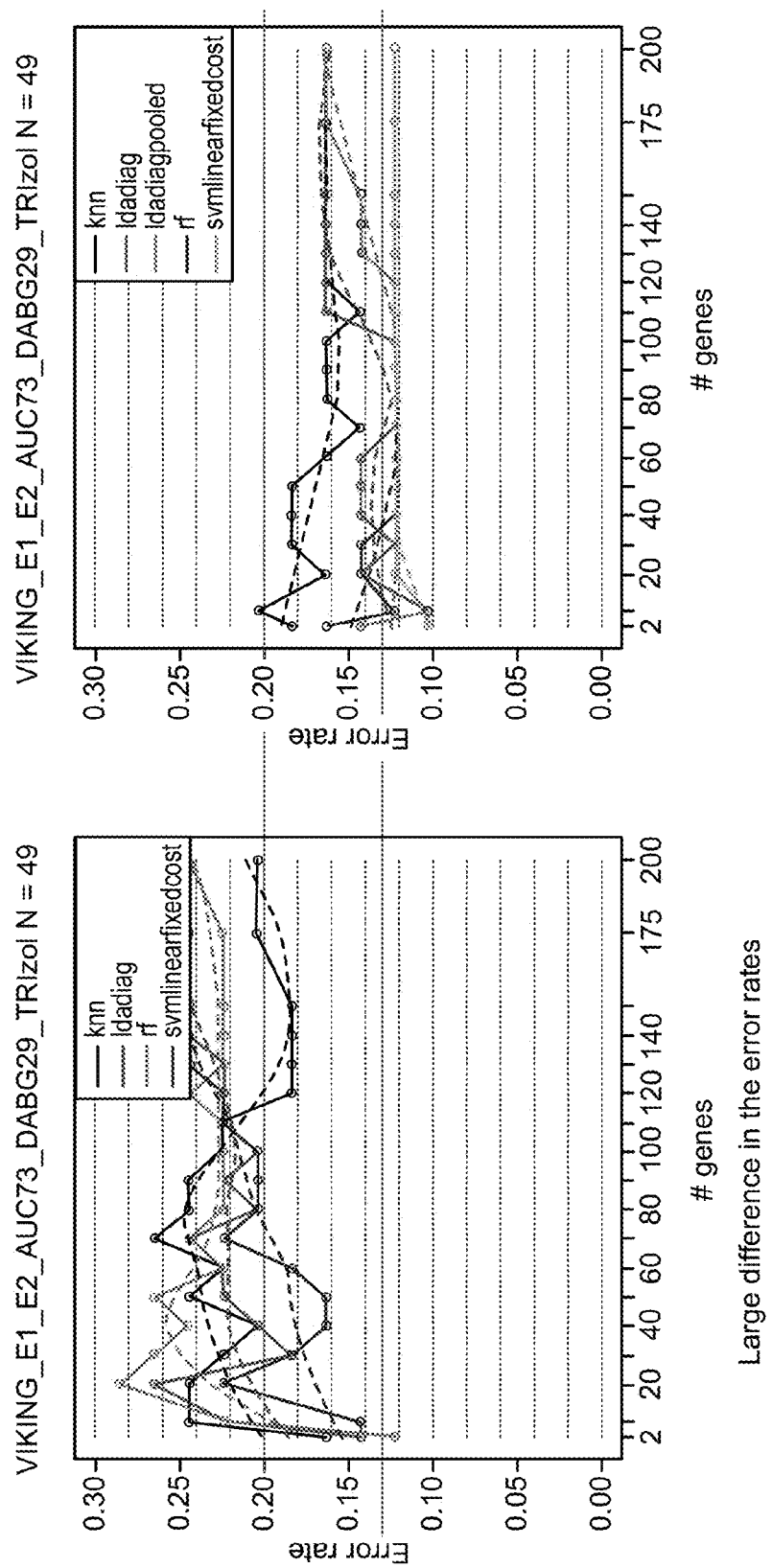
FIG. 3 depicts gene titration curves showing the algorithms of the present invention (Combo and Classification)

Here $SS_{effect}$ is the sum of squares due to the explanatory variable, MS., is the mean squared error, $SS_{total}$ is the total sum of squares, and $df_{effect}$ is the degrees of freedom associated with a particular variable. To assess average effect size across all genes passing non-specific filtering criteria, average values of $\omega^2$ are calculated across all genes and visualized either as raw effect sizes or proportions of total variance explained. FIG. 1 shows an example plot with average effect sizes assessed across one biological factor (pathology class) and three technical factors (one continuous and categorical). Non-biological explanatory variables with effect sizes greater than or comparable to the biological factors are considered candidates for computational removal as technical factors.

3. Technical Factor Removal

PCA and Variance components can be used to assess the magnitude and significance of the technical variability in the data relative to the biological signal. If it was deemed that technical sources of variability must be removed, then the regression method can be used to remove that effect.

(a) Details on the regression method: In a supervised setting, this method can be used to adjust the probe intensities for variation due to technical reasons (e.g. sample collection media) in the presence of the primary variable of interest (the disease label). Adjustments for technical factors can be made both in gene/feature selection, as well as in feature adjustment necessary for correct classification. For example:

(I) Feature Selection Linear Model:

$$E(y) = \beta_0 + \beta_1 BM + \beta_2 TF_1 + \beta_3 BM^* TF_2 + \ldots + \epsilon$$

where TF1 is technical factor 1; and BM is the variable which contains the label 'B' or 'M'. The current call to LIMMA for feature selection would be extended to support the adjustment by technical factors (up to 3) and corresponding 2-way interaction terms with the BM variable, if needed.

Feature Adjustment: The features themselves can be adjusted in the following way:

$$Y - \hat{Y} = X\hat{\beta}$$

where $\hat{\beta}$ are the estimated coefficients from the terms in the feature selection linear model equation which involve technical factors. In some instances, the model matrix will contain only the variables containing the technical factor and will not contain the column of 1's (the intercept term).

In unsupervised correction, the technical factor (TF) covariate can be used to shift the means between samples of one type (e.g., banked FNA) and those of another (e.g., prospective FNA). A boxplot of all the probe intensities for each sample will show whether such a "shift in means" exists due to known factors of technical variation.

In some embodiments, only if the technical source of variability is simply a global "shift in means" or linear and is not confounded by disease subtype then the regression method in an unsupervised setting will be applied. This would be an unsupervised correction, i.e., no disease labels will be used in the correction step.

In some embodiments, if evidence of technical variability is present in the data, but biological signal overwhelms it, no correction is applied to the data sets. A list of co-variables that can be examined by the subject algorithm is shown in Table 3.

TABLE 3

Technical factors or variables considered in the algorithm

| Variable | Values |
|---|---|
| Collection source | OR vs. Clinic |
| Collection method | Banked FNA vs. Prospective FNA |
| Collection media | Trizol vs. RNAProtect |
| RNA RIN | Continuous |
| WTA yield | Continuous |

TABLE 3-continued

Technical factors or variables considered in the algorithm

| Variable | Values |
| --- | --- |
| ST yield | Continuous |
| Hybridization site | Laboratory 1 vs. Laboratory 2 |
| Hybridization quality (AUC) | Continuous |
| General pathology | Benign vs. Malignant |
| Subtype pathology | LCT, NHP, FA, HA, FC, FVPTC, PTC, MTC |
| Experiment batch | FNA TRIzol 1-4 vs. FNA RNAprotect 1-4 or FNA TRIzol vs. FNA RNAprotect |
| Lab contamination | Dominant peak, band seen, both |

Classification accuracy, sensitivity, specificity, ROC curves, error vs number of markers curves, positive predictive value (PPV) and negative predictive value (NPV) can be reported using these approaches. The methods of the present invention have sensitivity required to detect rare transcripts, which are expressed at a few copies per cell, and to reproducibly detect at least approximately two-fold differences in the expression levels. In some embodiments, the subject methods provide a high sensitivity of detecting gene expression and therefore detecting a genetic disorder or cancer that is greater than 60%, 65%, 70%, 75%, 80%, 85%, 90%, 91%, 92%, 93%, 94%, 95%, 95.5%, 96%, 96.5%, 97%, 97.5%, 98%, 98.5%, 99%, 99.5% or more. Therefore, the sensitivity of detecting and classifying a genetic disorder or cancer is increased. The classification accuracy of the subject methods in classifying genetic disorders or cancers can be greater than 70%, 75%, 80%, 85%, 90%, 91%, 92%, 93%, 94%, 95%, 95.5%, 96%, 96.5%, 97%, 97.5%, 98%, 98.5%, 99%, 99.5% or more. In some embodiments, the subject methods provide a high specificity of detecting and classifying gene expression that is greater than, for example, 80%, 85%, 90%, 91%, 92%, 93%, 94%, 95%, 95.5%, 96%, 96.5%, 97%, 97.5%, 98%, 98.5%, 99%, 99.5% or more. In some embodiments, the nominal specificity is greater than or equal to 70%. The nominal negative predictive value (NPV) is greater than or equal to 95%. In some embodiments, the NPV is about 95%, 95.5%, 96%, 96.5%, 97%, 97.5%, 98%, 98.5%, 99%, 99.5% or more.

4. Biomarker List Generation

The output of this method can be a marker list, such as a list which consists of the top differentially expressed genes distinguishing between benign and malignant. In some embodiments, the process of deriving marker lists uses three different analytical methods. In some embodiments, the present invention utilizes feature selection inside the classification engine, as a component of the cross-validation step (e.g. to refine the candidate genes list). Feature selection uses the repeatability criteria with the LIMMA model (Smyth 2004; Diaz-Uriarte and Alvarez de Andres 2006). The repeatability method has been described in the context of meta-analysis of microarray data (Fishel, Kaufman et al. 2007). For a fixed set of K genes and m cross-validation folds in the data, the selection probability of a feature is the number of folds that have been chosen by LIMMA as a discriminating feature between the Benign and Malignant classes divided by m. If the feature is chosen in every fold by LIMMA then the selection probability of that feature is 1. A maximum of K features are chosen in each fold of training and test set combination. At the end of repeatable feature selection, a union set of each of these distinct set of K features is taken and denoted by K' set of combined repeatable features. A repeatability threshold is set (e.g., 0.5 denotes that features must have appeared in half of the m cross-validation folds) in order to choose the highly consistent set of features from cross-validation.

Since feature selection can be done in conjunction with classification, repeatable feature selection can happen in an inner loop inside the cross-validation. Once the repeatable features are selected via the inner loop, they can be used for the classifier to make a call on the test set data of the outer cross-validation loop.

In some embodiments, feature selection (gene selection) can also be combined with technical factor removal. Often a variable, such as the sample collection media, provides a distinct shift at the intensity level. If the variable is associated with the disease subtype (Benign vs Malignant) then feature selection can account for this variable (a confounder) in the regression model (LIMMA). The details of accounting for technical factor effects on the intensities in feature selection are described in Section 3 above. Repeatable feature selection can be carried out together with correction/removal of relevant technical factors present in the data set for each regression model applied to the genes.

In addition to feature selection methods applied inside the cross-validation engine, more steps can be performed to output a final gene list after cross-validation is complete. In some embodiments, this gene list is not used on the same data set, but rather on subsequent data sets in order to obtain an unbiased estimate of the error rate. In some embodiments, in producing the final gene list, the following steps are taken:

Step 1: The top ranking genes from an initial discovery data set are identified using the LIMMA model based on significance after Benjamini and Hochberg correction for false discovery rate (FDR). An FDR filter value of p<0.05 was used. The list is ranked via the FDR p-value.

Step 2: A Bayesian approach is taken by augmenting the LIMMA model. First, previously published molecular profile studies are examined in order to derive type I and type II error rates of assigning a gene into a "benign" or "malignant" category. The error rates are calculated based on the sample size reported in each particular published study with an estimated fold-change value of two. Second, these prior probabilities are combined with the output of the Tissue dataset to estimate the posterior probability of differential gene expression. Lastly these probabilities are combined with the FNA dataset to formulate the final posterior probabilities of differential expression (Smyth 2004). These posterior probabilities are used to rank the genes and those that exceed a posterior probability threshold of 0.9 are selected. The list is then ranked via the posterior probability index.

Step 3: The repeatable gene list from the cross-validation analysis on the FNA data set is combined with an analogous list from the initial LIMMA only discovery data set (step 1). A joint core-set of features is created using the top ranked features that appear on both lists. The list is ranked via the repeatability index.

Step 4: The three lists (LIMMA, Bayes, and Repeatable), are combined to form a list of top markers (Combo) of size $\lambda$ with $\lambda=\min(\lambda 1+\lambda 2+\lambda 3)$, where $\lambda i$ is the length of the list from each of the three methods described herein.

Each of the steps described above can be done independently. In one embodiment, the subject method comprises step 1. In another embodiment, the subject method comprises step 2. In another embodiment, the subject method comprises step 3. In another embodiment, the subject method comprises step 4. In another embodiment, the subject method comprises a combination of steps 1, 2, 3, and/or 4.

5. Classification Methods

Pathology labels are the gold-standard used to characterize a given sample and these can be adjudicated after fine needle aspiration (FNA) cytology and/or post-surgical tissue cytology. A major limitation of using cytology to establish pathology is the arbitrary and error-prone nature of adjudicating a call. Tissues from any given organ maybe characterized as belonging to as many as ten or more "distinct" pathology subtypes. In the present invention subtype pathology labels are sometimes used to train the molecular classifier, but more often a variety of pathology subtypes are grouped together into a binary category: benign or malignant.

In one embodiment, data are from 10 prevalent thyroid subtypes that are present in the Tissue and FNA (Fine needle aspirate) samples. The subtypes include but are not limited to LCT, NHP, FA, HA (these 4 subtypes are benign) and the remaining subtypes are FC, HC, PTC, FVPTC, ATC, MTC (these 6 subtypes are malignant). The classifier separates the samples into benign or malignant.

In some embodiments, simplified pathology labels (benign or malignant) adjudicated to each sample by a trained pathologist are used to train the molecular classifier. However, it is recognized that pathology labels are often incorrect and their nomenclature may not necessarily describe the true nature of the pathology that actually exists in the sampled tissue. For example in thyroid cytology, nodular hyperplasias (NHP, a benign pathology) are relatively simple to distinguish from papillary carcinomas (PTC, a malignant pathology), while follicular adenomas (FA, a debated benign condition) are much harder to distinguish from follicular carcinomas (FC, a malignant pathology). In fact, the adjudication of an FA versus an FC pathology label maybe completely arbitrary and artificial. It has been argued that FA is simply the earliest recognizable stage of all eventual FCs (Tzen, Huang et al. 2003; Gombos, Zele et al. 2007). Cases of thyroid FA metastasis to other organs have been reported many years after complete thyroidectomy and pathology adjudication were performed, highlighting the severity of the problem (Kashigina, Girshin et al. 1980; Mizukami, Nonomura et al. 1996; Baloch and LiVolsi 2007; Ito, Yabuta et al. 2008; Tadashi 2009). Thus, while pathology labels remain the gold-standard in pathology diagnosis, the present invention overcomes some of its limitations by complementing training of the molecular classification algorithm with empirical data gathered during unsupervised analyses.

One goal of the molecular classifier is to separate all prevalent disease subtypes from any combination of sample cohorts (e.g. experiment 1+experiment 2) into a binary category: benign or malignant. A number of predictive modeling algorithms and or statistical methods are used to classify a given set of biomarkers to produce this binary class label per sample. The current method provides a modular molecular classifier useable in 1) "cross-validation mode", 2) "split-sample mode", and/or 3) "save model & predict mode". The framework of the molecular classifier is sufficiently flexible such that a variety of classification methods can be easily added and implemented in any mode. This feature of the molecular classifier allows the user to estimate classification performance and to obtain model parameters that improve classification. Classification methods include, but are not limited to, support vector machines (SVM), linear discriminant analysis (LDA, diagonal or pooled), K-nearest neighbor analysis (KNN), random forest (RF), lassoed logistic regress, MarginTree, Rulefit, Sum(UP regulated markers)-sum(DOWN regulated markers) etc.

(a) Cross-Validation Mode:

In cross-validation mode at least two methods can be used, either one at a time, or in succession. The cross-validation methods are K-fold cross-validation and leave-one-out cross-validation (LOOCV). In one embodiment, feature selection (with or without technical factor removal) is incorporated within each loop of cross-validation. This enables the user to obtain unbiased estimates of error rates. Further, feature selection can also be performed within certain classifiers (e.g., random forest) in a multivariate setting. The classifier takes the features selected and the previously built training-set model and makes a classification call (Benign or not Benign) on the test set. This procedure of repeatedly splitting the data into training and test sets and providing a single averaged error rate at the end gives an unbiased error rate in the cross-validation mode.

(b) Split Sample Mode

In split sample mode, samples can be split into a single training set and a single test (validation) set. The training set is used to obtain a model and its parameters. The validation set is used to obtain a generalized error estimate. There are two variations of the split sample processing procedure in our framework:

Training and validation data sets can be normalized and processed together (APT, RMA with quantile normalization) including removal of technical factors when necessary. The data can be split into training and validation sets based on specific criteria (e.g., balancing each set by relevant covariate levels).

The training set can be normalized and summarized first; then the validation set can be normalized to the APT sketch of the training set and summarized using the RMA of the training set and each additional validation sample. For example, if there are n test samples, this can be done n times. After RMA summarization, the datasets can be extracted and combined into one data set.

(c) Save Model and Predict Mode (Aka "Save and Predict")

This mode is similar to split sample mode except that the model and its parameters are generated and saved using an entire dataset, instead of splitting the data sets into training and validation sets. The validation set is provided externally.

6. Accuracy Determination Methods

In all three modes of model training described above, classification performance measures can include but are not limited to error rates, area under receiver operating characteristic (ROC) curve, false positive rate, false negative rate, PPV/NPV, etc. Two general aspects apply to all performance measures.

First, due to heterogeneity of the data sets with respect to pathology subtypes, performance varies by subtype and each measure is reported for individual subtypes. Second, since training data sets are not necessarily collected prospectively, training set prevalence of pathology subtypes is not reflective of the population prevalence. Accurate assessment of classification performance requires adjusting performance measures to their expected values given population pathology subtype prevalence.

(a) ROC

Receiver operator characteristic (ROC) curves can be used to visualize the trade-off between sensitivity and specificity (false negative/false positive errors). ROC curves can be generated both for training set disease subtype prevalence and population disease subtype prevalence.

The algorithms of the present invention (grey trace) demonstrate that current art methods (black trace) incorrectly assess classification performance (FIG. 4A). These errors in classification are highlighted when distinct pathology subtypes are probed independently of all other subtypes and re-sampled to generate a second—subtype specific—ROC curve of the data (FIG. 4B). The present invention improves the accuracy of classification performance calculation methods.

(b) Optimal Error Rate

Error rates of the optimal decision rule can be generated both for training set disease subtype prevalence and population disease subtype prevalence.

(c) PPV/NPV

Sensitivity/specificity of the classifier at a given decision threshold are converted to NPV/PPV using a range of values for the prevalence of malignancy. NPV/PPV values are generated both for training set disease subtype prevalence and population disease subtype prevalence.

(d) False Positive Error Rate Given False Negative Error Rate

Since the clinical diagnostic test can only tolerate a small number of false negative results, in some embodiments, classifiers are evaluated by comparing their false positive rates at an acceptable false negative threshold.

(e) Subtype Specific Error Rate

Error rates of the optimal decision rule are reported by disease subtype.

(f) Error Rates in Split-Sample Mode.

In some embodiments, two approaches are taken to quantify variability of the split sample estimate and evaluate the significance of its value:

(i) Generate a number of n=100 data sets of similar subtype make-up for split-sample training/testing using tissue data; run split sample mode analysis through classification for a single predefined number of markers (for example, 100); estimate the variance of error rate observed for the test set in each of 100 random splits. The distribution of error rate from this simulation is used to estimate error bars and confidence intervals for the achieved error.

(ii) In addition, the significance of achieved error rates can be evaluated against the null hypothesis classification all samples into the majority class. Let err be the achieved error rate, then the significance is the probability of observing err using baseline classifier that assigns everything to the majority class. The p-value for significance is the probability that pathology subtypes will be generated by re-sampling errors achieved on available samples in relevant proportions.

The estimates of metrics described in section 6 can be reported for each data set, as well as adjusted by re-sampling subtype prevalence to that present in any given pathgology subtype and reported again.

In some embodiments, the exon array platform used in the present invention measures mRNA levels of all known human genes (24,000) and all known transcripts (>200,000). This array is used on every sample run in feasibility (i.e. gene discovery), therefore the algorithm is trained on the full complement of genes at every step. Throughout algorithm training, feature (i.e. gene) selection occurs de novo for every experimental set. Thus, features may be selected from multiple experiments and later combined.

Marker panels can be chosen to accommodate adequate separation of benign from non-benign expression profiles. Training of this multi-dimensional classifier, i.e., algorithm, was performed on over 500 thyroid samples, including >300 thyroid FNAs. Many training/test sets were used to develop the preliminary algorithm. First the overall algorithm error rate is shown as a function of gene number for benign vs non-benign samples. All results are obtained using a support vector machine model which is trained and tested in a cross-validated mode (30-fold) on the samples.

In some embodiments, the difference in gene expression level is at least 10%, 15%, 20%, 25%, 30%, 35%, 40%, 45% or 50% or more. In some embodiments, the difference in gene expression level is at least 2, 3, 4, 5, 6, 7, 8, 9, 10 fold or more. In some embodiments, the biological sample is identified as cancerous with an accuracy of greater than 75%, 80%, 85%, 90%, 95%, 99% or more. In some embodiments, the biological sample is identified as cancerous with a sensitivity of greater than 95%. In some embodiments, the biological sample is identified as cancerous with a specificity of greater than 95%. In some embodiments, the biological sample is identified as cancerous with a sensitivity of greater than 95% and a specificity of greater than 95%. In some embodiments, the accuracy is calculated using a trained algorithm.

In some embodiments of the present invention, molecular profiling includes the step of binding the sample or a portion of the sample to one or more probes of the present invention. Suitable probes bind to components of the sample, i.e. gene products, that are to be measured and include but are not limited to antibodies or antibody fragments, aptamers, nucleic acids, and oligonucleotides. The method of diagnosing cancer based on molecular profiling further comprises the steps of detecting gene expression products (i.e. mRNA or protein) and levels of the sample, comparing it to an amount in a normal control sample to determine the differential gene expression product level between the sample and the control; and classifying the test sample by inputting one or more differential gene expression product levels to a trained algorithm of the present invention; validating the sample classification using the selection and classification algorithms of the present invention; and identifying the sample as positive for a genetic disorder or a type of cancer.

(i) Gene Expression Products and Splice Variants of the Present Invention

Molecular profiling may also include but is not limited to assays of the present disclosure including assays for one or more of the following: protein expression products, DNA polymorphisms, RNA expression products, RNA expression product levels, or RNA expression product splice variants of the genes. In some cases, the methods of the present invention provide for improved cancer diagnostics by molecular profiling of about 1, 2, 3, 4, 5, 6, 7, 8, 9, 10, 15, 20, 25, 30, 35, 40, 45, 50, 60, 70, 80, 90, 100, 120, 140, 160, 180, 200, 240, 280, 300, 350, 400, 450, 500, 600, 700, 800, 1000, 1500, 2000, 2500, 3000, 3500, 4000, 5000 or more gene product expression markers and/or alternative splice variant markers.

In one embodiment, molecular profiling involves microarray hybridization that is performed to determine gene expression product levels for one or more genes selected from FIG. 5, FIG. 6, FIG. 7, FIG. 8, or FIG. 9 of US Provisional application U.S. Ser. No. 61/199,585, and PCT application US2009/06162, which are hereby incorporated by reference in their entirety. In some cases, gene expression product levels of one or more genes from one group are compared to gene expression product levels of one or more genes in another group or groups. As an example only and without limitation, the expression level of gene TPO may be compared to the expression level of gene GAPDH. In another embodiment, gene expression levels are determined for one or more genes involved in one or more of the following metabolic or signaling pathways: thyroid hormone production and/or release, protein kinase signaling pathways, lipid kinase signaling pathways, and cyclins. In some cases, the methods of the present invention provide for analysis of gene expression product levels and or alternative exon usage of at least one gene of 1, 2, 3, 4, 5, 6, 7, 9, 10, 11, 12, 13, 14, or 15 or more different metabolic or signaling pathways.

(ii) Comparison of Sample to Normal

The results of the molecular profiling performed by the molecular profiling on the sample provided by the individual (test sample) may be compared to a biological sample that is known to be normal. A normal sample is that which is or is expected to be free of any cancer, disease such as a genetic disease, or condition, or a sample that would test negative for any cancer disease or condition in the molecular profiling assay. The normal sample may be from a different individual from the individual being tested, or from the same individual. The normal sample may be assayed at the same time, or at a different time from the test sample.

The results of an assay on the test sample may be compared to the results of the same assay on a normal sample. In some cases the results of the assay on the normal sample are from a database, or a reference. In some cases, the results of the assay on the normal sample are a known or generally accepted value by those skilled in the art. In some cases the comparison is qualitative. In other cases the comparison is quantitative. In some cases, qualitative or quantitative comparisons may involve but are not limited to one or more of the following: comparing fluorescence values, spot intensities, absorbance values, chemiluminescent signals, histograms, critical threshold values, statistical significance values, gene product expression levels, gene product expression level changes, alternative exon usage, changes in alternative exon usage, or nucleic acid sequences.

(iii) Evaluation of Results

In some embodiments, the molecular profiling results are evaluated using methods known to the art for correlating gene product expression levels or alternative exon usage with specific phenotypes such as malignancy, the type of malignancy (e.g. follicular carcinoma), or benignancy. In some cases, a specified statistical confidence level may be determined in order to provide a diagnostic confidence level. For example, it may be determined that a confidence level of greater than 90% may be a useful predictor of malignancy, type of malignancy, or benignancy. In other embodiments, more stringent or looser confidence levels may be chosen. For example, a confidence level of approximately 70%, 75%, 80%, 85%, 90%, 95%, 97.5%, 99%, 99.5%, or 99.9% may be chosen as a useful phenotypic predictor. The confidence level provided may in some cases be related to the quality of the sample, the quality of the data, the quality of the analysis, the specific methods used, and the number of gene expression products analyzed. The specified confidence level for providing a diagnosis may be chosen on the basis of the expected number of false positives or false negatives and/or cost. Methods for choosing parameters for achieving a specified confidence level or for identifying markers with diagnostic power include but are not limited to Receiver Operator Curve analysis (ROC), binormal ROC, principal component analysis, partial least squares analysis, singular value decomposition, least absolute shrinkage and selection operator analysis, least angle regression, and the threshold gradient directed regularization method.

(iv) Data Analysis

Raw gene expression level and alternative splicing data may in some cases be improved through the application of algorithms designed to normalize and or improve the reliability of the data. In some embodiments of the present invention the data analysis requires a computer or other device, machine or apparatus for application of the various algorithms described herein due to the large number of individual data points that are processed. A "machine learning algorithm" refers to a computational-based prediction methodology, also known to persons skilled in the art as a "classifier", employed for characterizing a gene expression profile. The signals corresponding to certain expression levels, which are obtained by, e.g., microarray-based hybridization assays, are typically subjected to the algorithm in order to classify the expression profile. Supervised learning generally involves "training" a classifier to recognize the distinctions among classes and then "testing" the accuracy of the classifier on an independent test set. For new, unknown samples the classifier can be used to predict the class in which the samples belong.

In some cases, the robust multi-array Average (RMA) method may be used to normalize the raw data. The RMA method begins by computing background-corrected intensities for each matched cell on a number of microarrays. The background corrected values are restricted to positive values as described by Irizarry et al. *Biostatistics* 2003 Apr. 4 (2): 249-64. After background correction, the base-2 logarithm of each background corrected matched-cell intensity is then obtained. The back-ground corrected, log-transformed, matched intensity on each microarray is then normalized using the quantile normalization method in which for each input array and each probe expression value, the array percentile probe value is replaced with the average of all array percentile points, this method is more completely described by Bolstad et al. Bioinformatics 2003. Following quantile normalization, the normalized data may then be fit to a linear model to obtain an expression measure for each probe on each microarray. Tukey's median polish algorithm (Tukey, J. W., *Exploratory Data Analysis.* 1977) may then be used to determine the log-scale expression level for the normalized probe set data.

Gene expression data may further be filtered to remove data that may be considered suspect. In some embodiments, data deriving from microarray probes that have fewer than about 4, 5, 6, 7 or 8 guanosine+cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine+cytosine nucleotides may be considered unreliable due to their aberrant hybridization propensity or secondary structure issues.

In some cases, unreliable probe sets may be selected for exclusion from data analysis by ranking probe-set reliability against a series of reference datasets. For example, RefSeq or Ensembl (EMBL) are considered very high quality reference datasets. Data from probe sets matching RefSeq or Ensembl sequences may in some cases be specifically included in gene expression analysis experiments due to their expected high reliability. Similarly data from probe-sets matching less reliable reference datasets may be excluded from further analysis, or considered on a case by case basis for inclusion. In some cases, the Ensembl high throughput cDNA (HTC) and/or mRNA reference datasets may be used to determine the probe-set reliability separately or together. In other cases, probe-set reliability may be ranked. For example, probes and/or probe-sets that match perfectly to all reference datasets such as for example RefSeq, HTC, and mRNA, may be ranked as most reliable (1). Furthermore, probes and/or probe-sets that match two out of three reference datasets may be ranked as next most reliable (2), probes and/or probe-sets that match one out of three reference datasets may be ranked next (3) and probes and/or probe sets that match no reference datasets may be ranked last (4). Probes and or probe-sets may then be included or excluded from analysis based on their ranking. For example, one may choose to include data from category 1, 2, 3, and 4 probe-sets; category 1, 2, and 3 probe-sets; category 1 and 2 probe-sets; or category 1 probe-sets for further analysis. In another example, probe-sets may be ranked by the number of base pair mismatches to reference dataset entries. It is understood that there are many methods understood in the art for assessing the reliability of a given probe and/or probe-set for molecular profiling and the methods of the present invention encompass any of these methods and combinations thereof.

In some embodiments of the present invention, data from probe-sets may be excluded from analysis if they are not expressed or expressed at an undetectable level (not above background). A probe-set is judged to be expressed above background if for any group:

Integral from T0 to Infinity of the standard normal distribution<Significance (0.01)

Where:

$T0 = Sqr(\text{GroupSize})(T-P)/Sqr(Pvar)$,

GroupSize=Number of CEL files in the group,
T=Average of probe scores in probe-set,
P=Average of Background probes averages of GC content, and
Pvar=Sum of Background probe variances/(Number of probes in probe-set)^2, This allows including probe-sets in which the average of probe-sets in a group is greater than the average expression of background probes of similar GC content as the probe-set probes as the center of background for the probe-set and enables one to derive the probe-set dispersion from the background probe-set variance.

In some embodiments of the present invention, probe-sets that exhibit no, or low variance may be excluded from further analysis. Low-variance probe-sets are excluded from the analysis via a Chi-Square test. A probe-set is considered to be low-variance if its transformed variance is to the left of the 99 percent confidence interval of the Chi-Squared distribution with (N−1) degrees of freedom.

$(N-1)*\text{Probe-set Variance}/(\text{Gene Probe-set Variance}) \sim \text{Chi-Sq}(N-1)$ where N is the number of input CEL files, (N−1) is the degrees of freedom for the Chi-Squared distribution, and the 'probe-set variance for the gene' is the average of probe-set variances across the gene.

In some embodiments of the present invention, probe-sets for a given gene or transcript cluster may be excluded from further analysis if they contain less than a minimum number of probes that pass through the previously described filter steps for GC content, reliability, variance and the like. For example in some embodiments, probe-sets for a given gene or transcript cluster may be excluded from further analysis if they contain less than about 1, 2, 3, 4, 5, 6, 7, 8, 9, 10, 11, 12, 13, 14, 15, or less than about 20 probes.

Methods of data analysis of gene expression levels and or of alternative splicing may further include the use of a pre-classifier algorithm. For example, fine needle aspirates (FNAs) of thyroid nodules contain several cell types, including thyroid follicular cells, thyroid medullary cells, blood cells (RBCs, WBCs, platelets), smooth muscle cells and infiltrating macrophages and lymphocytes. Diagnostic classification of FNAs involves primarily follicular cells (for cancers derived from the follicular cell such as papillary carcinoma, follicular carcinoma, and anaplastic thyroid carcinoma) and medullary cells (for medullary cancer). Since medullary and anaplastic thyroid cancers are rarely present in the indeterminate class, the diagnosis of indeterminate FNAs mainly concerns the distinction of follicular adenoma versus follicular carcinoma. The gene expression signal of the follicular cell is thus diluted out and possibly confounded by other cell types present in the FNA. An upfront method of determining the cellular make-up of a particular FNA may allow the resulting gene expression signatures to be calibrated against the dilution effect. A combination of known cell-specific genes may be used as an upfront mini-classifier for each cell component of the FNA. An algorithm may then use this cell-specific molecular fingerprint, pre-classify the samples according to their composition and then apply a correction/normalization factor. This data/information may then be fed in to a final classification algorithm which would incorporate that information to aid in the final diagnosis of Benign or Normal versus Malignant.

Genetic disorder or cancer diagnoses can be performed by comparing the levels of expression for a marker gene or a set of marker genes in a test sample, for example, a neoplastic cell sample to the levels of expression for a marker gene or a set of marker genes in a normal cell sample of the same tissue type. Alternatively, the level of expression for a marker gene or a set of marker genes in a cell sample is compared to a reference pool of RNA that represents the level of expression for a marker gene or a set of marker genes in a normal population (herein termed "training set"). The training set also includes the data for a population that has a known tumor or class of tumors. This data represents the average level of expression that has been determined for the neoplastic cells isolated from the tumor or class of tumors. It also has data related to the average level of expression for a marker gene or set of marker genes for normal cells of the same cell type within a population, in these embodiments, the algorithm compares newly generated expression data for a particular marker gene or set of marker genes from a cell sample isolated from a patient containing potentially neoplastic cells to the levels of expression for the same marker gene or set of marker genes in the training set. The algorithm determines whether a cell sample is neoplastic or normal by aligning the level of expression for a marker gene or set of marker genes with the appropriate group in the training set.

A statistical evaluation of the results of the molecular profiling may provide a quantitative value or values indicative of one or more of the following: the likelihood of diagnostic accuracy, the likelihood of cancer, disease or condition, the likelihood of a particular cancer, disease or condition, the likelihood of the success of a particular therapeutic intervention. Thus a physician, who is not likely to be trained in genetics or molecular biology, need not understand the raw data. Rather, the data is presented directly to the physician in its most useful form to guide patient care. The results of the molecular profiling can be statistically evaluated using a number of methods known to the art including, but not limited to: the students T test, the two sided T test, pearson rank sum analysis, hidden markov model analysis, analysis of q-q plots, principal component analysis, one way ANOVA, two way ANOVA, LIMMA and the like.

In some embodiments of the present invention, the use of molecular profiling alone or in combination with cytological analysis may provide a diagnosis that is between about 85% accurate and about 99% or about 100% accurate. In some cases, the molecular profiling business may through the use of molecular profiling and/or cytology provide a diagnosis of malignant, benign, or normal that is about 80%, 81%, 82%, 83%, 84%, 85%, 86%, 87%, 88%, 90%, 91%, 92%, 93%, 94%, 95%, 96%, 97%, 97.5%, 98%, 98.5%, 99%, 99.5%, 99.75%, 99.8%, 99.85%, or 99.9% accurate.

In some cases, accuracy may be determined by tracking the subject over time to determine the accuracy of the original diagnosis. In other cases, accuracy may be established in a deterministic manner or using statistical methods. For example, receiver operator characteristic (ROC) analysis may be used to determine the optimal assay parameters to achieve a specific level of accuracy, specificity, positive predictive value, negative predictive value, and/or false discovery rate. Methods for using ROC analysis in cancer diagnosis are known in the art and have been described for example in US Patent Application No. 2006/019615 herein incorporated by reference in its entirety.

In some embodiments of the present invention, gene expression products and compositions of nucleotides encoding for such products which are determined to exhibit the greatest difference in expression level or the greatest difference in alternative splicing between benign and normal, benign and malignant, or malignant and normal may be chosen for use as molecular profiling reagents of the present invention. Such gene expression products may be particularly useful by providing a wider dynamic range, greater signal to noise, improved diagnostic power, lower likelihood of false positives or false negative, or a greater statistical confidence level.

In other embodiments of the present invention, the use of molecular profiling alone or in combination with cytological analysis may reduce the number of samples scored as non-diagnostic by about 100%, 99%, 95%, 90%, 80%, 75%, 70%, 65%, or about 60% when compared to the use of standard cytological techniques known to the art. In some cases, the methods of the present invention may reduce the number of samples scored as intermediate or suspicious by about 100%, 99%, 98%, 97%, 95%, 90%, 85%, 80%, 75%, 70%, 65%, or about 60%, when compared to the standard cytological methods used in the art.

In some cases the results of the molecular profiling assays, are entered into a database for access by representatives or agents of the molecular profiling business, the individual, a medical provider, or insurance provider. In some cases assay results include interpretation or diagnosis by a representative, agent or consultant of the business, such as a medical professional. In other cases, a computer or algorithmic analysis of the data is provided automatically. In some cases the molecular profiling business may bill the individual, insurance provider, medical provider, researcher, or government entity for one or more of the following: molecular profiling assays performed, consulting services, data analysis, reporting of results, or database access.

In some embodiments of the present invention, the results of the molecular profiling are presented as a report on a computer screen or as a paper record. In some cases, the report may include, but is not limited to, such information as one or more of the following: the number of genes differentially expressed, the suitability of the original sample, the number of genes showing differential alternative splicing, a diagnosis, a statistical confidence for the diagnosis, the likelihood of cancer or malignancy, and indicated therapies.

(v) Categorization of Samples Based on Molecular Profiling Results

The results of the molecular profiling may be classified into one of the following: negative (free of a cancer, disease, or condition), diagnostic (positive diagnosis for a cancer, disease, or condition), indeterminate or suspicious (suggestive of a cancer, disease, or condition), or non diagnostic (providing inadequate information concerning the presence or absence of a cancer, disease, or condition). In some cases, a diagnostic result may classify whether a subject has a genetic disorder. In some cases, a diagnostic result may further classify the type of cancer, disease or condition. In other cases, a diagnostic result may indicate a certain molecular pathway involved in the cancer disease or condition, or a certain grade or stage of a particular cancer disease or condition. In still other cases a diagnostic result may inform an appropriate therapeutic intervention, such as a specific drug regimen like a kinase inhibitor such as gleevac or any drug known to the art, or a surgical intervention like a thyroidectomy or a hemithyroidectomy.

In some embodiments of the present invention, results are classified using a trained algorithm. Trained algorithms of the present invention include algorithms that have been developed using a reference set of known malignant, benign, and normal samples. The classification scheme using the algorithms of the present invention is shown in FIG. 1. Algorithms suitable for categorization of samples include but are not limited to k-nearest neighbor algorithms, concept vector algorithms, naive bayesian algorithms, neural network algorithms, hidden markov model algorithms, genetic algorithms, and mutual information feature selection algorithms or any combination thereof. In some cases, trained algorithms of the present invention may incorporate data other than gene expression or alternative splicing data such as but not limited to scoring or diagnosis by cytologists or pathologists of the present invention, information provided by the pre-classifier algorithm of the present invention, or information about the medical history of the subject of the present invention.

(vi) Monitoring of Subjects or Therapeutic Interventions via Molecular Profiling In some embodiments, a subject may be monitored using methods and compositions of the present invention. For example, a subject may be diagnosed with cancer or a genetic disorder. This initial diagnosis may or may not involve the use of molecular profiling. The subject may be prescribed a therapeutic intervention such as a thyroidectomy for a subject suspected of having thyroid cancer. The results of the therapeutic intervention may be monitored on an ongoing basis by molecular profiling to detect the efficacy of the therapeutic intervention. In another example, a subject may be diagnosed with a benign tumor or a precancerous lesion or nodule, and the tumor, nodule, or lesion may be monitored on an ongoing basis by molecular profiling to detect any changes in the state of the tumor or lesion.

Molecular profiling may also be used to ascertain the potential efficacy of a specific therapeutic intervention prior to administering to a subject. For example, a subject may be diagnosed with cancer. Molecular profiling may indicate the upregulation of a gene expression product known to be involved in cancer malignancy, such as for example the RAS oncogene. A tumor sample may be obtained and cultured in vitro using methods known to the art. The application of various inhibitors of the aberrantly activated or dysregulated pathway, or drugs known to inhibit the activity of the pathway may then be tested against the tumor cell line for growth inhibition. Molecular profiling may also be used to monitor the effect of these inhibitors on for example downstream targets of the implicated pathway.

(viii) Molecular Profiling as a Research Tool

In some embodiments, molecular profiling may be used as a research tool to identify new markers for diagnosis of suspected tumors; to monitor the effect of drugs or candidate drugs on biological samples such as tumor cells, cell lines, tissues, or organisms; or to uncover new pathways for oncogenesis and/or tumor suppression.

Examples

Example 1: Biological Sample Processing

All tissues and FNAs were collected under IRB approved protocols.

Tissue Procurement

Prior to obtaining FNAs from prospective collections, thyroid surgical tissue samples can be purchased from a clinical tissue vendor. In some embodiments, the samples are selected from their proprietary tissue database, RNA is extracted by the laboratory, 50 ng amplified using the NuGEN Pico kit, and hybridized to exon arrays.

Sample Collection, Preservation and Transport

The FNA needed to be collected into a preservative that allows for the stabilization of DNA and RNA immediately following collection in the clinic, as well as through subsequent shipping and handling. In some embodiments, the present method identifies a collection medium that allows isolation of both DNA and RNA from the FNA samples.

A study to compare different collection media is performed. In some embodiments, FNAs collected from post operative thyroid tissue are collected into each collection media. FNAs from five individual thyroids were collected into Trizol (Invitrogen), RNAlater (Ambion), RNAprotect (Qiagen) and the cytology medium PreservCyt (Cytyc). RNA and DNA were purified from each of these FNAs using the Qiagen Allprep DNA/RNA micro method and the Trizol RNA purification protocol for Trizol samples. Overall, samples collected in RNAprotect produced the highest yield and quality of both RNA and DNA and therefore RNAprotect was utilized for all future studies. For all prospective FNA studies, the FNA was collected into 1.25 ml of RNAprotect, frozen at −80° C. and shipped to Veracyte on dry ice.

Non-Frozen Shipping and Stability Study

The aim of this study was to investigate the stability of FNAs in RNAprotect when shipped at 2-8° C. and the effects of freezing on nucleic acid yield and quality data on the stability of FNAs in RNAprotect.

To minimize effects of temperature variability in this study, samples were transported in shipping containers validated to keep the sample at 2-8° C. for 24 hrs (Thermosafe/Fisher 03-525-054). FNAs collected on Monday through Thursday were transferred to shipping containers and shipped overnight to Veracyte. FNAs collected on Friday were stored over the weekend at 4° C. and shipped to Veracyte on Monday alongside with samples collected on Monday. Upon arrival the samples were split into three groups:

1. Upon receipt, samples will be centrifuged and the pellet frozen on dry ice and stored at −80° C. for later purification (n=26).
2. Upon receipt, samples will be centrifuged and the pellet immediately used for nucleic acid purification (n=29).
3. Upon receipt, samples will be immediately frozen on dry ice and stored at −80° C. for later purification (n=25).

RNA and DNA were purified from each of these FNAs using the Qiagen Allprep DNA/RNA micro method. Metrics for RNA and DNA yield were collected. These data were compared with that from samples previously collected from the same site using the original sample collection protocol (Group 0). For RNA, no significant difference was observed in yield, or in 260/280 and 260/230 ratios between groups. RIN value was also not altered between Group 0 and Groups 2 and 3. However, Group 1 (pelleted cells) did show a reduction in RIN value. Samples taken on Friday, stored at 4° C. over the weekend and then shipped overnight showed no difference in yield or quality to those shipped overnight. This study therefore indicates that samples can be shipped non-frozen at 2-8° C. and that samples are stable at this temperature out to 72 hrs.

Sample Preparation/Extraction

We desired that nucleic acids be extracted from the FNAs using simple molecular biology methods and preferably using commercially available kits. Qiagen All-Prep method was used as the method e for RNA/DNA extraction and purification. Additionally, the RNA purification protocol within the Allprep process was modified, following Qiagen's optional protocol, to capture microRNA within the total RNA population. Further optimization of this method was carried out to show that an 18 ul elution volume gave the best combination of yield and sample concentration. In some embodiments, TRIzol extraction of samples was used. From the majority of patients from which a FNA was taken, a buccal DNA swab was also collected.

Nucleic Acid Quantification

A number of techniques for RNA quantification are available. Both the Nanodrop spectrophotometer (Thermo Scientific) and the Bioanalyzer (Agilent) have been used. In later experiments the fluorescent based method, Quant-IT RNA (Invitrogen), has been tested. DNA quantification has been carried out using the Nanodrop spectrophotometer and PicoGreen fluorescent based method (Invitrogen) with quality checked by gel electrophoresis. Quantification data and sample usage is captured in RNA and DNA master spreadsheets.

With RNA of high concentrations, both Nanodrop and Bioanalyzer quantify RNA accurately. However, at low concentrations of RNA and with the presence of contaminants in the sample that absorb at 230 nM, the agreement between Nanodrop and Bioanalyzer decreases. In some embodiments, the subject method provides a fluorescent based method, Quant IT RNA (Invitrogen), to aid quantification of these samples.

NuGEN Amplification

The low RNA yields from thyroid FNAs necessitates amplification of the material for downstream microarray analysis. Two NuGEN protocols have been considered, the Pico kit and the FFPE kit. The former is specified for very low starting amounts and the latter is designed for degraded RNA samples from paraffin-embedded samples. Given that the samples are both low yield and are degraded, we tested which kit would be more suitable for clinical FNA samples.

The WT Ovation FFPE RNA amplification system V2 is a fast and simple method for preparing amplified cDNA from total RNA of low quality for gene expression studies. Amplification is initiated at the 3' end and randomly throughout the whole transcriptome in the sample enabling the amplification of degraded RNA. When starting with 50 ng of severely degraded RNA (such as FFPE derived material), this system can generate microgram quantities of cDNA. With higher quality RNA, lower input amounts can be used to generate the required amounts of cDNA for analysis on GeneChip arrays. A linear isothermal DNA amplification process, termed Ribo-SPIA amplification, is at the heart of this process. The WT Ovation Pico system is very similar to the WT Ovation FFPE system, with both using the SPIA amplification process. The Pico kit (AI-11) is designed for amplifying small amounts of RNA but has not been optimized for use with degraded RNA.

Labeled Sense strand cDNA is recommended for the Affymetrix GeneChip Exon 1.0 ST array. Therefore antisense cDNA from the SPIA amplification is used as a template in WT-Ovation Exon module to generate sense strand cDNA. This is fragmented and labeled using the FL-Ovation cDNA biotin module. Intermediates generated in this process are evaluated for quality and quantity. This information is captured in the associated workbook and utilized in subsequent downstream analysis.

When running the NuGEN WT-Ovation FFPE process a no template control (NTC) is routinely run. Due to the high level of amplification present in this system, the NTC is not empty but generally contains <3 ug of material. To avoid contamination, a thorough clean of the entire lab area was carried out. All opened consumables (including plastics and reagents) were disposed of and cleaning of lab benches, shelves, cupboards and equipment with 10% bleach, DNA away, RNAse Zap and 70% EtOH was performed. Floors were also cleaned with 10% bleach, as well as a general cleaning product. A strict workflow that separates pre- and post-PCR steps has been introduced to prevent the generation and spread of this PCR amplicon. Subsequent to this clean up, Glory plates 5, 6, 4, and 7 were run with no evidence of amplicon contamination in the samples.

Affymetrix Exon Array

The Affymetrix GeneChip Exon 1.0 ST array is designed with probes across the length of an mRNA transcript enabling expression profiling at both the gene and the exon level (AI-12). Hybridization controls are added (GeneChip Hybridization Control kit, Affymetrix) and the sample hybridized to the GeneChip followed by washing, staining and scanning (using the GeneChip HWS Kit on GeneChip Fluidics Station 450 and GeneChip scanner 3000 7G).

Control RNA

In some embodiments, a control RNA is utilized. This universal human RNA (UHR) purchased from Stratagene is a mixture of 10 cell lines from different tissues and is detailed in AI-7.

Illumina System

The Ilumina whole genome DASL assay was outsourced to Expression Analysis and run using 100 ng total RNA following their standard protocol.

Nanostring nCounter System

The Nanostring nCounter assay was outsourced to Nanostring and run using 200 ng of total RNA following their standard protocol.

Sample Details for Discovery Datasets

Tissue-thyroid surgical tissue samples were purchased from a clinical tissue vendor. The samples were selected from their proprietary tissue database, RNA was extracted by a laboratory services vendor, 50 ng amplified using the NuGEN Pico kit, and hybridized to exon arrays.

FNA in TRIzol—This study on banked and prospective FNAs collected into both RNAprotect and TRIzol was split into two arms. Forty-eight samples were run by a laboratory services vendor using a 50 ng input (as determined by Nanodrop) into the NuGEN FFPE process and hybridized to exon arrays. The second arm consisted of 102 samples (2 batches), of which 12 were duplicates from arm 1. These samples were run internally, using an input of 25 ng (as determined by Nanodrop) into the NuGEN FFPE process and hybridized to exon arrays.

FNA in RNAProtect—This study on predominantly prospective FNAs collected into RNAprotect was run internally in a total of 7 batches. A total of 312 samples were run, using an input of 25 ng (as determined by Nanodrop) into the NuGEN FFPE process and hybridized to exon arrays.

Example 2: Fluid Decision (Goldfish)

The aim of this study was to investigate whether the use of RNAprotect or TRIzol results in differences in assay performance and if so, which performs the best. Samples for this study were 10 paired ex vivo FNA samples collected in both TRIzol and RNAprotect. Additionally, samples composed of mixtures of NHP: PTC were set up in triplicate at a ratio of 100:0, 80:20, 60:40 and 0:100, respectively.

In summary, 3 out of 4 prehyb+post-hyb metrics showed significant differences between RNAprotect and TRIzol. Additionally, when analyzing all samples by PCA, samples cluster by media type, not biology in the first two PCs. Analysis of heatmaps generated from 2700 DE genes discovered from tissue and 230 DE genes indicate that biology was preserved when clustering samples. Within the mixture analysis study, RNAprotect seems to perform better than TRIzol; also RNAprotect is less variable than TRIzol. This study supports the continued use of RNAprotect as the thyroid FNA collection fluid.

Example 3: NuGEN FFPE Vs Pico Amplification Protocol Decision

A total of 22 samples were included in this study, made up of banked FNAs, ex vivo FNAs and prospective FNAs all collected in TRIzol. These samples were chosen to cover a range of RIN values. RNA was sent to a laboratory services vendor and processed through the NuGEN WT-Ovation FFPE and Pico amplification kits. Intended input concentrations for this assay were 100 ng for FFPE and 50 ng for Pico. However, subsequent re-quantitation of a subset of these samples with Nanodrop indicates that lower concentrations were used. This observation equally impacted FFPE and Pico results.

The results indicate that the NuGEN FFPE kit performed better than Pico in these samples. Importantly, both methods were useable for samples of RIN>2. Neither assay was able to rescue highly degraded samples with a RIN<2.

Example 4: Platform Evaluation for Use of Degraded RNA Samples

This study was initiated to determine which technology was best suited to dealing with a range of good quality and degraded RNA samples. The platforms that were evaluated were the Affymetrix Exon Array with the NuGEN WT-Ovation FFPE process carried out at a laboratory services vendor (50 ng input), the Illumina whole genome DASL assay carried out at Expression Analysis (using 100 ng input RNA), and the Nanostring nCounter system carried out at Nanostring (100 ng and 200 ng input RNA). RNA samples were a selection of banked FNAs, ex vivo FNAs and prospective FNAs all collected in TRIzol. The samples had a range of RIN values (1-8) from highly degraded to intact samples and two sample subtypes (NHP/PTC).

In summary, although Nanostring was the only platform that did not require amplification of RNA, it was slightly less robust than Exon/FFPE and DASL at low RIN ranges, possibly due to the placement of primers at approximately 200 bp. The Exon/FFPE and DASL systems are comparable across the range of sample characteristics tested. While the Illumina Whole-Genome DASL array performed as well as the NuGEN FFPE/Affymetrix exon assay the decision was made to proceed with the NuGEN/Affymetrix system because of FDA readiness considerations of the various microarray platforms.

Example 5: Titration of Input Amount (Nemo)

This study was designed to investigate lower input of RNA into the NuGEN WT-Ovation FFPE amplification system followed by hybridization on Affymetrix exon arrays. Samples for this study were seven ex vivo FNA samples collected RNAprotect. This study was split into two arms, A and B, with each arm run by a different operator. Each ex vivo FNA sample was run internally using an input of 25 ng, 15 ng and 10 ng total RNA (as determined by Nanodrop) into the NuGEN FFPE process and hybridized to exon arrays. Matching samples from the fluid decision (Goldfish) study run using an input of 50 ng total RNA were included in this analysis.

It was noted that Arm B samples showed poorer pre-hyb metrics at the Sense strand stage (ST-yield) and that the SPIA cDNA yield (WT-yield) was higher in this experiment than that observed in the Goldfish fluid decision study but no severe batch effect was observed by PCA analysis of expressed genes. From analysis of post-hyb metrics and gene level expression, the input amount of 15 ng and 25 ng seem comparable, however experiment may lack power to detect changes between them, whereas 10 ng show clear differences from the rest. The conclusion from this study was to use 25 ng of total RNA as input amount into the NuGEN WT-Ovation FFPE amplification system starting with the FNA in TRIzol internal discovery set.

Example 6: Titration of Input Volume

The purpose of this experiment is to test for the effect of increased total input RNA volume or Speed Vac concentrated input RNA on the SPIA cDNA and ST cDNA yield and the gene expression data from the NuGEN FFPE Exon Array Protocol. The results from this experiment show that a Speed Vac concentration of RNA to reduce starting volume has no measurable effects on RNA by Bioanalyzer results in terms of size distribution and RIN values. Cross-contamination of samples was not detected in the water negative control by Bioanalyzer graphs from before and after Speed Vac concentration, ruling out the Speed Vac as a source of carry-over contamination. The increased input RNA volume up to 2× standard volume does not affect 2×SPIA cDNA and ST cDNA amplification or quality based on OD260/280, OD260/230, total yield and Bioanalyzer graphs and RIN and that overall, gene expression was not affected by the increased input RNA volume based on post hybridization quality or gene expression. In conclusion, this study demonstrated that either using Speed Vac to concentrate starting RNA volume or increasing starting volume up to 2× volume can be used in the Exon SOP without any significant alteration to the process.

Example 7: Algorithm and Marker Results

The results of Classification applied on various discovery data sets are reported in chronological order of the data sets analyzed. In discovery, first a Tissue data set was analyzed (surgical tissue sample), secondly, a data set composed of a small number of FNAs was analyzed and, lastly, a large set of FNA samples were analyzed in two batches (FNA in TRIzol and FNA in RNAProtect). A .CEL file list which contains the name of the experiment, sample IDs, and where the samples were processed are included in Attachment B (Experimental CEL file).

i. TISSUE Data Set

The phased approach to discovery started with Tissue samples and went on to include a few Banked FNA samples and a large pool of Banked and Prospective FNA samples. The first discovery data set was comprised of 261 Tissue samples, procured from a clinical tissue vendor and an academic center and processed at an external laboratory. A Simple PCA plot revealed that the MTC (medullary thyroid cancer) and LcT (Lymphocytic Thyroiditis) were easily separable, but the rest of the benign and malignant subtypes were indistinguishable from this view. A sophisticated, non-linear algorithm working in multi-dimensional space was in order. Clustering, an unsupervised technique, showed preliminary evidence of structure of disease subtypes in Tissue samples.

Two hundred and sixty one (261) .CEL files arrived at Veracyte from the laboratory services vendor and some samples were excluded because they were not benign or malignant categories of primary interest (n=28), or they were normal thyroid (n=12) or they were ATC/MTC (n=25). Some samples were removed for QC reasons (n=5) (Intron/Exon separation AUC<0.73). This resulted in 179 .CEL files for subsequent analysis.

Classification results using a variety of classifiers yielded about a 15% error rate (overall) with just over 100 genes. The error rates varied by subtype. Higher error rates were observed for benign samples with malignant counterparts (FA vs FC, HA vs FC). The results show that pair-wise comparison of subtypes yield a very different picture of accuracy and number of differentially expressed (D.E.) genes: the harder the separation between a pair of subtypes, the fewer the number of D.E. genes and higher the error rate.

MTC separation was a relatively easier task in the mix of subtypes, while many differentially expressed genes were detected, only 3 literature markers were required to clearly distinguish the class from others.

Initial planning was done using the fold-change values observed in the Tissue data set to estimate the number of FNA samples that were going to be needed for discovery. A fold change of 1.8 was observed for a typical D.E. gene in the PTC category and a minimum of 60 samples were necessary to train for the classifier for this subclass. The discovery data sets generated subsequently, comprised of FNAs, were well above this sample size as prescribed by this planning analysis.

An initial marker list was also generated from a subset of the tissue samples at this time and the markers were filed for Patent application. The Tissue samples (n=75) were used to extract B vs M markers (N=2765) at gene level, D.E. markers using probeset level analysis (1740) and alternatively spliced genes (N=2868). The union of these marker sets was a list of 4918 unique markers.

TISSUE+Banked FNA Data Set

The Tissue data set was augmented by 45 banked FNA samples of well represented subtype mix from one investigator. The RNA was extracted using TRIzol. They were processed by a laboratory services vendor. However the samples were marked by poor RNA quality. The FNA samples had more variable Intron-exon separation AUC than the Tissue samples. Using the AUC=0.75 threshold 20 .CEL files were removed. One ATC .CEL file was also removed resulting in a total of 24 FNA samples to be analyzed.

The two primary objectives were to assess the degradation impact in these FNA samples and to investigate whether the biological signal found in Tissue samples transfer to the banked FNA samples despite degradation. Known, high intensity D.E. markers, e.g., MET, were found to be class separating in Surgical Tissue samples very well, but moderately on Prospective FNA samples and very poorly on banked FNA samples. Classification performance dropped in the Banked FNA samples. For gene-level classification, the error rate jumped from 16.3% (VIKING) to 32% (Banked FNA). Two main sources of differences were identified for the performance gap from Tissue samples: (1) Technical: sample degradation and small cellular yields/sample quality and (2) Biological: class heterogeneity, cellular mixture.

Fold-change (PTC vs NHP) in TISSUE samples vs FNA Samples (Banked) yielded a slope of 0.6, intercept=0.08 and $R^2$=0.78, Fold-change (PTC vs NHP) in TISSUE samples vs FNA Samples (Banked) yielded a slope of 0.85, intercept=0.24 and $R^2$=0.79. The concordance between the fold change levels in the prospective FNA set compared to the Tissue set was the preliminary evidence we needed to proceed to the next level of discovery where we would accrue, process and analyze a large pool of FNA samples, a substantial proportion of them being prospective FNAs.

The results of applying the Combo Marker list process to surgical tissue sample+the Banked FNA data set is a total of 230 markers. The performance of the Combo marker list (n=230) looked promising when applied to a limited set of 18 prospective FNA samples. However the true test of this marker list was the classification accuracy of subsequent data sets (FNA in TRIzol and FNA in RNAProtect).

FNA in TRIzol

The first complete data set of Thyroid FNA samples consisting of cytology codes=I, B, M or U were available to us to discover marker sets and build our classifier in March 2009. FNA in TRIzol was a well designed experiment consisting of 206 FNA samples. 22 samples in this data set were from the FFPE experiment, 36 samples were from Ex-vivo FNA using TRIzol or RNAProtect experiment. FNA in TRIzol also contained 48 samples run by an external laboratory services vendor. In addition, FNA in TRIzol had 95 unique samples that were run at Veracyte. Five samples did not generate .CEL files, 14 samples failed to meet the AUC criterion of 0.73, 17 .CEL files did not meet the pDet criterion of 0.21. Further duplicated samples (which were run at an external laboratory and an in-house or internal laboratory) were removed. Samples with CYN (Colloid Nodule), MTC and ATYP subtypes were removed leading to 127 .CEL files to be analyzed.

The classification error rate as shown in the gene titration curve was poor at 18%. The Combo marker list (K=230) reduced the rate to 13% but still was considered to be too high. It was found that the Banked FNA samples (n=67) from a particular investigator (called cFNA samples) looked very different from the rest of the samples with respect to (i) WTA conc and (ii) pDet. These samples did not vary that much in ST conc or AUC. These samples were dropped from subsequent analysis. The classification error rates in the remaining samples (n=86) dropped to ~10%. A simple classifier, which took the signs (+1 for up-regulation and −1 for down-regulation) of the markers and added them up, performed well in separating the benign from the malignant classes.

FNA in TRIzol+FNA in RNAProtect

The second discovery data set was named FNA in RNAProtect. A carefully planned experiment yielded in 312 FNA samples to be processed at Veracyte in six batches (G1-G6). Of these 9 samples did not generate CEL files. Heavy primer amplicon contamination was observed in the lab after G1-G3 were run (see description of contamination detection and clean up in section 10.1.6 mNuGEN Amplification). As a result, thirteen samples were excluded from these batches due to heavy contamination. The usual two post-hyb metrics, AUC and pDet (pDABG) were used to filter out more samples. The Intron-exon separation AUC<0.73 criteria excluded only 2 samples. The pDET criteria <0.21 did not apply to the FNA in RNAProtect experiment. Many samples in this experiment, unlike FNA in TRIzol, fell below pDET=0.29.

First Data Set

A higher threshold of 0.29 was used in the data set which will be explained later in this section. Using this higher threshold, 128 samples dropped out from the analysis flow. This is roughly 40% of the samples. Lastly nodule size exclusion criterion of 1 cm and those with mPTC and mFVPTC surgical pathology labels were dropped from the analysis (6 samples). At the end we analyzed data from 227 samples.

The subtype representation in this data set is: CN:8, CYN:3, FA:19, FC:4, FVPTC:20, HA:7, LCT:30, NHP:86 and PTC:50. Classification error rate was approximately 10%. MTC samples (n=4) could be differentiated perfectly from all other subtypes with very few markers). The # genes by error titration curves were generated using both LIMMA (univariate gene selection) and Random Forest (multivariate gene selection). The titration curves for the 5 classifiers look pretty stable at this error rate after K=60 genes onwards. The gene by error rate titration curve was regenerated using the re-sampled subtype prevalence in indeterminate category. The error rate increased to about 16%. When the error rates were examined in the cytology=Indeterminate category only with re-sampled weights from subtype prevalence in the indeterminate category, the error rate jumped to 25%. The error titration curves were generated using both LIMMA (univariate gene selection) and Random Forest (multivariate gene selection).

In addition to cross-validate mode, the split-sample mode was used to train the classifier on cytology code=B, M or U and predict on cytology code=I samples, The error rate was 23% which was close to the last comparison stated in the previous paragraph. This is the best estimate of overall error rate in samples in cytology code=I category. Technical factor removal algorithm was applied to make the samples in TRIzol and RNAprotect more comparable. The resulting improvement is subtle at the classification error rate level but at the intensity levels the slope=0.88 improves to slope=−1 amongst the markers.

Second Data Set

Starting with n=227 data set, we restricted the data set to RNAprotect samples to assess whether classification rate remains the same or not. For our clinical trials, the molecular classifier will be calling benign or not benign on FNA samples collected in RNAprotect only. Data from 135 samples in this data set are analyzed.

The subtype representation in this data set is: CN:7, CYN:3, FA:10, FC:3, FVPTC:9, HA:1, LCT:18, NHP:55 and PTC:29. Classification error rate was approximately 5%. The # genes by error titration curves were generated using both LIMMA (univariate gene selection) and Random Forest (multivariate gene selection). The titration curves for the 5 classifiers look pretty stable at this error rate after K=40 genes onwards. The gene by error rate titration curve was regenerated using the re-sampled subtype prevalence in indeterminate category. The error rate increased to about 10%. When the error rates were examined in the cytology=Indeterminate category only with re-sampled weights from subtype prevalence in the indeterminate category, the error rate jumped to 22%. The error titration curves were generated using both LIMMA (univariate gene selection) and Random Forest (multivariate gene selection).

The ROC curves for this data set estimated a sensitivity of 82% and specificity of 95.5%. The black ROC curves are the estimates of sensitivity and specificity for the subtype prevalence present in the data set. The red ROC curves are re-drawn with the estimates recalculated when the subtype prevalence is what should from the cytology=I category.

The results of applying the COMBO Marker list process to VIKING+FNA in TRIzol_FNA in RNAProtect data sets is a total of total 226 markers. The intersection of the COMBO process applied to various data sets give highly overlapping marker sets.

pDET Threshold of 0.29 Derived

The pDET QC metric with a threshold of 0.29 was used in this data set to enable discovery on high quality samples. The lab contamination which affected sample quality differentially over different batches led us to examine G1-G3 separately from batches G5-G7. Lab was cleaned after finishing G3. Sample performance in the classifier looked worse after this lab cleanup. Since batch G5 was heavily biased towards high quality samples, it did not show poor performance as G4, G6 and G7. The classifier was built on the good batches (G1-G3, G5) discarding the samples which were affected by contamination and predicted on samples in G4, G6, G7. The results showed that several PTC samples have a malignancy score of 0 just like the benign samples in this test set. The misclassification of the PTC samples was heavily correlated with two post-hyb QC metrics: pDET and AG/Core overlap. The threshold of 0.29 was thus derived as a necessary condition for a sample to classify correctly.

pDET was modeled in a linear (ANOVA) model with several upstream QC metrics. After controlling for many factor, it appeared that the batch variable (later FNA in RNAProtect batches) were worse than earlier FNA in RNAProtect batches. Similarly low Bioanalyzer input amounts, low ST.conc and low WTA.conc were also indicative of poor pDET values downstream. These results were statistically significant.

FVPTC, cytology=I vs FVPTC, cytology=M comparison

Error rates were investigated by subtypes in cytology=I class vs cytology=B,M class. The malignant category where the classifier performs the best is PTC. In the FVPTC class was different: the error rates were only 9% in FVPTC, cytology=M subclass, but was 77% in the FVPTC, cytology=I subclass. This distinction between error rates was statistically significant. Investigating this further showed that FVPTC, cytology=I were indistinguishable from NHPs. The UP and down regulated markers have become insensitive in this class.

Habitual Offenders

The frequency of misclassification for the classifier was plotted to see which samples the algorithm is prone to misclassifying. A score of 1 in the y-axis designates that the sample is misclassified by each type of classifier algorithm embedded in Classification. As predicted, many FVPTCs are on the list, however some are exonerated after expert re-reads.

Bloodiness

The lab scored about 159 samples on a 4-point scale of bloodiness: b0, b1, b2 and b3, where the b0 is the least bloody and b3 is the most bloody sample category. These were more accurate on the RNAprotect samples, since TRIzol also lyses blood cells and therefore it is hard to make a visual call of bloodiness by lab personnel. A gene-expression based marker was derived for bloodiness based on the genes shown in Table 4.

TABLE 4

List of Markers for Bloodiness

| Probe set ID | Gene Symbol | Gene Description |
|---|---|---|
| 3642664 | HBA1 | blood, hemoglobin |
| 3642675 | HBA1 | blood, hemoglobin |
| 3642664 | HBA2 | blood, hemoglobin |
| 3642675 | HBA2 | blood, hemoglobin |
| 3360401 | HBB | blood, hemoglobin |
| 3360417 | HBB | blood, hemoglobin |
| 3360432 | HBBP1 | blood, hemoglobin |
| 3360417 | HBD | blood, hemoglobin |
| 3360456 | HBE1 | blood, hemoglobin |
| 3360441 | HBG1 | blood, hemoglobin |
| 3360456 | HBG1 | blood, hemoglobin |
| 3360441 | HBG2 | blood, hemoglobin |
| 3360456 | HBG2 | blood, hemoglobin |
| 3642654 | HBM | blood, hemoglobin |
| 3642687 | HBQ1 | blood, hemoglobin |
| 3642643 | HBZ | blood, hemoglobin |
| 3642652 | HBZ | blood, hemoglobin |

The gene expression marker was available on all samples and correlated well with the laboratory visual marker when it was available. The continuous score of this marker was divided into quartiles: m0, m1, m2 and m3. Classification error rates were investigated in the 4 categories of both the laboratory-based and gene-expression-based bloodiness marker. Classification rates did not seem to vary over these categories. Marker lists were derived with no adjustment for bloodiness (by means of technical factor removal), by adjustment for bloodiness with presence of disease label in model and by adjustment for bloodiness without presence of disease label in model. The marker lists were compared and found to be completely overlapping for 85% of the genes. This confirmed that bloodiness did not impact classification accuracy or marker list in this data set of RNAprotect samples.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

Baloch, Z. W. and V. A. LiVolsi (2007). "Our approach to follicular-patterned lesions of the thyroid." *J Clin Pathol* 60(3): 244-50.

Diaz-Uriarte, R. and S. Alvarez de Andres (2006). "Gene selection and classification of microarray data using random forest." *BMC Bioinformatics* 7: 3.

Fishel, I., A. Kaufman, et al. (2007). "Meta-analysis of gene expression data: a predictor-based approach." *Bioinformatics* 23(13): 1599-606.

Gombos, K., E. Zele, et al. (2007). "Characterization of microarray gene expression profiles of early stage thyroid tumours." *Cancer Genomics Proteomics* 4(6): 403-9.

Ito, Y., T. Yabuta, et al. (2008). "Distant and lymph node metastases of thyroid nodules with no pathological evidence of malignancy: a limitation of pathological examination." *Endocr J* 55(5): 889-94.

Kashigina, E. A., S. G. Girshin, et al. (1980). "[Metastasizing adenoma of the thyroid]." *Vestn Rentgenol Radiol*(3): 68-70.

Mizukami, Y., A. Nonomura, et al. (1996). "Late bone metastasis from an encapsulated follicular carcinoma of the thyroid without capsular and vascular invasion." *Pathol Int* 46(6): 457-61.

Smyth, G. K. (2004). "Linear models and empirical bayes methods for assessing differential expression in microarray experiments." *Stat Appl Genet Mol Biol* 3: Article3.

Tadashi, T. (2009). "Brain metastasis from thyroid adenomatous nodules or an encapsulated thyroid follicular tumor without capsular and vascular invasion: a case report." *Cases Journal* 2(7180).

Tzen, C. Y., Y. W. Huang, et al. (2003). "Is atypical follicular adenoma of the thyroid a preinvasive malignancy?" *Hum Pathol* 34(7): 666-9.

What is claimed is:

1. A method for processing a thyroid tissue sample of a subject, comprising:
   (a) obtaining said thyroid tissue sample of said subject, which thyroid tissue sample comprises gene expression products;
   (b) subjecting a first portion of said thyroid tissue sample to cytological testing that identifies said thyroid tissue sample as ambiguous or suspicious;
   (c) upon identifying said thyroid tissue sample as ambiguous or suspicious, assaying by sequencing, array hybridization, or nucleic acid amplification said gene expression products of a second portion of said thyroid tissue sample;
   (d) determining differential gene expression product levels of said gene expression products with respect to one or more control samples, to yield data corresponding to said differential gene expression product levels;
   (e) inputting said data to a trained algorithm to generate a classification of said thyroid tissue sample as positive or negative for a thyroid condition at an accuracy of at least about 90%, wherein a plurality of technical factor variables is selectively removed from said data and normalized prior to or during classification; and
   (f) electronically outputting a report that identifies said classification of said thyroid tissue sample as positive or negative for said thyroid condition.

2. The method of claim 1, wherein said plurality of technical factor variables includes one or more members selected from the group consisting of: collection source, collection method, collection media, ribonucleic acid integrity number, whole transcriptome amplification yield, sense strand yield, hybridization site, hybridization quality and experiment batch.

3. The method of claim 1, wherein said gene expression products include messenger ribonucleic acid (mRNA).

4. The method of claim 3, wherein said mRNA has a ribonucleic acid integrity number (RIN) of 2.0 or more.

5. The method of claim 3, wherein a portion of said mRNA is used for multi-gene microarray analysis, and wherein said thyroid tissue sample has an RIN of equal to or less than 5.0.

6. The method of claim 1, wherein said assaying comprises using one or more of the following: microarray, SAGE, blotting, reverse transcriptase polymerase chain reaction (PCR), or quantitative PCR.

7. The method of claim 1, wherein said thyroid condition is a thyroid cancer.

8. The method of claim 7, wherein said trained algorithm generates said classification at an accuracy of at least about 90% for at least two subtypes of thyroid cancer.

9. The method of claim 1, wherein said trained algorithm is trained with multiple datasets of differential gene expression product levels obtained from a plurality of training samples.

10. The method of claim 1, wherein said assaying comprises measuring mRNA from said second portion of said thyroid tissue sample.

11. The method of claim 1, wherein said one or more control samples are obtained from said subject, another subject, a tissue or cell bank, or any combination thereof.

12. The method of claim 1, wherein said thyroid tissue sample has a benign thyroid condition, and wherein said trained algorithm does not classify said thyroid tissue sample as positive for cancer.

13. The method of claim 1, wherein said thyroid tissue sample has a malignant thyroid condition, and wherein said trained algorithm classifies said thyroid tissue sample as positive for cancer.

14. The method of claim 1, wherein said trained algorithm generates said classification at a specificity of at least about 70%.

15. The method of claim 14, wherein said trained algorithm generates said classification at a specificity of at least about 80%.

16. The method of claim 15, wherein said trained algorithm generates said classification at a specificity of at least about 90%.

17. The method of claim 1, wherein said trained algorithm generates said classification at a sensitivity of at least about 60%.

18. The method of claim 17, wherein said trained algorithm generates said classification at a sensitivity of at least about 70%.

19. The method of claim 18, wherein said trained algorithm generates said classification at a sensitivity of at least about 80%.

20. The method of claim 1, wherein said gene expression products are selected based on said plurality of technical factor variables.

21. The method of claim 1, wherein said trained algorithm is trained for a subset of genes corresponding to said gene expression products.

22. The method of claim 1, wherein said trained algorithm is trained with a plurality of samples comprising ambiguous or suspicious samples.

23. The method of claim 1, wherein, (i) when said classification identifies said thyroid tissue sample as negative for said thyroid condition, obtaining a second thyroid tissue sample from said subject and repeating (c)-(f) to monitor a change over time in said differential gene expression product levels, or (ii) when said classification identifies said thyroid tissue sample as positive for said thyroid condition, treating said subject by a thyroidectomy.

24. The method of claim 1, wherein said first portion is different from said second portion.

* * * * *